US011299701B2

(12) United States Patent
Sasaki

(10) Patent No.: US 11,299,701 B2
(45) Date of Patent: *Apr. 12, 2022

(54) CULTURE-MEDIUM-MONITORING APPARATUS

(71) Applicant: OLYMPUS CORPORATION, Hachioji (JP)

(72) Inventor: Hiroshi Sasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

This patent is subject to a terminal disclaimer.

(21) Appl. No.: 16/802,665

(22) Filed: Feb. 27, 2020

(65) Prior Publication Data

US 2020/0299630 A1 Sep. 24, 2020

(30) Foreign Application Priority Data

Mar. 19, 2019 (JP) .............................. JP2019-050547
Apr. 4, 2019 (JP) .............................. JP2019-071737

(51) Int. Cl.
*C12M 1/00* (2006.01)
*C12M 3/00* (2006.01)
(Continued)

(52) U.S. Cl.
CPC ............ *C12M 41/06* (2013.01); *C12M 23/06* (2013.01); *C12M 27/02* (2013.01); *C12M 31/08* (2013.01);
(Continued)

(58) Field of Classification Search
CPC ....... C12M 41/06; C12M 31/08; C12M 27/02
See application file for complete search history.

(56) References Cited

U.S. PATENT DOCUMENTS 5,982,534 A   11/1999   Pinkel et al.
6,238,911 B1   5/2001   Kasahara
(Continued)

FOREIGN PATENT DOCUMENTS

EP   3392332 A1   10/2018
JP   S60164715 A   8/1985
(Continued)

OTHER PUBLICATIONS

International Search Report (ISR) (and English language translation thereof) and Written Opinion dated Nov. 6, 2018 issued in International Application No. PCT/JP2018/032376.
(Continued)

*Primary Examiner* — Nathan A Bowers
(74) *Attorney, Agent, or Firm* — Holtz, Holtz & Volek PC

(57) ABSTRACT

Provided is a culture-medium-monitoring apparatus including: an optical measurement unit that includes an illumination light source and a collecting lens that radiate an illumination light onto a culturing liquid, a retroreflective member that has an array in which micro-reflective elements are arrayed, that is disposed so as to sandwich the vessel between the retroreflective member, and the illuminating light source and the collecting lens, and that reflects the illumination light passed through the culturing liquid in the vessel, and a light detector that detects an intensity of the illumination light passed through the culturing liquid in the vessel after being reflected by the retroreflective member; and a control portion that causes the intensity of the illumination light to be repeatedly detected at a prescribed timing, and that determines a state of the culturing liquid on the basis of a change over time in the intensity of the illumination light.

11 Claims, 34 Drawing Sheets

(51) Int. Cl.

| | | |
|---|---|---|
| *C12M 1/36* | (2006.01) | |
| *C12M 1/06* | (2006.01) | |
| *C12M 1/12* | (2006.01) | |
| *G06T 7/194* | (2017.01) | |
| *H04N 9/04* | (2006.01) | |
| *H04N 5/225* | (2006.01) | |
| *G06T 7/90* | (2017.01) | |
| *C12M 1/34* | (2006.01) | |

(52) U.S. Cl.
CPC ............ *C12M 41/26* (2013.01); *C12M 41/48* (2013.01); *G06T 7/194* (2017.01); *G06T 7/90* (2017.01); *H04N 5/2256* (2013.01); *H04N 9/045* (2013.01); *G06T 2207/10024* (2013.01); *G06T 2207/30024* (2013.01)

(56) References Cited

U.S. PATENT DOCUMENTS

| | | | |
|---|---|---|---|
| 6,415,236 | B2 | 7/2002 | Kobayashi et al. |
| 7,952,693 | B2 | 5/2011 | Serebrennikova et al. |
| 8,591,836 | B2 | 11/2013 | Boege et al. |
| 9,482,659 | B2 * | 11/2016 | Loewke .................. C12Q 3/00 |
| 2003/0085335 | A1 | 5/2003 | Almogy et al. |
| 2004/0061042 | A1 | 4/2004 | Almogy et al. |
| 2005/0208473 | A1 | 9/2005 | Krichevsky et al. |
| 2008/0259313 | A1 | 10/2008 | Berndt |
| 2011/0118572 | A1 | 5/2011 | Bechtel et al. |
| 2012/0140215 | A1 | 6/2012 | Kao et al. |
| 2012/0140224 | A1 * | 6/2012 | Switkes .................. G01N 21/78 356/369 |
| 2012/0301872 | A1 * | 11/2012 | Tormod ............. G01N 21/6456 435/5 |
| 2015/0093819 | A1 * | 4/2015 | Zhang .................... C12M 25/16 435/302.1 |
| 2017/0067009 | A1 * | 3/2017 | Sloane ................. C12N 5/0062 |
| 2018/0045944 | A1 | 2/2018 | Suzuki |
| 2018/0252648 | A1 | 9/2018 | Dohi |
| 2018/0291328 | A1 | 10/2018 | Sasaki et al. |
| 2019/0154567 | A1 * | 5/2019 | Herzog ................. G01N 21/253 |
| 2020/0029875 | A1 | 1/2020 | Hirano et al. |
| 2020/0165558 | A1 | 5/2020 | Shevitz |
| 2020/0239827 | A1 | 7/2020 | Sasaki et al. |
| 2020/0379231 | A1 | 12/2020 | Dohi |

FOREIGN PATENT DOCUMENTS

| | | |
|---|---|---|
| JP | S62115297 A | 5/1987 |
| JP | H0427909 A | 1/1992 |
| JP | H09292572 A | 11/1997 |
| JP | 2000004871 A | 1/2000 |
| JP | 2000227556 A | 8/2000 |
| JP | 2002508857 A | 3/2002 |
| JP | 2005533996 A | 11/2005 |
| JP | 2006174764 A | 7/2006 |
| JP | 2013511713 A | 4/2013 |
| JP | 2016034235 A | 3/2016 |
| JP | 2016041042 A | 3/2016 |
| JP | 2017046620 A | 3/2017 |
| JP | 2017140006 A | 8/2017 |
| JP | 2018146602 A | 9/2018 |
| JP | 2019179061 A | 10/2019 |
| WO | 9318136 A1 | 9/1993 |
| WO | 9857748 A1 | 12/1998 |
| WO | 0117420 A1 | 3/2001 |
| WO | 03040709 A3 | 1/2004 |
| WO | 2011062548 A1 | 5/2011 |
| WO | 2012077081 A1 | 6/2012 |
| WO | 2016185619 A1 | 11/2016 |
| WO | 2017104696 A1 | 6/2017 |
| WO | 2017144218 A1 | 8/2017 |
| WO | 2018163785 A1 | 9/2018 |
| WO | 2019163167 A1 | 8/2019 |
| WO | 2019188765 A1 | 10/2019 |
| WO | 2019234916 A1 | 12/2019 |
| WO | 2019235563 A1 | 12/2019 |

OTHER PUBLICATIONS

Japanese Office Action (and English language translation thereof) dated Dec. 15, 2020, issued in Japanese Application No. 2017-037920.
Office Action (Non-Final Rejection) dated Jun. 30, 2021, issued in related U.S. Appl. No. 16/745,530.
Related U.S. Appl. No. 16/745,530; First Named Inventor: Hiroshi Sasaki; Title: "Erythrocyte Monitoring Device"; filed Jan. 17, 2020.
Related U.S. Appl. No. 16/997,156; First Named Inventor: Masahito Dohi; Title: Observation Apparatus; filed Aug. 19, 2020.
Hirose, et al., "Immortalization of Erythroblasts by c-MYC and BCL-XL Enables Large-Scale Erythrocyte Production from Human Pluripotent Stem Cells", Stem Cell Reports, International Society for Stem Cell Research (ISSCR), Dec. 17, 2013, vol. 1, pp. 499-508.
Office Action (Non-Final Rejection) dated Dec. 27, 2021, issued in related U.S. Appl. No. 16/745,530.

* cited by examiner

CULTURE-MEDIUM-MONITORING APPARATUS

CROSS-REFERENCE TO RELATED APPLICATIONS

This application is based on Japanese Patent Application No. 2019-050547 and Japanese Patent Application No. 2019-071737, the contents of which are incorporated herein by reference.

TECHNICAL FIELD

The present invention relates to a culture-medium-monitoring apparatus.

BACKGROUND ART

In recent years, in the field of regenerative medicine using cultured cells including iPS cells (induced pluripotent stem cells), there is a demand for increasing the scale of culturing. Cell culturing methods include adhesion culturing, in which cells are cultured in a small vessel such as a flask and a petri dish, and suspension culturing, in which a culture medium is stirred in a large vessel such as a bioreactor so that cells are cultured in a state in which the cells are suspended in the culture medium. In order to culture a large quantity of cells, suspension culturing, in which the culturing efficiency is not affected by the size of an area to which cells adhere, is superior to adhesion culturing; therefore, suspension culturing is being increasingly employed instead of adhesion culturing (for example, see Patent Literature 1). With the technology described in Patent Literature 1, images of cells in a vessel are acquired to ascertain the culturing situation of suspended cells in a vessel.

In cell culturing, culturing cells for an extended period of time results in deterioration of the culture medium. Because of this, it is necessary to periodically check the degree of culture medium deterioration and to replace the culture medium in the case in which the culture medium deterioration has advanced (for example, see Patent Literature 2). The technology described in Patent Literature 2 periodically measures the optical transmittance of a culture medium in which cells are being cultured to determine the state of the culture medium, thus identifying the timing for replacing the culture medium.

In general, a suspension-culturing bioreactor is cylindrical, and a stirrer provided with a plurality of stirring blades for stirring a culturing liquid is inserted into the bioreactor. Accordingly, in order to apply the absorbance measuring system described in Patent Literature 2 to a bioreactor, an illumination light beam is radiated and detected from a direction intersecting a center axis of the bioreactor so as to avoid the stirrer.

CITATION LIST

Patent Literature

{PTL 1} Japanese Unexamined Patent Application, Publication No. 2017-140006
{PTL 2} PCT International Publication No. 2017/104696

SUMMARY OF INVENTION

An aspect of the present invention is a culture-medium-monitoring apparatus including: an optical measurement unit that includes an illuminating portion that radiates an illumination light beam onto a culture medium in a vessel, a retroreflective member that has an array in which a plurality of micro-reflective elements are arrayed, that is disposed so as to sandwich the vessel between the illuminating portion and the retroreflective member, and that reflects the illumination light beam that has passed through the culture medium in the vessel, and a light-detecting portion that detects an intensity of the illumination light beam that has passed through the culture medium in the vessel after being reflected by the retroreflective member; and a control portion that causes the intensity of the illumination light beam to be repeatedly detected at a prescribed timing by controlling the optical measurement unit, and that determines a state of the culture medium on the basis of a change over time in the intensity of the illumination light beam.

The culture medium-monitoring apparatus according to the above-described aspect may include a notifying portion that issues a notification about information to a user, wherein the control portion may issue, by means of the notifying portion, a notification about a timing for replacing the culture medium to the user.

The culture-medium-monitoring apparatus according to the above-described aspect may include: a culture-medium-supplying portion that supplies the culture medium to the vessel; and a culture-medium-discharging portion that discharges the culture medium from the vessel, wherein, in the case in which the control portion determines that the timing for replacing the culture medium has arrived on the basis of the change over time in the intensity of the illumination light beam detected by the light-detecting portion, a portion of the culture medium may be discharged from the vessel by means of the culture-medium-discharging portion, and a new culture medium may be supplied to the vessel by means of the culture medium-supplying portion.

The culture medium-monitoring apparatus according to the above-described aspect may include a stirrer that stirs the culture medium in the vessel, wherein the control portion may cause a speed at which the culture medium is stirred by the stirrer to be reduced when detecting the intensity of the illumination light beam by means of the light-detecting portion.

In the culture-medium-monitoring apparatus according to the above-described aspect, the optical measurement unit may include a detection optical system that causes an image of cells suspended in the culture medium irradiated with the illumination light beam to be formed on the light-detecting portion.

In the culture-medium-monitoring apparatus according to the above-described aspect, the optical measurement unit may include a phase contrast optical system that generates a phase contrast image of the cells.

The culture-medium-monitoring apparatus according to the above-described aspect may include a stirrer that stirs the culture medium in the vessel, wherein the control portion may repeatedly perform detection of the intensity of the illumination light beam and acquisition of the image of the cells by means of the light-detecting portion, may cause the speed at which the culture medium is stirred by the stirrer to be reduced when detecting the intensity of the illumination light beam, and may cause the culture medium to be stirred without reducing the speed at which the culture medium is stirred by the stirrer when acquiring the image of the cells.

In the culture-medium-monitoring apparatus according to the above-described aspect, the illuminating portion may include a monochromatic light source that emits the illumination light beam at a single wavelength.

In the culture-medium-monitoring apparatus according to the above-described aspect, the monochromatic light source may include a white light source and a bandpass filter that extracts only the single wavelength from a light beam emitted from the white light source.

In the culture-medium-monitoring apparatus according to the above-described aspect, the monochromatic light source may be an LED light source.

In the culture-medium-monitoring apparatus according to the above-described aspect, the illuminating portion may include a monochromatic light source that emits, as the illumination light beam, a plurality of monochromatic light beams at different wavelengths, wherein the control portion may determine the state of the culture medium on the basis of changes over time in intensities of the light beams at the respective wavelengths that have passed through the culture medium and that are detected by the light-detecting portion.

In the culture-medium-monitoring apparatus according to the above-described aspect, the monochromatic light source may include: a white light source; and a plurality of bandpass filters that are provided so that said bandpass filters can be inserted into and retracted from a path of a light beam emitted from the white light source, and that extract, from the light beam coming from the white light source, only single wavelengths that differ from each other.

In the culture-medium-monitoring apparatus according to the above-described aspect, the monochromatic light source may include a plurality of LED light sources at different wavelengths.

Another aspect of the present invention is a culture-medium-monitoring apparatus including: an illuminating portion that radiates an illumination light beam onto a specific region in which cells and a culture medium are present in a vessel; an image-acquisition portion that acquires an image of the specific region by capturing an image of an observation light beam coming from the specific region irradiated with the illumination light beam; an image-analyzing portion that divides the image of the specific region acquired by the image-acquisition portion into pixels containing the cells and background pixels, and that calculates a representative pixel value that represents the background pixels; and a control portion that repeatedly acquires images of the specific region at a prescribed timing by means of the image-acquisition portion, that calculates the representative pixel values of the individual acquired images of the specific region by means of the image-analyzing portion, and that determines the state of the culture medium on the basis of changes over time in the calculated representative pixel values.

The culture-medium-monitoring apparatus according to the above-described aspect may include a retroreflective member that has an array in which a plurality of microreflective elements are arrayed, that is disposed so as to sandwich the vessel between the illuminating portion and the retroreflective member, and that reflects the illumination light beam that has passed through the specific region in the vessel, wherein the image-acquisition portion may acquire an image of the specific region irradiated again with the illumination light beam that has been reflected by the retroreflective member.

In the culture-medium-monitoring apparatus according to the above-described aspect, the illuminating portion may include an oblique illumination optical system that obliquely illuminates the specific region from a direction that is inclined with respect to an optical axis of the image-acquisition portion.

In the culture-medium-monitoring apparatus according to the above-described aspect, the illuminating portion and the image-acquisition portion may form a phase contrast optical system that generates a phase contrast image of the specific region.

The culture-medium-monitoring apparatus according to the above-described aspect may include a housing that has a transparent portion that allows a light beam to pass therethrough, and that accommodates the illuminating portion and the image-acquisition portion, wherein, in a state in which the housing is inserted into the culture medium in the vessel, the illumination light beam may be radiated onto the specific region by means of the illuminating portion via the transparent portion, and an image of the specific region may be acquired by means of the image-acquisition portion through the transparent portion.

The culture-medium-monitoring apparatus according to the above-described aspect may include a reflective member that obliquely illuminates the specific region by reflecting, toward the image-acquisition portion, the illumination light beam that has been made to exit to outside the housing from the illuminating portion via the transparent portion.

The culture-medium-monitoring apparatus according to the above-described aspect may include a tubular protective tube that covers a periphery of the housing, wherein the reflective member may be provided at a distal end of the protective tube.

The culture-medium-monitoring apparatus according to the above-described aspect may include a notifying portion that issues a notification about information to the user, wherein the control portion issues, by means of the notifying portion, a notification about a timing for replacing the culture medium to the user.

The culture-medium-monitoring apparatus according to the above-described aspect may include a culture-medium-supplying portion that supplies the culture medium to the vessel; and a culture-medium-discharging portion that discharges the culture medium from the vessel, wherein, in the case in which the control portion determines that the timing for replacing the culture medium has arrived, a portion of the culture medium may be discharged by means of the culture-medium-discharging portion, and the new culture medium may be supplied to the vessel by means of the culture-medium-supplying portion.

In the culture-medium-monitoring apparatus according to the above-described aspect, the illuminating portion may include a monochromatic light source that emits the illumination light beam at a single wavelength.

In this case, the monochromatic light source may include a white light source and a bandpass filter that extracts only the single wavelength from a light beam emitted from the white light source, and the monochromatic light source may be an LED light source.

In the culture-medium-monitoring apparatus according to the above-described aspect, the illuminating portion may include a monochromatic light source that emits, as the illumination light beam, a plurality of monochromatic light beams at different wavelengths, wherein the control portion may determine the state of the culture medium on the basis of changes over time in the representative pixel values of the background pixels of the individual images of the specific region acquired by the image-acquisition portion for the respective wavelengths of the monochromatic light beams radiated onto the specific region.

In the culture-medium-monitoring apparatus according to the above-described aspect, the monochromatic light source may include: a white light source; and a plurality of bandpass filters that are provided so that said bandpass filters can be inserted into and retracted from a path of the light beam emitted from the white light source, and that extract, from a light beam coming from the white light source, only single wavelengths that differ from each other.

In the culture-medium-monitoring apparatus according to the above-described aspect, the monochromatic light source may include a plurality of LED light sources at different wavelengths.

In the culture-medium-monitoring apparatus according to the above-described aspect, the illuminating portion may include a white light source, the image-acquisition portion may include a color CCD, and the control portion may determine the state of the culture medium on the basis of the relationship between hue and pH of the culture medium determined from the background pixels of an image of the specific region acquired by the color CCD.

DESCRIPTION OF EMBODIMENTS

First Embodiment

A culture-medium-monitoring apparatus according to a first embodiment of the present invention will be described below with reference to the drawings.

Figure 1:
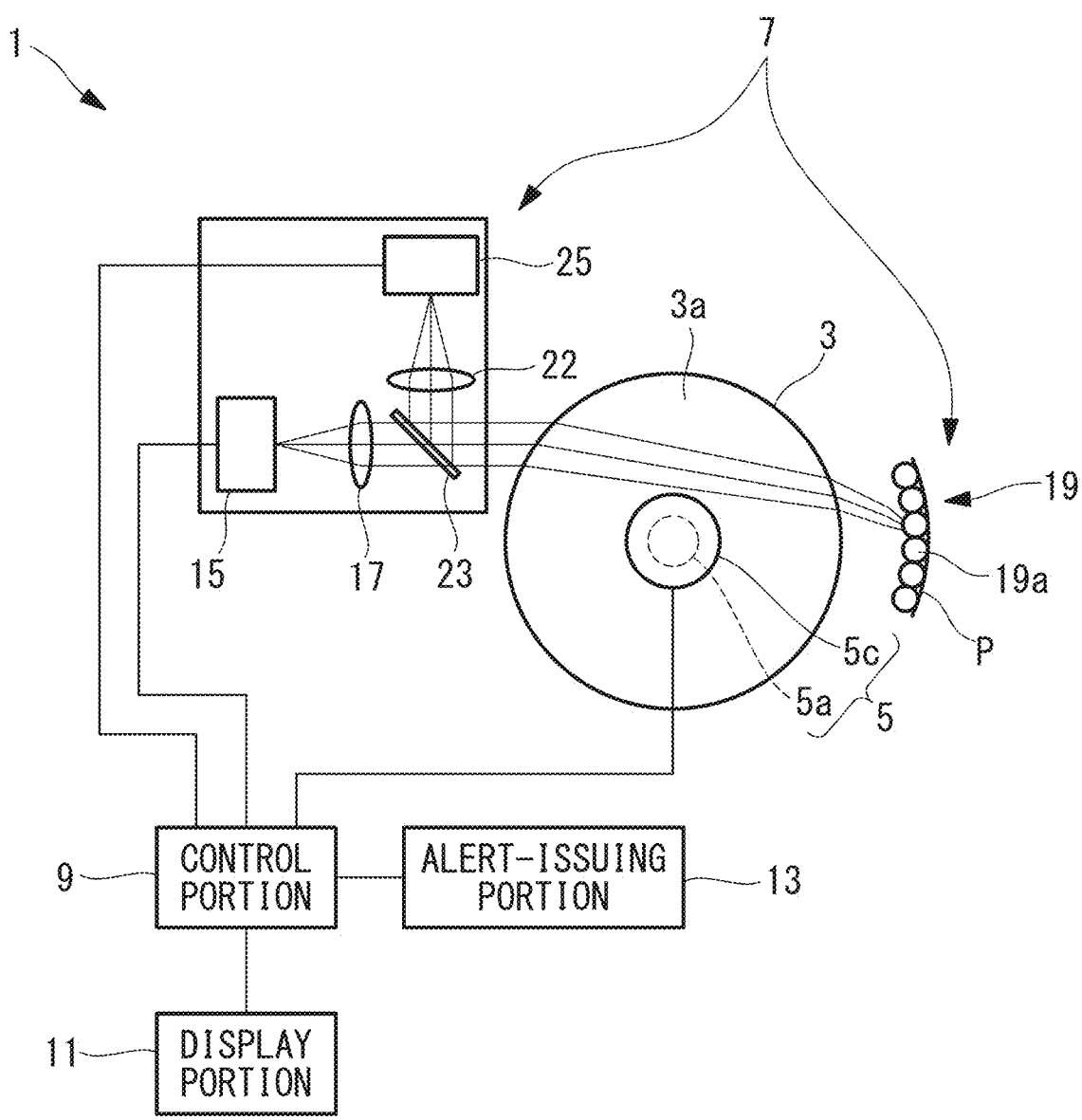
FIG. 1 is a schematic configuration diagram showing, from above, a culture-medium-monitoring apparatus according to a first embodiment of the present invention.
Figure 2:
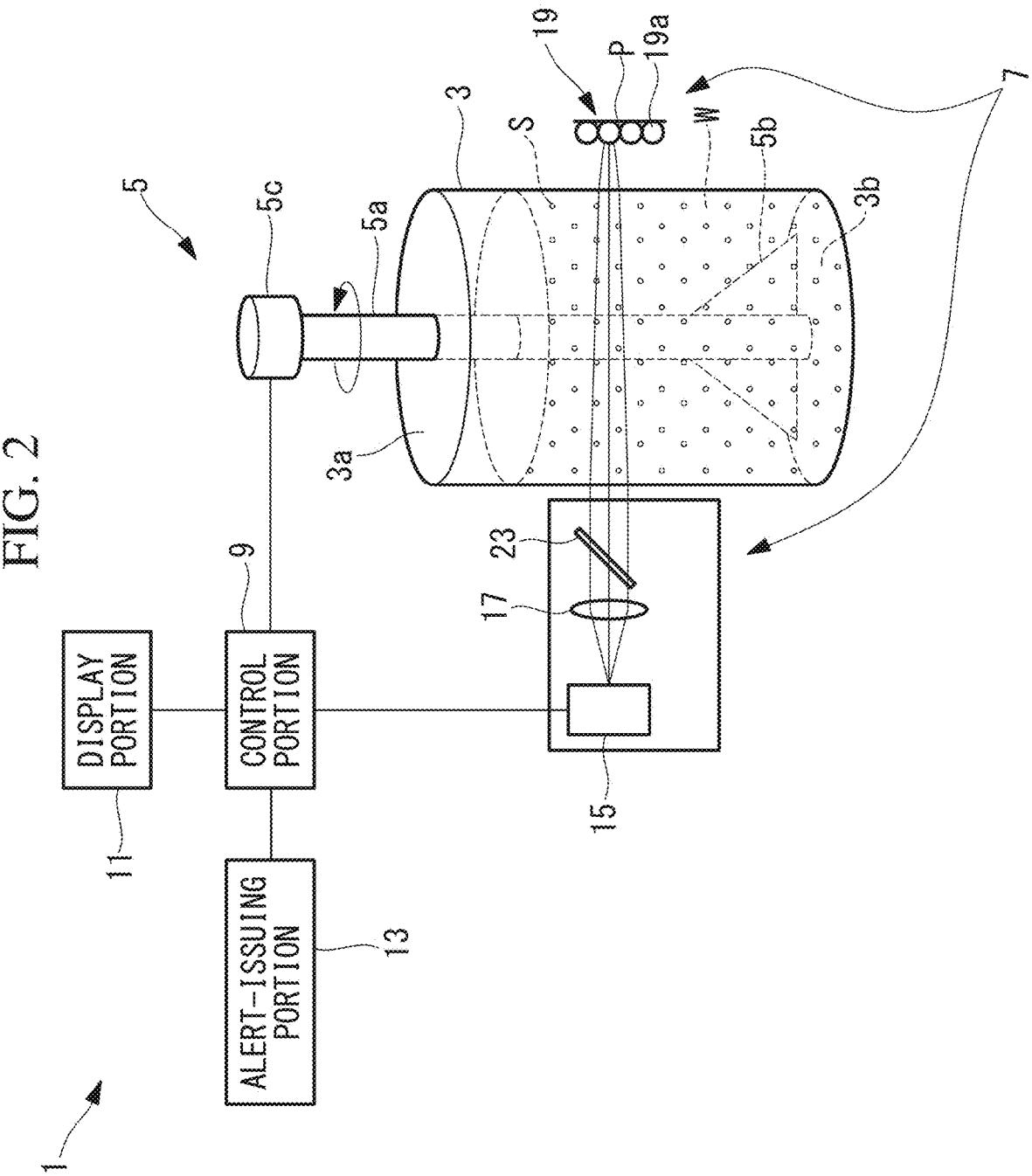
FIG. 2 is a schematic configuration diagram for explaining the configuration of the culture-medium-monitoring apparatus in FIG. 1.

As shown in FIGS. 1 and 2, a culture-medium-monitoring apparatus 1 according to this embodiment includes, for example: a stirrer 5 that stirs a culturing liquid (culture medium) W accommodated in a culturing vessel (vessel) 3 together with cells S; an optical measurement unit 7 that measures the intensity of a light beam passing through the culturing liquid W; a control portion 9 that controls the stirrer 5 and the optical measurement unit 7 and that determines the state of the culturing liquid W; a display portion 11 that displays various types of information; and an alert-issuing portion (notifying portion) 13 that issues a notification indicating said information to a user.

The culturing vessel 3 is, for example, a vessel for a bioreactor or the like for performing suspension culturing of the cells S. The culturing vessel 3 is a closed-bottom cylindrical vessel in which a top surface 3a is closed. The culturing vessel 3 is formed of an optically transparent material and is capable of allowing the illumination light beam generated by the optical measurement unit 7 to pass therethrough. Phenol red or the like is added to the culturing liquid W for determining the state of the culturing liquid W.

The stirrer 5 includes: an stirring rod 5a that is inserted into the culturing vessel 3 via the top surface 3a of the culturing vessel 3; a plurality of stirring blades 5b provided on the stirring rod 5a; and a motor 5c that rotates the stirring rod 5a about a longitudinal axis.

The optical measurement unit 7 includes: an illumination light source (illuminating portion) 15 that generates the illumination light beam to be radiated onto the culturing liquid W in the culturing vessel 3; a retroreflective member 19 that returns, toward the illumination light source 15, the illumination light beam that has passed through the culturing liquid W; a half mirror 23 that splits the path off of the illumination light beam returned by the retroreflective member 19; and a light detector (light-detecting portion) 25, such as a photomultiplier tube, that detects the intensity of the illumination light beam that has been split off by the half mirror 23. In FIGS. 1 and 2, reference sign 17 indicates a collecting lens (illuminating portion) that collects the illumination light beam emitted from the illumination light source 15 to radiate the illumination light beam onto the culturing liquid W, and reference sign 22 indicates a collecting lens that collects the illumination light beam that has been split off by the half mirror 23 to make the illumination light beam enter the light detector 25.

The illumination light source 15 is an LED (Light Emitting Diode) that generates, for example, a 560-nm monochromatic light beam, as the illumination light beam. The illumination light source 15 radiates the illumination light beam toward the culturing liquid W in the culturing vessel 3 from outside the culturing vessel 3.

The collecting lens 17 is disposed between the illumination light source 15 and the culturing vessel 3.

In this embodiment, an illuminating portion is formed from the illumination light source 15 and the collecting lens 17. The collecting lens 17 may be omitted in the case in which a light source from which a coherent collimated light beam is emitted, such as a laser light source, is employed as the illumination light source.

The retroreflective member 19 is disposed outside the culturing vessel 3 so as to substantially face the illumination light source 15 and the collecting lens 17 in a state in which the culturing vessel 3 is sandwiched between the retroreflective member 19, and the illumination light source 15 and the collecting lens 17 in a direction intersecting the depth direction. The illumination light source 15, the collecting lens 17, and the retroreflective member 19 are disposed at positions at which the illumination light beam traveling inside the culturing vessel 3 does not interfere with the stirring rod 5a and the stirring blades 5b of the stirrer 5.

In order to increase the sensitivity to changes in the transmittance of the illumination light beam that passes through the culturing liquid W, it is advantageous for the illumination light beam that passes through the culturing liquid W to have a greater optical-path length; therefore, it is desirable that the illumination light source 15, the collecting lens 17, and the retroreflective member 19 be disposed, with respect to the stirring rod 5a and the stirring blades 5b, at positions at which the optical-path length becomes greater, in other words, so that the illumination light beam passes through a position that is as close to the stirring rod 5a as possible without interfering with the stirring rod 5a.

Figure 3:
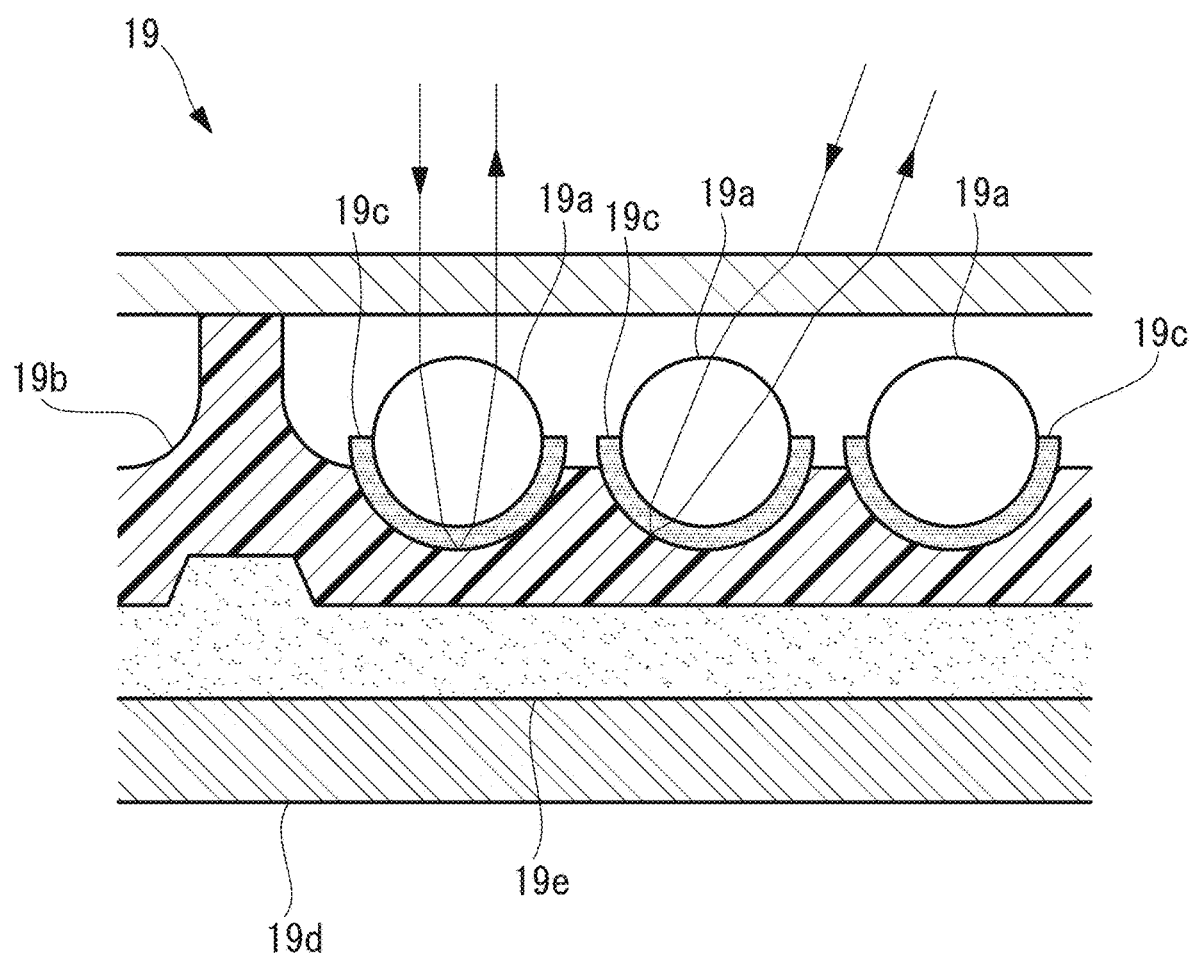
FIG. 3 shows a configuration example of a retroreflective member of the culture-medium-monitoring apparatus in FIG. 1.

As shown in, FIGS. 1 and 3, the retroreflective member 19 has, for example, an array in which numerous microreflective elements 19a are arrayed along a surface P. The surface P is a surface intersecting the optical axis of the illumination light beam that has passed through the culturing vessel 3. The surface P may be a flat surface or a curved surface. As shown in FIG. 1, the surface P may be, for example, a curved surface that has a constant curvature and that is curved in one direction or a curved surface that is curved in multiple directions.

The reflective elements 19a are, for example, prisms or spherical glass beads. The reflective elements 19a are disposed so that reflective films 19c are interposed between a surface of the base member 19b and the reflective elements 19a, and are arrayed along the surface of the base member 19b. In the figure, reference sign 19d is a release film, and reference sign 19e is an adhesive with which the base member 19b and the release film 19d are adhered to each other.

The illumination light beam that has entered the reflective elements 19a is reflected by the reflective films 19c and exits from the reflective elements 19a in the opposite direction from the entry direction. Because the reflective elements 19a are minute, there is almost no displacement between the entry path and the exit path of the illumination light beam. Therefore, the illumination light beam reflected by the retroreflective member 19 returns along the same path as the path of the illumination light beam entering the retroreflective member 19. In other words, the illumination light beam travels along the same path in a back-and-forth manner between the interior of the culturing vessel 3 and the retroreflective member 19.

It is possible to arbitrarily set the position and the angle at which the retroreflective member 19 is disposed. The retroreflective member 19 may be attached to, for example, a stand, a wall, or the like (not shown), or the retroreflective member 19 may be attached to a side surface of the culturing vessel 3. The installation position and the installation angle of the retroreflective member 19 may be an arbitrary position, distance, and angle so long as it is possible to receive the illumination light beam that has passed through the culturing vessel 3 from the illumination light source 15.

The half mirror 23 is disposed in the path of the illumination light beam between the culturing vessel 3, and the illumination light source 15 and the collecting lens 17. The half mirror 23 is capable of guiding the illumination light beam to the light detector 25 by reflecting, toward the light detector 25, the illumination light beam that has passed through the culturing vessel 3 again from the retroreflective member 19 side.

The light detector 25 outputs a detection signal in accordance with the intensity of the detected illumination light beam.

The control portion 9 is, for example, a PC (Personal Computer). The control portion 9 includes, for example, an interface circuit, a storage portion such as a hard disk drive, a CPU (Central Processing Unit), and a RAM (Random Access Memory) (none of these components are shown).

The interface circuit includes a control board for controlling the stirrer 5 and the optical measurement unit 7, and a signal processing board that receives the detection signal output from the light detector 25 and that converts the received detection signal to a light-intensity signal (none of these components are shown).

The storage portion stores various types of programs that are executed by the CPU.

The CPU loads the various types of programs stored in the storage portion, and executes the following functions. Specifically, the control portion 9 controls the ON/OFF state of the illumination light source 15, driving of the motor 5c of the stirrer 5, issuing of a notification to the user by means of the alert-issuing portion 13, and so forth. The control portion 9 causes the illumination light beam to be radiated onto the culturing liquid W in the culturing vessel 3 from the illumination light source 15 at prescribed time intervals, and causes the light detector 25 to detect the intensity of the illumination light beam that has passed through the culturing liquid W. Then, the control portion 9 determines the state of the culturing liquid W on the basis of changes over time in the intensity of the illumination light beam that has passed through the culturing liquid W.

For example, the control portion 9 stores an initial intensity (prescribed threshold) of the illumination light beam that is made to pass through the culturing liquid W before starting to culture the cells S. Then, the control portion 9 compares, with the initial intensity, the intensity of the illumination light beam that is made to pass through the culturing liquid W while culturing the cells S. Then, in the case in which the intensity of the illumination light beam has fallen below the initial intensity by a prescribed amount or more, the control portion 9 issues a notification to the user, by means of the alert-issuing portion 13, indicating that the timing for replacing the culture medium has arrived.

Next, the operation of the culture-medium-monitoring apparatus 1 according to this embodiment will be described.

In the case in which the state of the culturing liquid W is monitored by means of the culture-medium-monitoring apparatus 1 having the above-described configuration while culturing the cells S, first, the culturing liquid W in the culturing vessel 3 is stirred as a result of the control portion 9 causing the stirrer 5 to be driven. By doing so, the cells S are cultured while being suspended in the culturing liquid W.

Next, as a result of the control portion 9 causing the illumination light source 15 to be turned on at the prescribed time intervals, the 560-nm illumination light beam is radiated onto the culturing liquid W in the culturing vessel 3. The illumination light beam that has passed through the culturing liquid W is reflected by the retroreflective member 19, and returns toward the culturing vessel 3 by passing along the same path as the entry path to the retroreflective member 19. Then, after passing through the culturing liquid W in the culturing vessel 3 again, the illumination light beam is reflected by the half mirror 23 and enters the light detector 25. By doing so, the intensity of the illumination light beam that has passed through the culturing liquid W is detected by the light detector 25.

As a result of the illumination light source 15 and the light detector 25 being controlled by the control portion 9, the intensity of the illumination light beam that has passed through the culturing liquid W is repeatedly detected at the prescribed time intervals, and thus, the changes over time in the intensity of the illumination light beam are monitored. Then, in the case in which the intensity of the illumination light beam has fallen below the initial intensity by the prescribed amount or more, the control portion 9 causes the alert-issuing portion 13 to issue a notification to the user, indicating that the timing for replacing the culture medium has arrived.

Specifically, in the optical measurement unit 7, when the illumination light beam coming from the illumination light source 15 is radiated onto the culturing liquid W in the culturing vessel 3 via the collecting lens 17, the illumination light beam that has passed through the culturing liquid W is reflected by the retroreflective member 19, which is disposed on the opposite side from the illumination light source 15 and the collecting lens 17 with the culturing vessel 3 sandwiched between the retroreflective member 19, and the illumination light source 15 and the collecting lens 17, and the illumination light beam reflected by the retroreflective member 19 is detected by the light detector 25 after passing through the culturing liquid W in the culturing vessel 3 again. Then, the control portion 9 determines the state of the culturing liquid W in the culturing vessel 3 on the basis of the changes over time in the intensity of the illumination light beam repeatedly detected at the prescribed time intervals.

In this case, the retroreflective member 19 is constituted of the array in which the plurality of micro-reflective elements are arrayed, thus reflecting the illumination light beam that has entered the retroreflective member 19 in completely the same direction as the entry direction. In other words, regardless of the material, the shape, the size, and so forth of the culturing vessel 3, it is possible to return the illumination light beam that has passed through the culturing liquid W in the culturing vessel 3 in the opposite direction along the same optical path as the entry optical path by means of the retroreflective member 19. By doing so, it is possible to reliably detect the intensity of the illumination light beam that has passed through the culturing liquid W by means of the light detector 25.

Therefore, with the culture-medium-monitoring apparatus 1 according to this embodiment, it is possible to stably monitor the culturing liquid W on the basis of the state of the culturing liquid W determined by the control portion 9 even if a wide variety of culturing vessels 3 are employed. It is possible to prompt the user to replace the culture medium at an appropriate timing by means of the control portion 9 via the alert-issuing portion 13 regardless of the material, the shape, the size, and so forth of the culturing vessel 3.

In this embodiment, the state of the culturing liquid W is determined by directly employing values of the intensity of the illumination light beam repeatedly detected by the light detector 25 at the prescribed time intervals. Alternatively, the intensity of the illumination light beam may be measured in advance in a state in which the culturing liquid W is not in the culturing vessel 3, the absorbance of the culturing liquid W may be calculated from the intensity of the illumination light beam repeatedly detected at the prescribed time intervals in the state in which the culturing liquid W is in the culturing vessel 3, and the state of the culturing liquid W may be determined by using the values of the calculated absorbance. As indicated in modifications, described later, changes over time in the intensity of illumination light beam at three wavelengths may be converted to the absorbance of the culturing liquid W, and the state of the culturing liquid W may be determined by using the pH value of the culturing liquid calculated from the absorbance.

Second Embodiment

Next, a culture-medium-monitoring apparatus according to a second embodiment of the present invention will be described.

Figure 4:
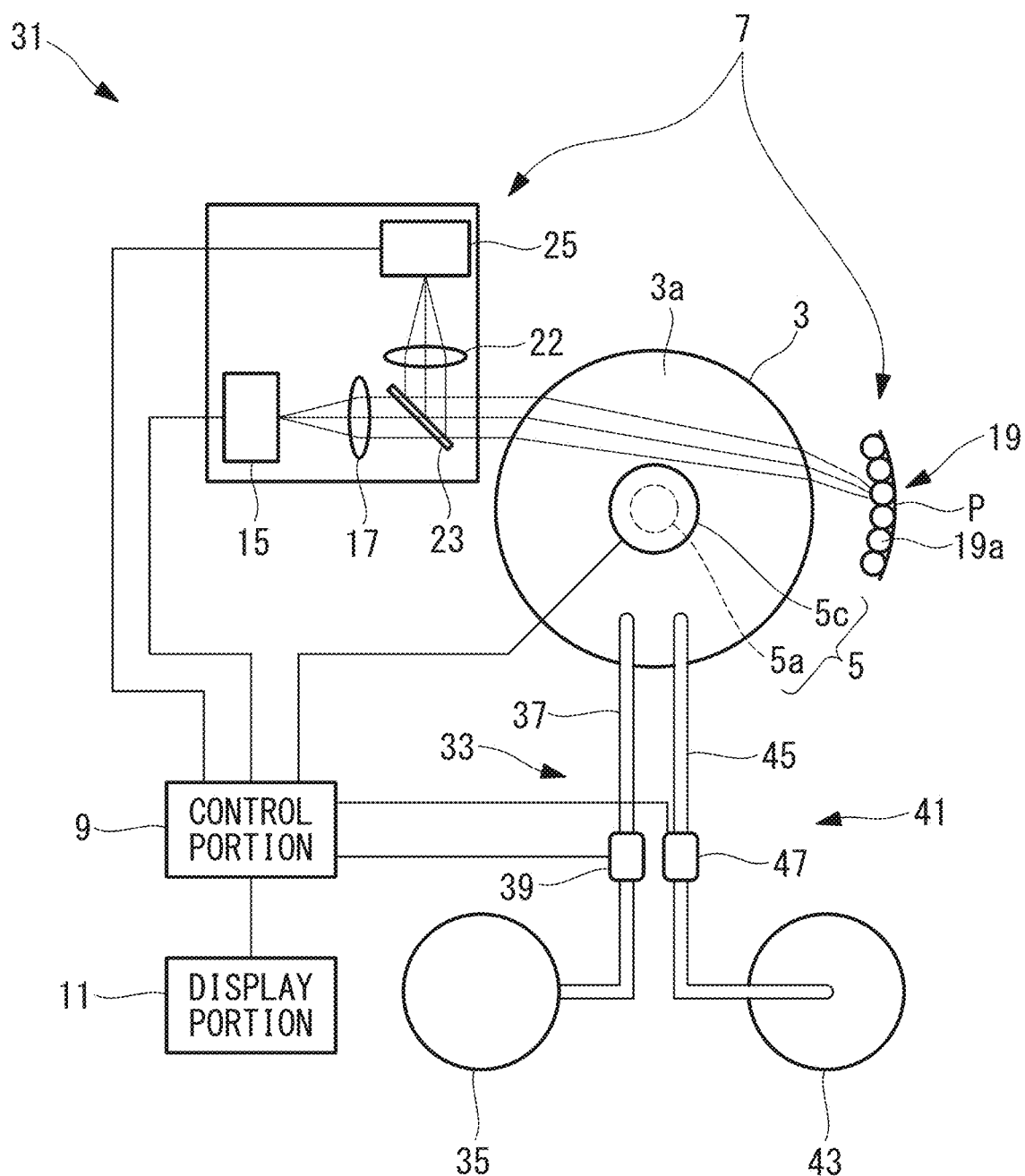
FIG. 4 is a schematic configuration diagram showing, from above, a culture-medium-monitoring apparatus according to a second embodiment of the present invention.
Figure 5:
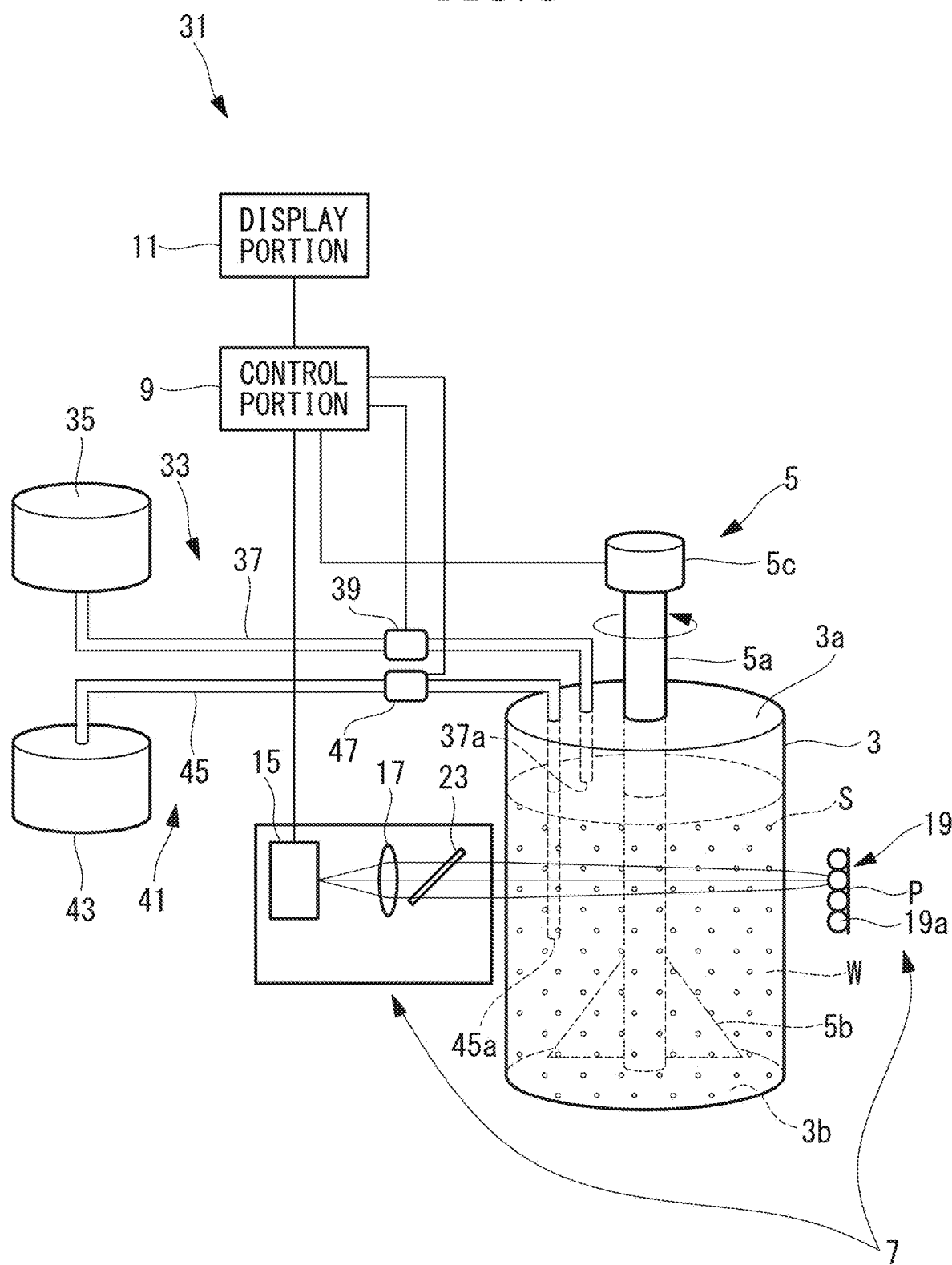
FIG. 5 is a schematic configuration diagram for explaining the configuration of the culture-medium-monitoring apparatus in FIG. 4.

As shown in FIGS. 4 and 5, a culture-medium-monitoring apparatus 31 according to this embodiment differs from the first embodiment, for example, in that a culture-medium-supplying portion 33 that supplies the culturing liquid W to the culturing vessel 3 and a culture-medium-discharging portion 41 that discharges the culturing liquid W from the culturing vessel 3 are included, and that the control portion 9 controls the culture-medium-supplying portion 33 and the culture-medium-discharging portion 41.

In the following, portions having the same configurations as those of the culture-medium-monitoring apparatus 1 according to the first embodiment will be given the same reference signs, and descriptions thereof will be omitted.

The culture-medium-supplying portion 33 includes: a culture-medium-supplying tank 35 that holds a new culturing liquid W; a culture-medium-supplying pipe 37 that forms a flow channel for feeding the culturing liquid W to the culturing vessel 3 from the culture-medium-supplying tank 35; and a culture-medium-supplying pump 39 that feeds the culturing liquid W in the culture-medium-supplying tank 35 to the culturing vessel 3 via the culture-medium-supplying pipe 37.

As shown in FIG. 5, the culture-medium-supplying pipe 37 is inserted into the culturing vessel 3 at a position at which the culture-medium-supplying pipe 37 does not block the path of the illumination light beam and does not interfere with the stirring blades 5b. It is preferable that, in the culture-medium-supplying pipe 37, a supply port 37a from which the culturing liquid W is supplied be disposed, for example, in the vicinity of a liquid surface of the culturing liquid W accommodated in the culturing vessel 3.

The culture-medium-discharging portion 41 includes: a culture-medium-discharging tank 43 that collects the culturing liquid W discharged from the culturing vessel 3; a culture-medium-discharging pipe 45 that forms a flow channel for feeding the culturing liquid W to the culture-medium-discharging tank 43 from the culturing vessel 3; and a culture-medium-discharging pump 47 that feeds the culturing liquid W in the culturing vessel 3 to the culture-medium-discharging tank 43 via the culture-medium-discharging pipe 45.

As shown in FIG. 5, the culture-medium-discharging pipe 45 is inserted into the culturing vessel 3 at a position at which the culture-medium-discharging pipe 45 does not block the path of the illumination light beam and does not interfere with the stirring blades 5b. It is preferable that, in the culture-medium-discharging pipe 45, a suction port 45a from which the culturing liquid W is sucked out be disposed, for example, in the vicinity of an intermediate depth in the culturing liquid W accommodated in the culturing vessel 3.

The culture-medium-discharging pump 47 is capable of discharging the culturing liquid W in the culturing vessel 3, for example, at a speed that does not cause the cells S in the culturing liquid W to be sucked out, that is, for example, a speed at which the culturing liquid W is sucked out without stirring the culturing liquid W.

The control portion 9 performs ON/OFF switching of the supply of the culturing liquid W to the culturing vessel 3 from the culture-medium-supplying tank 35 by controlling driving of the culture-medium-supplying pump 39. The control portion 9 performs ON/OFF switching of the discharge of the culturing liquid W to the culture-medium-discharging tank 43 from the culturing vessel 3 by controlling driving of the culture-medium-discharging pump 47.

In this embodiment, the control portion 9 determines that culture medium replacement is necessary in the case in which the intensity of the illumination light beam detected by the light detector 25 has fallen below the initial intensity by the prescribed amount or more. When the control portion 9 has determined that culture medium replacement is necessary, first, the control portion 9 causes the driving of the motor 5c of the stirrer 5 to be stopped, thus stopping the stirring of the culturing liquid W. Next, the control portion 9 causes the culture-medium-discharging pump 47 to be driven to discharge a portion of the culturing liquid W to the culture-medium-discharging tank 43 from the culturing vessel 3 via the culture-medium-discharging pipe 45, and causes the culture-medium-supplying pump 39 to be driven to supply the new culturing liquid W to the culturing vessel 3 from the culture-medium-supplying tank 35 via the culture-medium-supplying pipe 37.

Next, the operation of the culture-medium-monitoring apparatus 31 according to this embodiment will be described. In the case in which the state of the culturing liquid W is monitored by means of the culture-medium-monitoring apparatus 31 having the above-described configuration while culturing the cells S, as with the first embodiment, the intensity of the illumination light beam that has passed through the culturing liquid W is repeatedly detected at the prescribed time intervals as a result of the control portion 9 controlling the optical measurement unit 7, and the state of the culturing liquid W is determined on the basis of the changes over time in the detected intensity of the illumination light beam.

When the intensity of the illumination light beam detected by the light detector 25 has fallen below the initial intensity by the prescribed amount or more, first, the control portion 9 causes the driving of the motor 5c of the stirrer 5 to be stopped, thus stopping the stirring of the culturing liquid W. Then, about half of the culturing liquid W in the culturing vessel 3 is discharged as a result of the control portion 9 causing the culture-medium-discharging pump 47 to be driven, and the discharged culturing liquid W is collected in the culture-medium-discharging tank 43.

Next, as a result of the control portion 9 causing the culture-medium-supplying pump 39 to be driven, the new culturing liquid W is replenished in the culturing vessel 3 from the culture-medium-supplying tank 35. By doing so, the culturing liquid W in the culturing vessel 3 is replaced.

After replacing the culturing liquid W, monitoring of the state of the culturing liquid W is continued as a result of the control portion 9 causing the illumination light beam to be radiated onto the culturing liquid W at the prescribed time intervals again, and causing the intensity of the illumination light beam that has passed through the culturing liquid W to be measured.

Specifically, it is possible to replace the culturing liquid W in the culturing vessel 3 as a result of discharging a portion of the culturing liquid W in the culturing vessel 3 by means of the culture-medium-discharging portion 41 while supplying the new culturing liquid W to the culturing vessel 3 by means of the culture-medium-supplying portion 33. Whether the culturing liquid W in the culturing vessel 3 has deteriorated, that is, whether the timing for replacing the culture medium has arrived, is ascertained by means of the control portion 9 on the basis of the changes over time in the intensity of the illumination light beam detected by the light detector 25.

Therefore, with the culture-medium-monitoring apparatus 31 according to this embodiment, as a result of the control portion 9 controlling the culture-medium-supplying portion 33 and the culture-medium-discharging portion 41 on the basis of the changes over time in the intensity of the illumination light beam, it is possible to replace the culture medium at an accurate timing without requiring time and effort on the part of the user.

As a result of stopping the stirring of the culturing liquid W when replacing the culture medium, the cells S in the culturing liquid W move to a lower portion of the culturing vessel 3 due to gravity. As a result of disposing the suction port 45a of the culture-medium-discharging pipe 45 in the vicinity of an intermediate depth in the culturing liquid W in the culturing vessel 3, it is possible to prevent the cells S in the culturing liquid W from being discharged together with the culturing liquid W discharged by means of the culture-medium-discharging portion 41.

This embodiment can be modified to the following configuration.

Figure 6:
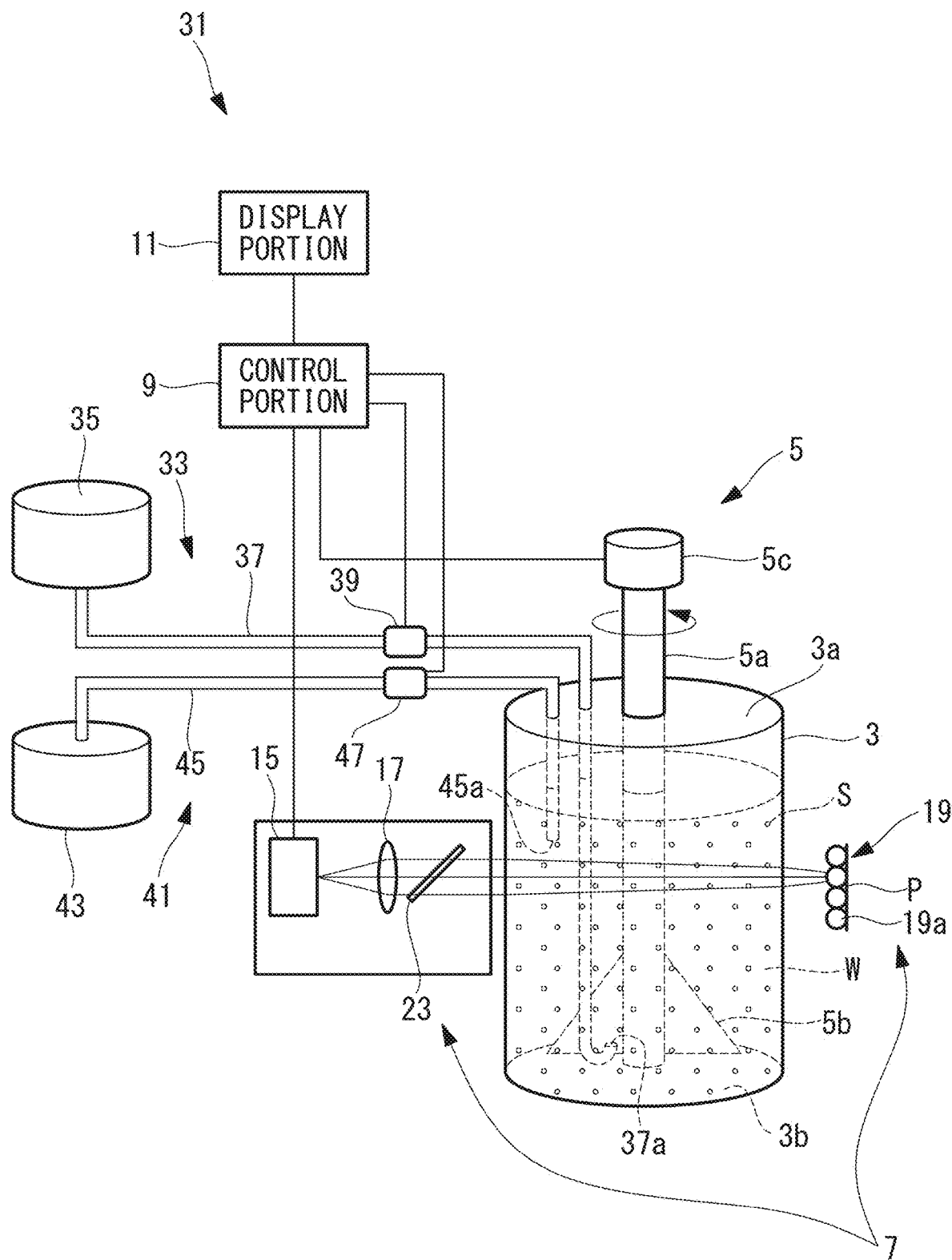
FIG. 6 is a schematic configuration diagram showing, from above, a culture-medium-monitoring apparatus according to a modification of the second embodiment of the present invention.

Although the supply port 37a of the culture-medium-supplying pipe 37 is disposed in the vicinity of the liquid surface of the culturing liquid W in the culturing vessel 3 in this embodiment, alternatively, as shown in FIG. 6, for example, the culture-medium-supplying pipe 37 may be extended to a lower portion of the culturing vessel 3, and the supply port 37a may be disposed in the vicinity of a bottom surface 3b of the culturing vessel 3.

In this case, it is desirable that the supply port 37a of the culture-medium-supplying pipe 37 be formed in an upward U-shape that is folded back toward the top surface 3a in the vicinity of the bottom surface 3b of the culturing vessel 3. It is preferable that the suction port 45a of the culture-medium-discharging pipe 45 be disposed at a position that is slightly lower than the liquid surface of the culturing liquid W.

When replacing the culture medium, the control portion 9 causes the driving of the motor 5c of the stirrer 5 to be stopped, thus stopping the stirring of the culturing liquid W. As a result of controlling the culture-medium-discharging pump 47 of the culture-medium-discharging portion 41 and the culture-medium-supplying pump 39 of the culture-medium-supplying portion 33, the control portion 9 simultaneously performs discharging of the culturing liquid W from the culturing vessel 3 and supplying of the culturing liquid W to the culturing vessel 3.

Because the deteriorated culturing liquid W that needs to be replaced has a lower specific gravity as compared with that of the new culturing liquid W, the deteriorated culturing liquid W is separated into an upper portion of the culturing vessel 3, and the new culturing liquid W is separated into the lower portion of the culturing vessel 3. When replacing the culture medium, as a result of stopping the stirring of the culturing liquid W, the cells S in the culturing liquid W move to the lower portion of the culturing vessel 3 due to gravity.

Therefore, with the culture-medium-monitoring apparatus 31 according to this modification, as a result of disposing the suction port 45a of the culture-medium-discharging pipe 45 near the liquid surface of the culturing liquid W, it is possible to reduce the risk of the cells S being discharged together with the culturing liquid W. As a result of simultaneously discharging and supplying the culturing liquid W, it is possible to reduce the time required to replace the culture medium.

Third Embodiment

Next, a culture-medium-monitoring apparatus according to a third embodiment of the present invention will be described.

Figure 7:
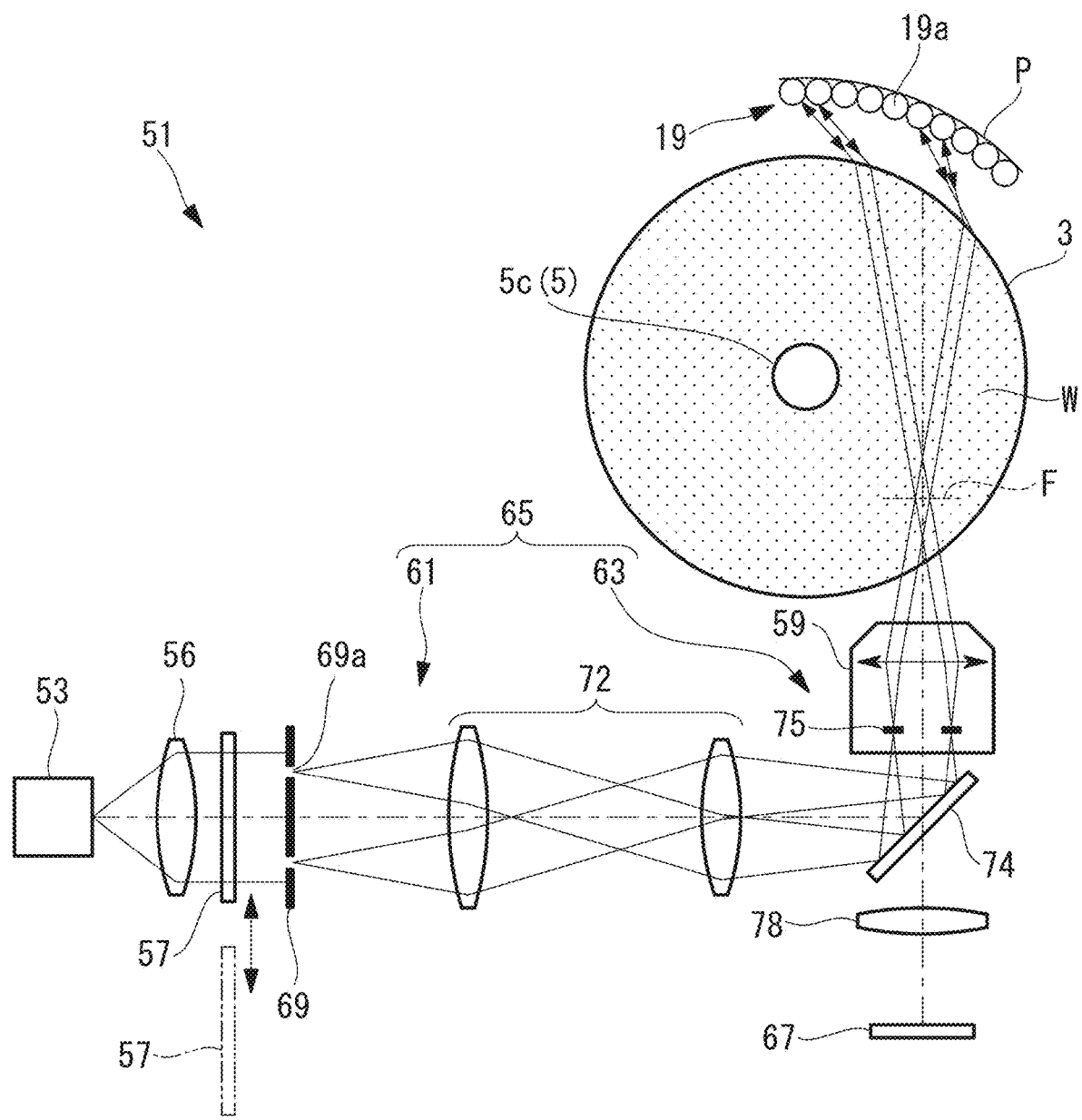
FIG. 7 is a schematic configuration diagram showing, from above, a culture-medium-monitoring apparatus according to a third embodiment of the present invention.

As shown in FIG. 7, a culture-medium-monitoring apparatus 51 according to this embodiment differs from the first and second embodiments, for example, in that a phase contrast optical system 65 is provided, the phase contrast optical system 65 being formed from an illumination optical system 61 that illuminates the cells S suspended in the culturing liquid W to generate a phase contrast image of the cells S and a detection optical system 63 that causes the phase contrast image of the cells S, which are suspended in the culturing liquid W and are irradiated with the illumination light beam, to be formed on the light-detecting portion. Although the culture-medium-monitoring apparatus 51 includes the control portion 9, the display portion 11, and the alert-issuing portion 13, in FIG. 7, the control portion 9, the display portion 11, and the alert-issuing portion 13 are not shown.

In the following, portions having the same configurations as those of the culture-medium-monitoring apparatuses 1 and 31 according to the first and second embodiments will be given the same reference signs, and descriptions thereof will be omitted.

In this embodiment, a white light source 53, for example, a halogen light source or the like, is employed as the illumination light source instead of the illumination light source 15 such as an LED. A lens 56 that converts the light beam emitted from the white light source 53 to collimated light beam and a bandpass filter 57 that extracts a specific wavelength from the light beam converted to the collimated light beam by the lens 56 are employed. The bandpass filter 57 is provided so as to be insertable into the path of the illumination light beam and retractable therefrom.

In this embodiment, the optical measurement unit 7 includes: an objective lens 59 that is disposed at a side of the culturing vessel 3; the illumination optical system 61 that radiates the illumination light beam coming from the white light source 53 into the interior of the culturing vessel 3 via the objective lens 59 from outside the culturing vessel 3; the retroreflective member 19; and the detection optical system 63.

In this embodiment, an image-acquisition device 67, for example, a CCD image sensor, a CMOS image sensor, or the like, is employed as the light-detecting portion instead of the light detector 25 such as a photomultiplier tube or the like. The image-acquisition device 67 acquires an image formed by the detection optical system 63, thus acquiring a phase contrast image of the cells S.

The objective lens 59 is disposed so that the optical axis thereof is disposed in a substantially horizontal direction, and is disposed so as to face the culturing vessel 3. A focal plane F of the objective lens 59 is disposed inside the culturing vessel 3.

The illumination optical system 61 includes: the lens 56; the objective lens 59; an aperture 69 having a ring slit 69*a*, which is an annular opening; a relay optical system 72; and a half mirror 74. In other words, the objective lens 59 serves as part of the illumination optical system 61.

The ring slit 69*a* of the aperture 69 is disposed at an optically conjugate position with respect to the pupil position of the objective lens 59. The illumination light beam that has been converted to collimated light beam by the lens 56 passes through only the ring slit 69*a* in the aperture 69. It is possible to adjust the position of the aperture 69 in a direction orthogonal to the optical axis of the illumination light beam entering the aperture 69.

The relay optical system 72 relays the illumination light beam that has passed through the ring slit 69*a*. The relay optical system 72 is formed from, for example, a pair of convex lenses.

The half mirror 74 reflects a portion of the illumination light beam that has been relayed thereto by the relay optical system 72 from the white light source 53, for example, about 50% of the illumination light beam that has been made incident on the half mirror 74, toward the objective lens 59, while allowing a portion of the illumination light beam that has entered from the objective lens 59 side, for example, about 50% of the illumination light beam that has been made incident on the half mirror 74, to pass therethrough.

The illumination light beam that has been reflected by the half mirror 74 enters the objective lens 59 along the optical axis of the objective lens 59, and is made to exit toward the culturing vessel 3 from the objective lens 59. In other words, the objective lens 59 also serves as part of the illumination optical system 61. The illumination light beam that has been made to exit the objective lens 59 travels across the interior of the culturing vessel 3 in a substantially horizontal direction after passing through a side wall of the culturing vessel 3, and is made to exit to outside the culturing vessel 3 after passing through the side wall of the culturing vessel 3 again. As a result of adjusting the position of the aperture 69, it is possible to change the position of the illumination light beam that enters the culturing vessel 3 from the objective lens 59 in a direction intersecting the optical axis of the illumination light beam.

The retroreflective member 19 is disposed so as to sandwich the culturing vessel 3 between the objective lens 59 and the retroreflective member 19 in a substantially horizontal direction.

The objective lens 59 and the retroreflective member 19 are disposed in a path of the illumination light beam between the objective lens 59 and the retroreflective member 19 at the position at which the stirring rod 5*a* and the stirring blades 5*b* of the stirrer 5 do not interfere with the illumination light beam.

The detection optical system 63 includes: the objective lens 59; a phase film 75 that is disposed at the pupil position of the objective lens 59; and an imaging lens 78 that causes the illumination light beam that has passed through the half mirror 23 from the objective lens 59 side to form an image on the image-acquisition device 67. In other words, the objective lens 59 also serves as part of the detection optical system 63.

The phase film 75 has a shape that corresponds to the shape of the ring slit 69*a* of the illumination optical system 61, that is, an annular shape. The phase film 75 shifts the phase of the illumination light beam that passes through the phase film 75. The phase film 75 is disposed at a conjugate position with respect to the ring slit 69*a* of the illumination optical system 61. The phase film 75 may be disposed at an optically conjugate position with respect to the pupil position of the objective lens 59.

The control portion 9 controls insertion and retraction of the bandpass filter 57 in addition to driving of the stirrer 5, the ON/OFF state of the white light source 53, measurement of the intensity of the illumination light beam by means of the image-acquisition device 67, and issuing of a notification about culture medium replacement by means of the alert-issuing portion 13.

Next, the operation of the culture-medium-monitoring apparatus 51 according to this embodiment will be described.

First, in the case in which phase contrast observation of the cells S is performed by means of the culture-medium-monitoring apparatus 51 having the above-described configuration, the control portion 9 causes the bandpass filter 57 to be retracted from the path of the illumination light beam, and, in this state, the illumination light beam is emitted from the white light source 53. The illumination light beam that has been emitted from the white light source 53 is radiated onto the culturing liquid W in the culturing vessel 3 from the illumination optical system 61 via the objective lens 59.

The illumination light beam that has been radiated onto the culturing liquid W is reflected by the retroreflective member 19 after passing through the culturing liquid W. Then, the illumination light beam is collected by the objective lens 59 after passing through the culturing liquid W in the culturing vessel 3 in the opposite direction. Therefore, the cells S suspended in the culturing liquid W in the culturing vessel 3 are illuminated by two types of illumination methods, namely, epi-illumination by means of the objective lens 59 and transmission illumination by means of the retroreflective member 19.

While passing through the culturing vessel 3 twice, a portion of the illumination light beam (signal light beam) passes through the transparent cells S suspended in the culturing liquid W and is refracted. After passing through the culturing liquid W in the culturing vessel 3 twice, the illumination light beam passes through the objective lens 59 and the half mirror 74, and forms an image on the image-acquisition device 67 by means of the imaging lens 78.

Here, the phase film 75 is disposed in the objective lens 59 at an optically conjugate position with respect to the ring slit 69*a*. The illumination light beam (refracted light beam) that has passed through the cells S in the culturing vessel 3 travels through a position that is different from that of the phase film 75 in the objective lens 59, and is made to exit the objective lens 59. On the other hand, the illumination light beam (straight traveling light beam) that did not pass through the cells S in the culturing vessel 3 is subjected to a phase shift as a result of passing through the phase film 75 in the objective lens 59, and is made to exit the objective lens

59. Therefore, an optical image of the cells S having a contrast due to interference between the refracted light beam and the straight traveling light beam is formed on the image-acquisition device 67. By doing so, a phase contrast image of the cells S is acquired by the image-acquisition device 67.

In this case, as described above, the retroreflective member 19 reflects the illumination light beam by means of the numerous micro-reflective elements 19a along the same path as the entry path. Therefore, the illumination light beam that has entered the culturing vessel 3 from the retroreflective member 19 illuminates the cells S in the culturing vessel 3 from the same direction and at the same angle regardless of the shape of the side wall of the culturing vessel 3 that is present between the retroreflective member 19 and the interior of the culturing vessel 3.

For example, in the case in which the side wall of the culturing vessel 3 has a curvature or unevenness, the side wall of the culturing vessel 3 exhibits a lens effect on the illumination light beam. However, as a result of the illumination light beam traveling through the side wall of the culturing vessel 3 along the same path in a back-and-forth manner, the lens effect is canceled out. In other words, the orientation and angle of the illumination light beam that enters the interior of the culturing vessel 3 from the retroreflective member 19 are not influenced by the side wall between the retroreflective member 19 and the interior of the culturing vessel 3.

Therefore, even if the culturing vessel 3 is made of a flexible material and the side wall of the culturing vessel 3 shows successive deformation, or even if the culturing vessel 3 is replaced with another culturing vessel 3 having a different shape and size, it is possible to stably illuminate the cells S in the culturing vessel 3 by means of the illumination light beam coming from the retroreflective member 19.

In the case in which the side wall of the culturing vessel 3 between the objective lens 59 and the interior of the culturing vessel 3 is flat, the illumination light beam that has entered the interior of the culturing vessel 3 from the objective lens 59 travels ahead along the optical axis of the objective lens 59. In other words, coaxial epi-illumination is realized.

On the other hand, in the case in which the side wall of the culturing vessel 3 between the objective lens 59 and the interior of the culturing vessel 3 has a curvature or unevenness, the optical axis of the illumination light beam that enters the interior of the culturing vessel 3 from the objective lens 59 becomes tilted with respect to the optical axis of the objective lens 59 due to the lens effect of the side wall of the culturing vessel 3. As a result, the position of the illumination light beam (straight traveling light beam) that has returned to the objective lens 59 from the retroreflective member 19 is sometimes displaced in a direction intersecting the optical axis from the position of the phase film 75. In this case, by adjusting the position of the illumination light beam radiated onto the culturing vessel 3 from the illumination optical system 61 by adjusting the position of the aperture 69, the illumination light beam (straight traveling light beam) returning to the objective lens 59 from the retroreflective member 19 passes through the phase film 75.

Next, in the case in which the state of the culturing liquid W is monitored by means of the culture-medium-monitoring apparatus 51 according to this embodiment, the control portion 9 causes the bandpass filter 57 to be inserted into the path of the illumination light beam, and, in this state, the illumination light beam is emitted from the white light source 53, and the illumination light beam is radiated onto the culturing liquid W in the culturing vessel 3.

Then, the intensity of the illumination light beam that has passed through the culturing liquid W in the culturing vessel 3 in a back-and-forth manner are measured by the image-acquisition device 67, and the control portion 9 monitors the changes over time in the intensity of the illumination light beam by using the sum of outputs of a plurality of pixels of the image-acquisition device 67. Then, in the case in which the intensity of the illumination light beam has fallen below the initial intensity by the prescribed amount or more, the control portion 9 prompts the user to replace the culture-medium via the alert-issuing portion 13.

As has been described above, with the culture-medium-monitoring apparatus 51 according to this embodiment, it is possible to acquire a high-resolution, high-contrast image of the cells S in the culturing liquid W by means of the phase contrast optical system 65 formed from the illumination optical system 61 and the detection optical system 63. As a result of the control portion 9 controlling, in a coordinated manner, insertion and retraction of the bandpass filter 57, driving of the stirring blades 5b, driving of the white light source 53 and the image-acquisition device 67, and measurement of the intensity of the illumination light beam, it is possible to perform phase contrast observation and monitoring of the state of the culturing liquid W completely automatically.

This embodiment can be modified to the following configuration.

For example, the configuration of the second embodiment may be applied to this embodiment, specifically, the configuration in which the culture-medium-supplying portion 33 and the culture-medium-discharging portion 41 are provided and the control portion 9 controls the culture-medium-supplying portion 33 and the culture-medium-discharging portion 41.

For example, the configuration according to the modification of the second embodiment may be applied to this embodiment, specifically, the configuration in which the supply port 37a of the culture-medium-supplying pipe 37 is disposed in the vicinity of the bottom surface 3b of the culturing vessel 3, the suction port 45a of the culture-medium-discharging pipe 45 is disposed near the liquid surface of the culturing liquid W, and the control portion 9 simultaneously performs discharging of the culturing liquid W by means of the culture-medium-discharging portion 41 and supplying of the culturing liquid W by means of the culture-medium-supplying portion 33.

Fourth Embodiment

Next, a culture-medium-monitoring apparatus according to a fourth embodiment, which serves as a Reference Example for the present invention, will be described.

Figure 8:
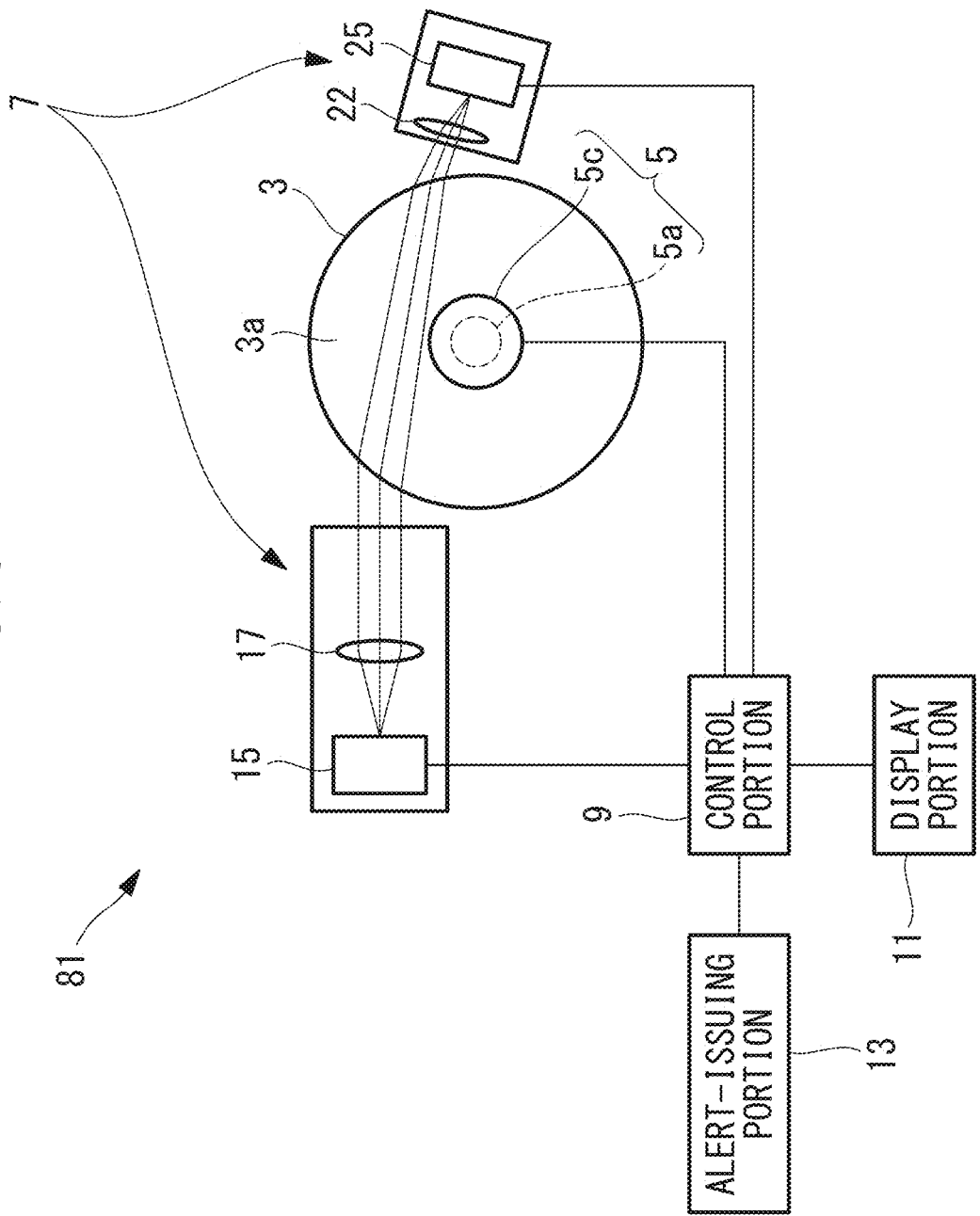
FIG. 8 is a schematic configuration diagram showing, from above, a culture-medium-monitoring apparatus according to a fourth embodiment of the present invention.
Figure 9:
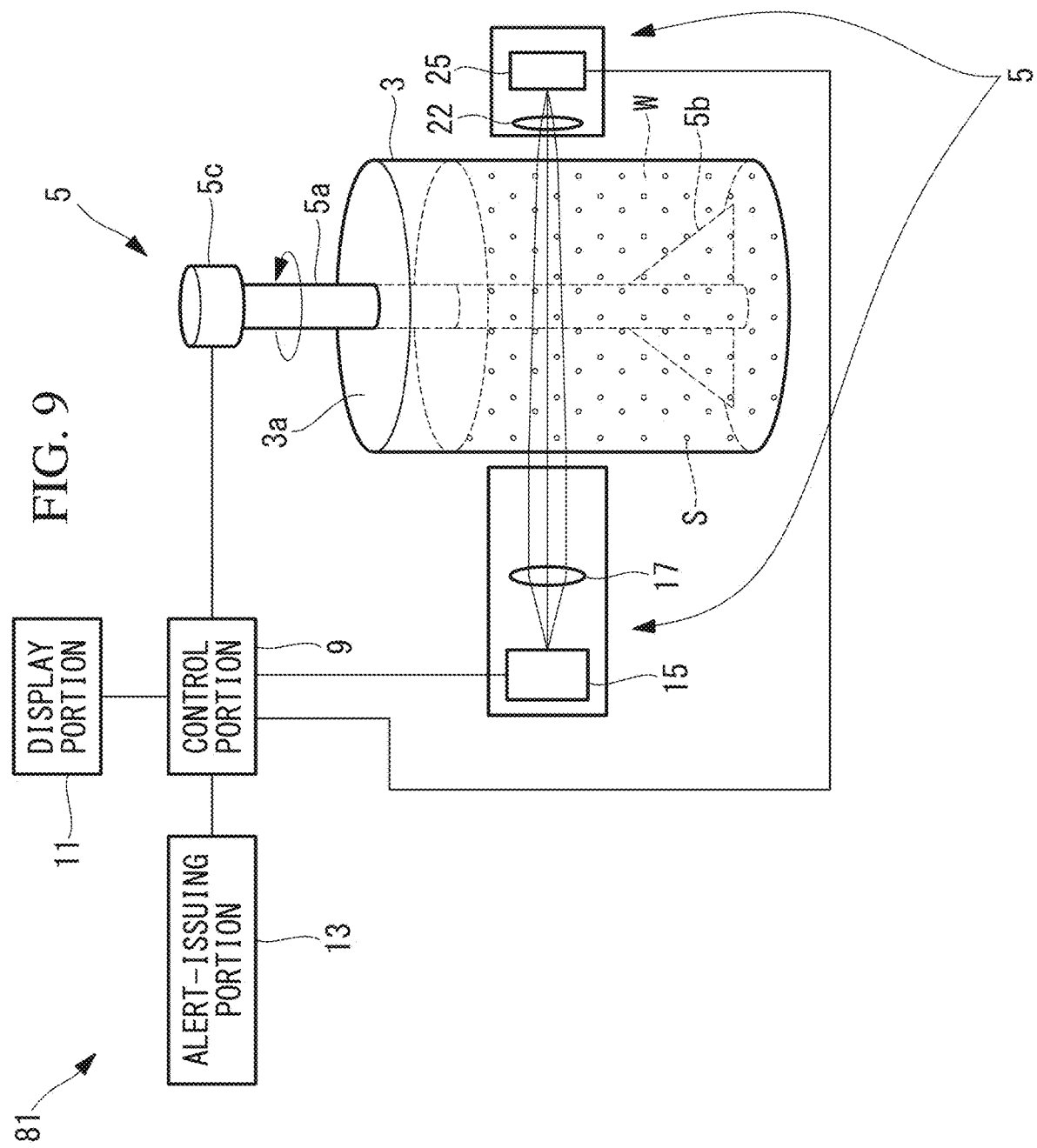
FIG. 9 is a schematic configuration diagram for explaining the configuration of the culture-medium-monitoring apparatus in FIG. 8.

As shown in FIGS. 8 and 9, a culture-medium-monitoring apparatus 81 according to this embodiment differs from the first to third embodiments, for example, in that the retroreflective member 19 is not included, and the light detector 25 is disposed at the position at which the retroreflective member 19 would be disposed.

In the following, portions having the same configurations as those of the culture-medium-monitoring apparatuses 1, 31, and 51 according to the first to third embodiments will be given the same reference signs, and descriptions thereof will be omitted.

The illumination light source 15 and the light detector 25 are both disposed outside the culturing vessel 3 so as to substantially face each other in a state in which the culturing vessel 3 is sandwiched therebetween in the direction intersecting the depth direction.

The light detector 25 detects the intensity of a transmission light beam (illumination light beam) that has exited to outside the culturing vessel 3 as a result of the illumination light beam being radiated onto the culturing liquid W and passing through the culturing liquid W.

In this embodiment, the illumination light beam that has passed through the culturing liquid W in the culturing vessel 3 from the illumination light source 15 is detected by the light detector 25 without returning to the culturing liquid W again. In the case in which the intensity of the illumination light beam that has been made to pass through the culturing liquid W is measured, the measurement is taken after waiting for the cells S in the culturing liquid W to move below the optical path of the optical measurement unit 7 due to gravity as a result of the stirring blades 5b being stopped by means of the control portion 9.

With the culture-medium-monitoring apparatus 81 according to this embodiment, as a result of measuring the intensity of the illumination light beam after the suspended cells S have moved below the path of the illumination light beam, it is possible to prevent the density of the suspended cells S in the culturing liquid W from influencing the measurement value of the intensity of the illumination light beam. As a result of eliminating the need for the retroreflective member 19, the configuration is simplified, and a cost reduction is achieved.

This embodiment can be modified to the following configuration.

Figure 10:
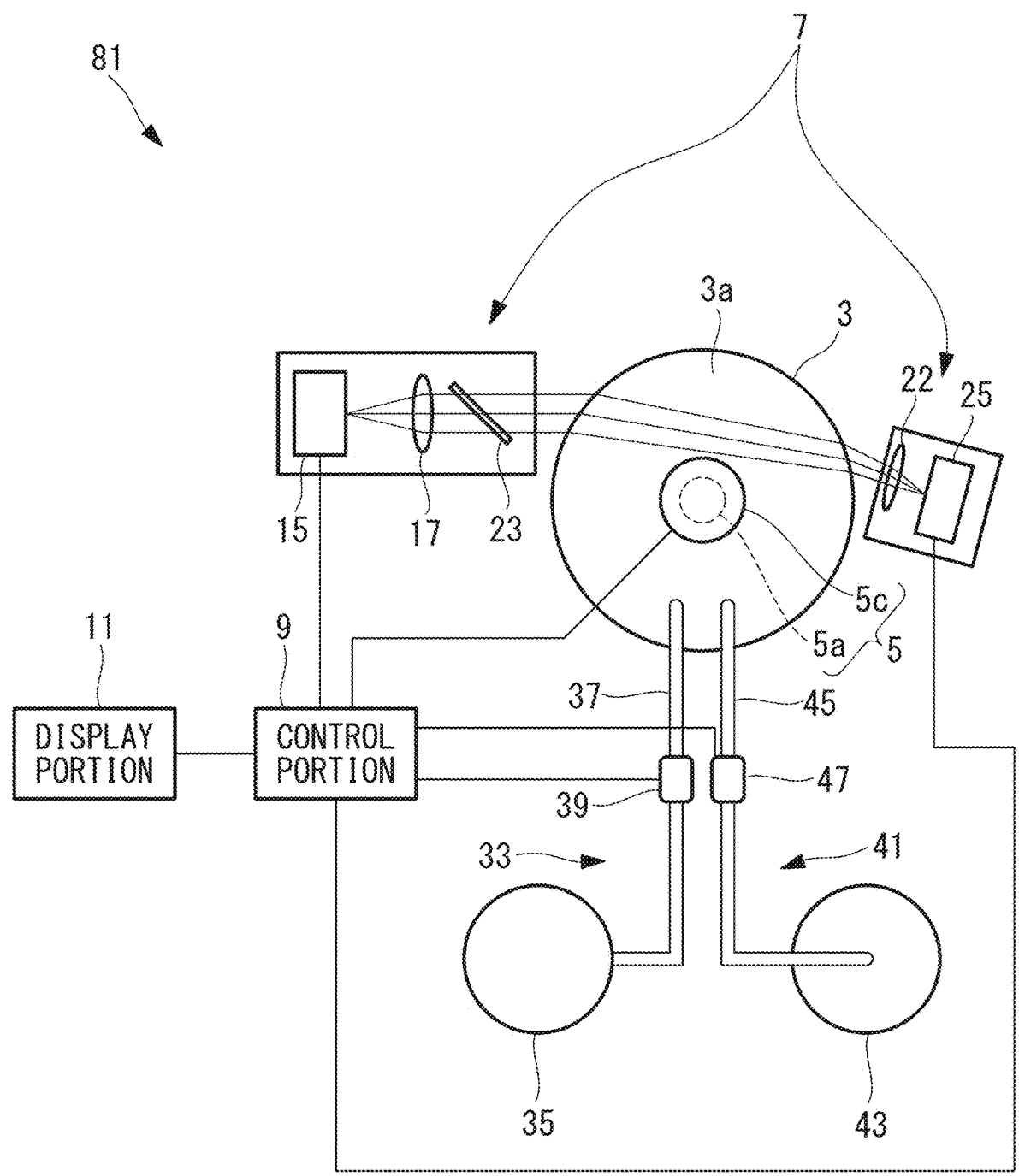
FIG. 10 is a schematic configuration diagram showing, from above, a culture-medium-monitoring apparatus according to a modification of the fourth embodiment of the present invention.
Figure 11:
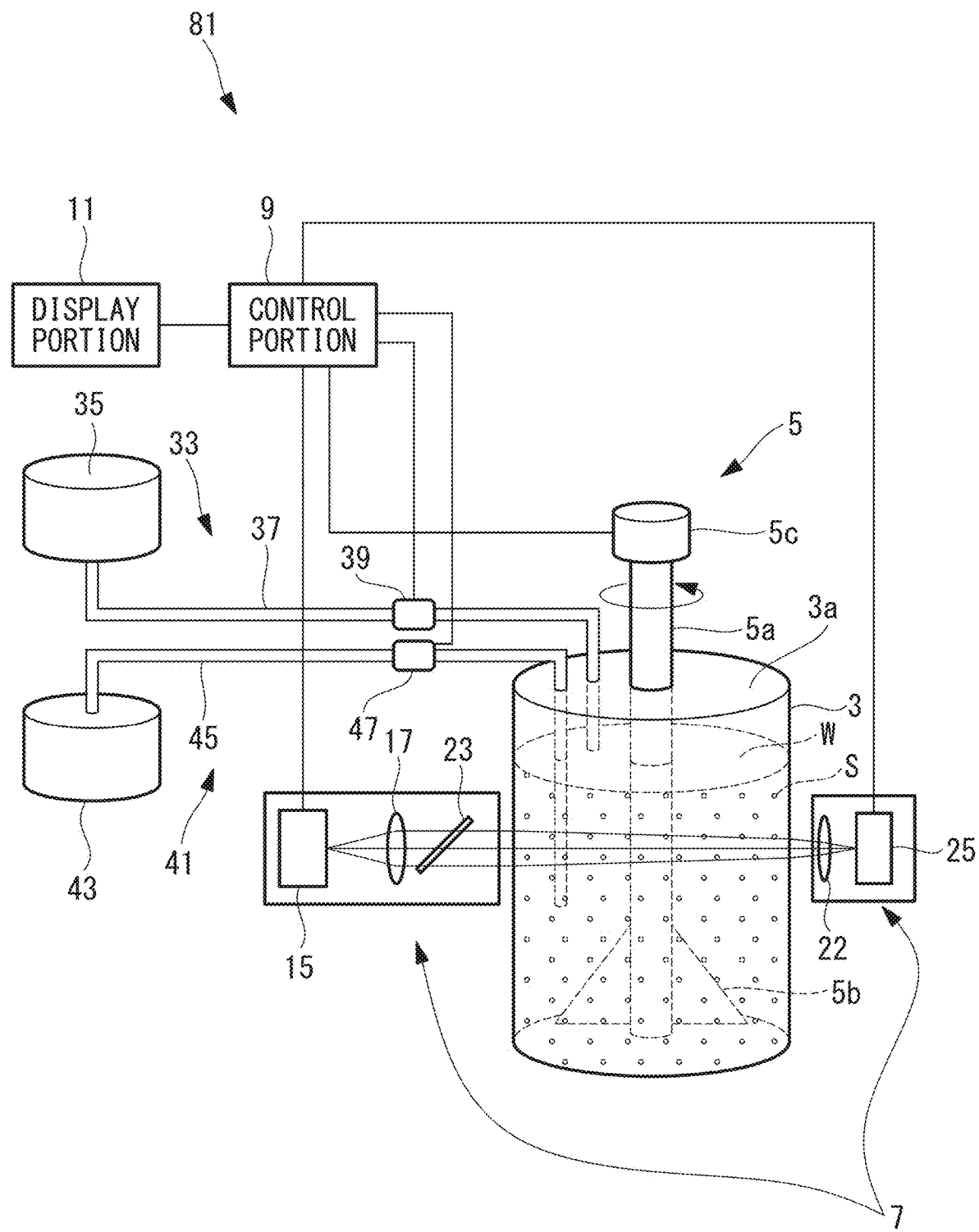
FIG. 11 is a schematic configuration diagram for explaining the configuration of the culture-medium-monitoring apparatus in FIG. 10.

As shown in FIGS. 10 and 11, for example, the configuration of the second embodiment may be applied to this embodiment, specifically, the configuration in which the culture-medium-supplying portion 33 and the culture-medium-discharging portion 41 are provided, and the control portion 9 controls the culture-medium-supplying portion 33 and the culture-medium-discharging portion 41.

With this configuration, to the extent that the retroreflective member 19 is not employed, the configuration is simplified, and a cost reduction is achieved.

For example, the configuration according to the modification of the second embodiment may be applied to this embodiment, specifically, the configuration in which the supply port 37a of the culture-medium-supplying pipe 37 is disposed in the vicinity of the bottom surface 3b of the culturing vessel 3, the suction port 45a of the culture-medium-discharging pipe 45 is disposed near the liquid surface of the culturing liquid W, and the control portion 9 simultaneously performs discharging of the culturing liquid W by means of the culture-medium-discharging portion 41 and supplying of the culturing liquid W by means of the culture-medium-supplying portion 33.

The above-described individual embodiments can be modified to the following configurations.

As a first modification, in the first to third embodiments, not only when replacing the culture medium, for example, in the case in which the intensity of the illumination light beam that has been made to pass through the culturing liquid W is measured also, the measurement may be taken after waiting for the cells S in the culturing liquid W to move below the optical path of the optical measurement unit 7 as a result of the stirring blades 5b being stopped by means of the control portion 9.

With this configuration, because the suspended cells S are not present in the optical path of the illumination light beam that passes through the culturing liquid W, it is possible to eliminate the influence of scattering caused by the cells S, and thus, it is possible to more accurately measure the intensity of the illumination light beam that has been made to pass through the culturing liquid W.

In this modification and the fourth embodiment, although the stirring of the culturing liquid W is stopped, it suffices so long as it is possible to make the cells S in the culturing liquid W move below the optical path of the optical measurement unit 7 by means of gravity, and thus, the stirring blades 5b do not necessarily need to be stopped completely. So long as it is possible to make the cells S in the culturing liquid W move below the optical path of the optical measurement unit 7 by means of gravity, for example, the speed at which the culturing liquid W is stirred may simply be reduced by reducing the rotational speed of the stirring blades 5b.

As a second modification, in the first to fourth embodiments, for example, a portion of or the entire control portion 9 may be included in the optical measurement unit 7 without separating the control portion 9 and the optical measurement unit 7. For example, the control portion 9 may be accommodated in a housing that accommodates the illumination light source 15, the light detector 25, and so forth.

Figure 12:
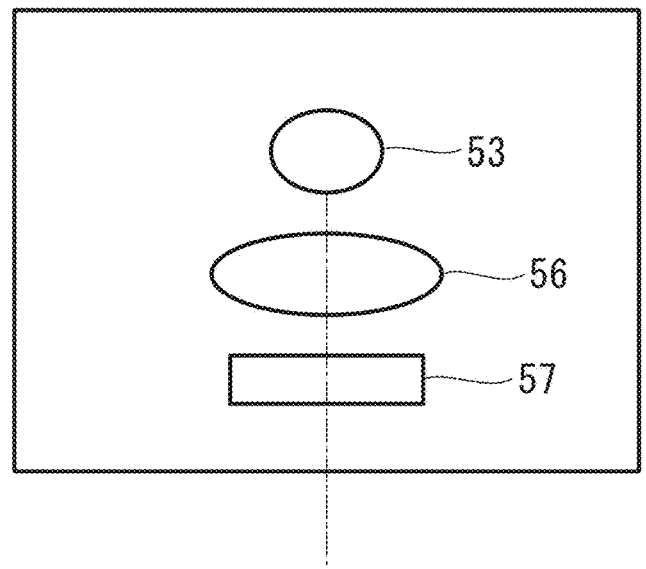
FIG. 12 is a plan view showing a light source according to a third modification of the first to fourth embodiments.

As a third modification, as shown in FIG. 12, in the first, second, and fourth embodiments, for example, the white light source 53 such as a halogen light source may be employed as the illumination light source instead of the illumination light source 15 such as an LED, and the lens 56 that converts the light beam emitted from the white light source 53 to collimated light beam and the bandpass filter 57 that extracts a specific wavelength from the light beam converted to the collimated light beam by the lens 56 may be employed.

In this case, in the case in which the light intensity of the illumination light beam is measured, the illumination light beam emitted from the white light source 53 may be radiated onto the culturing liquid W by turning on the white light source 53 or by opening/closing a shutter (not shown).

With this modification, because a halogen light source and a bandpass filter are inexpensive, it is possible to achieve a cost reduction. It is possible to apply the configurations of the white light source 53 and the bandpass filter 57 to various types of culturing liquids W, because the degree of freedom for wavelength selection is high.

Figure 13:
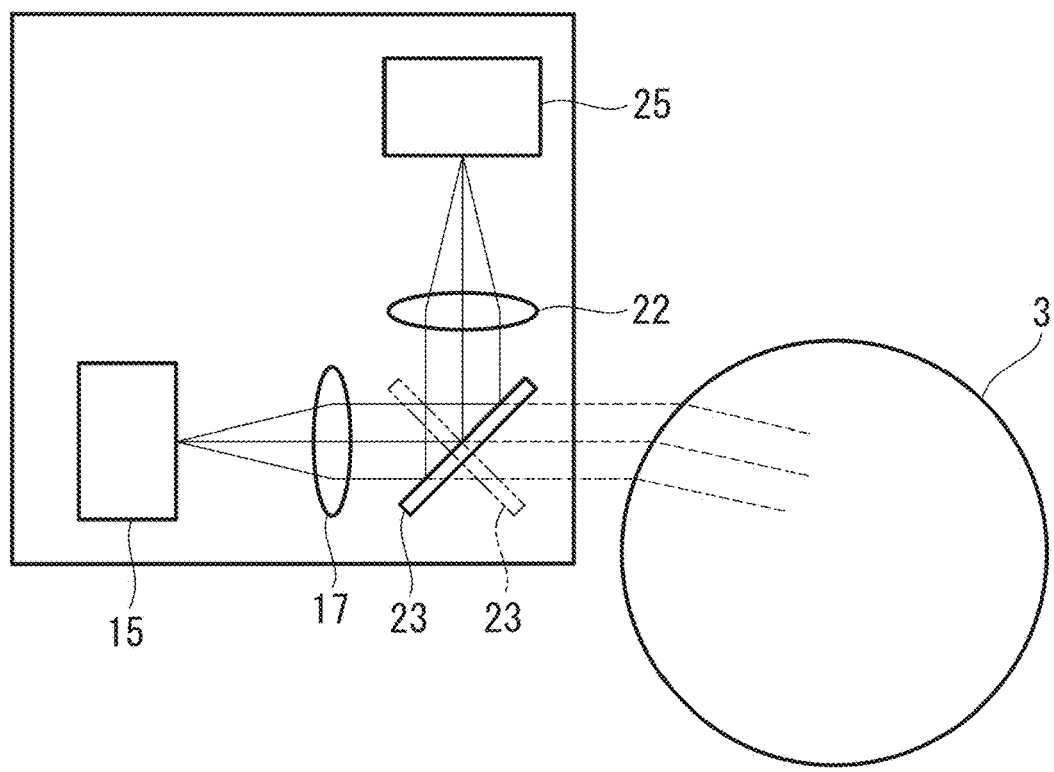
FIG. 13 is a plan view showing a light source according to a fourth modification of the first to fourth embodiments.

As a fourth modification, as shown in FIG. 13, in the first to third embodiments, for example, the orientation of the half mirror 23 may be made rotatable by 90°. Then, by rotating the half mirror 23 by 90°, the paths of the illumination light beam may be switched between the case in which the half mirror 23 allows the illumination light beam coming from the illumination light source 15 to pass therethrough toward the culturing vessel 3 and the case in which the half mirror 23 reflects the illumination light beam coming from the illumination light source 15 toward the light detector 25.

In this case, first, by disposing the half mirror 23 at the angle indicated by the solid line in FIG. 13, the illumination light beam coming from the illumination light source 15 is made to enter the light detector 25 by means of the half mirror 23, and the light intensity of the illumination light beam that has not passed through the culturing liquid W is measured by the light detector 25.

Next, by switching the angle of the half mirror 23 to the angle indicated by the broken line in FIG. 13, the illumination light beam coming from the illumination light source 15 is made to pass therethrough toward the culturing liquid W in the culturing vessel 3. Then, the illumination light beam that returns by passing through the culturing liquid W again after being folded back by the retroreflective member 19 is made to enter the light detector 25 by means of the half mirror 23, and the light intensity of the illumination light beam that has been made to pass through the culturing liquid W is measured by the light detector 25.

Then, when determining the state of the culturing liquid W on the basis of the change over time in the intensity of the illumination light beam that has passed through the culturing liquid W, the influence of the fluctuation on the output of the illumination light source 15 may be corrected by the intensity of the illumination light beam that has not passed through the culturing liquid W. By doing so, even in the case in which the output of the illumination light source 15 fluctuates, it is possible to accurately assess the state of the culturing liquid W.

As a fifth modification, in the first to fourth embodiments, the deterioration of the culturing liquid W may be measured by means of a color change.

Figure 14:
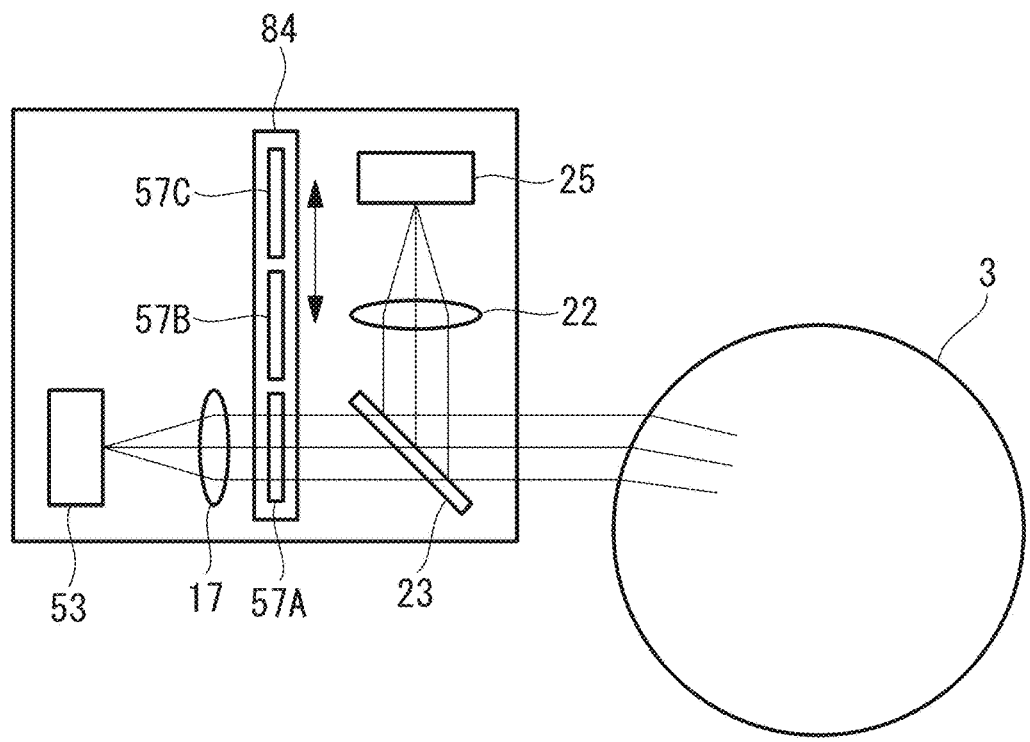
FIG. 14 is a plan view showing a light source according to a fifth modification of the first to fourth embodiments.

In this modification, as shown in FIG. 14, for example, the white light source 53 such as a halogen light source is employed as the illumination light source. Three bandpass filters 57A, 57B, and 57C having different transmission wavelengths and a switching mechanism 84, such as a turret, that selectively disposes one of the three bandpass filters 57A, 57B, and 57C in the path of the illumination light beam are disposed between the collecting lens 17 and the half mirror 23. Dulbecco MEM containing 0.001% phenol red and 10% fetal bovine serum is employed as the culturing liquid W.

The bandpass filter 57A is, for example, a filter (BP441) in which the center wavelength is 441 nm and the band width, that is, the transmission wavelength band, is 10 nm. The bandpass filter 57B is, for example, a filter (BP578) in which the center wavelength is 578 nm and the transmission wavelength band is 10 nm. The bandpass filter 57C is, for example, a filter (BP634) in which the center wavelength is 634 nm and the transmission wavelength band is 10 nm.

In this case, first, the intensity of the illumination light beam that has passed through the culturing vessel 3 in which both the cells S and the culturing liquid W are not accommodated is measured by the light detector 25 by using each of the bandpass filters 57A, 57B, and 57C. In this case, the intensity of the illumination light beam when the bandpass filter 57A is used is assumed to be $I_{0\_441}$, the intensity of the illumination light beam when the bandpass filter 57B is used is assumed to be $I_{0\_578}$ and the intensity of the illumination light beam when the bandpass filter 57C is used is assumed to be $I_{0\_634}$.

Next, the intensity of the illumination light beam that has passed through the culturing vessel 3 accommodating the culturing liquid W having a known pH is measured by the light detector 25 by using each of the bandpass filters 57A, 57B, and 57C. In this case, the intensity of the illumination light beam when the bandpass filter 57A is used is assumed to be $I_{441}$, the intensity of the illumination light beam when the bandpass filter 57B is used is assumed to be $I_{578}$, and the intensity of the illumination light beam when the bandpass filter 57C is used is assumed to be $I_{634}$.

In this case, the absorbances ($A_{441}$, $A_{578}$, and $A_{634}$) of the culturing liquid W for the respective wavelengths are expressed by the following expressions:

$$A_{441} = -\log(I_{441}/I_{0\_441});$$

$$A_{578} = -\log(I_{578}/I_{0\_578}); \text{ and}$$

$$A_{634} = -\log(I_{634}/I_{0\_634}).$$

The above-described measurements are taken for the culturing liquid W at multiple pH values, and a relational expression between the absorbance and the pH of the culturing liquid W is determined for each of the wavelengths. For example, the following is obtained:

$$pH = \log\{(A_{441} - A_{634})/(A_{578} - A_{634})\} * 1.19 + 7.86,$$

where 1.19 is the slope of a straight line obtained when $\log\{(A_{441}-A_{634})/(A_{578}-A_{634})\}$ is plotted against the pH, and 7.86 is the intercept of the straight line.

The above is the preparation performed before taking main measurements in which the changes over time in the culturing liquid W are measured in this modification.

Next, the absorbances of the culturing liquid W are measured by switching among the individual bandpass filters 57A, 57B, and 57C, and the changes over time in the pH values of the culturing liquid W are determined from the absorbances measured for the respective wavelengths and the relational expression between the absorbance and the pH determined through the preparation.

With this modification, because the deterioration of the culturing liquid W is determined by determining the pH values of the culturing liquid W from the changes over time in the intensity of the illumination light beam at the plurality of wavelengths, it is possible to enhance the measurement precision of the deterioration of the culturing liquid W.

The above-described fifth modification can be modified to the following configuration.

Figure 15:
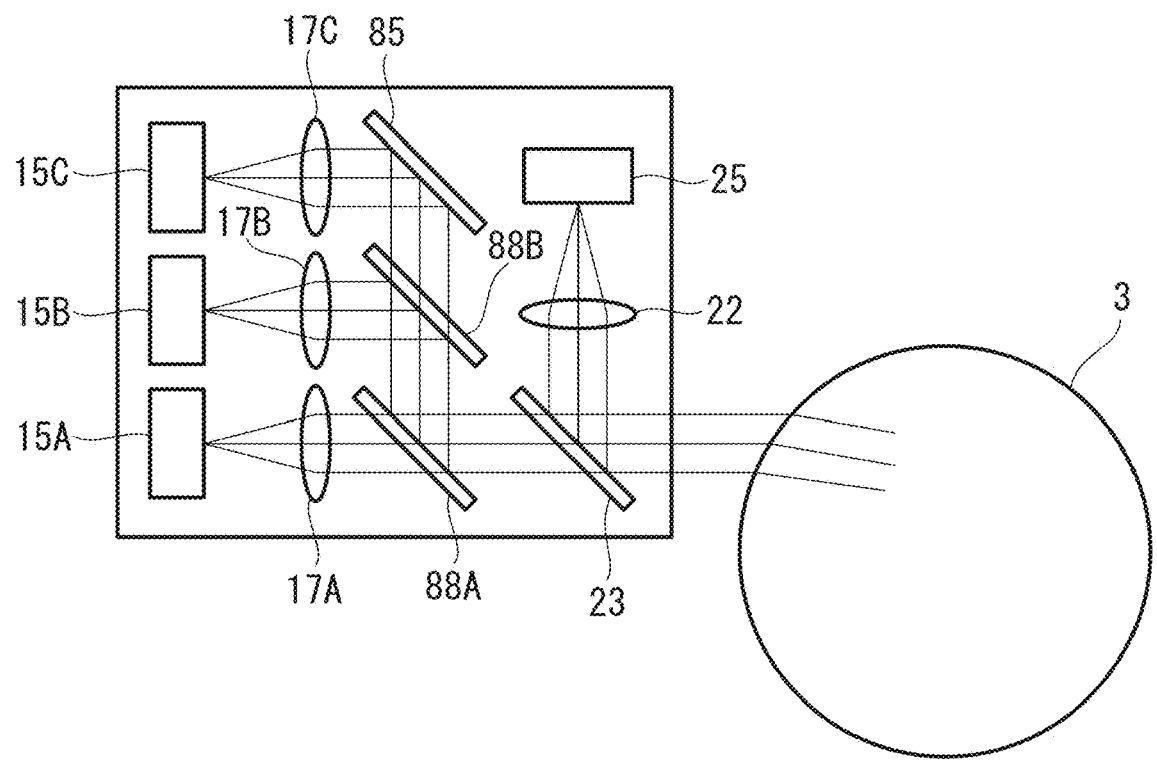
FIG. 15 is a plan view showing a light source according to a further modification of the fifth modification.

As shown in FIG. 15, for example, a plurality of LED light sources (monochromatic light sources) 15A, 15B, and 15C that emit illumination light beams at different wavelengths may be employed as illumination light sources. In the example shown in FIG. 15, the LED light source 15A emits a 441-nm monochromatic light beam, the LED light source 15B emits a 578-nm monochromatic light beam, and the LED light source 15C emits a 634-nm monochromatic light beam.

In this case, collecting lenses 17A, 17B, and 17C that collect the illumination light beams coming from the individual LED light sources 15A, 15B, and 15C, and a mirror 85 and dichroic mirrors 87A and 87B that reflect or transmit the illumination light beams collected by the collecting lenses 17A, 17B, and 17C to combine the optical paths of the illumination light beams may be employed instead of the collecting lens 17, the bandpass filters 57A, 57B, and 57C and the switching mechanism 84.

With this modification, instead of switching among the bandpass filters 57A, 57B, and 57C as in the above-described fifth modification, it is possible to change the measurement wavelength by simply switching ON/OFF the individual LED light sources 15A, 15B, and 15C.

As a sixth modification, in the first to fourth embodiments, the state of the culturing liquid W may be monitored, for example, in a state in which the entire culture-medium-monitoring apparatuses 1, 31, 51, and 81, including the optical measurement unit 7 and the culturing vessel 3, are disposed in a dark place.

With this configuration, it is possible to accurately measure the intensity of the illumination light beam that has been made to pass through the culturing liquid W without being influenced by light from illumination equipment, light from a monitor, and external light.

In the above-described individual embodiments, although the closed-bottom cylindrical culturing vessel 3 formed of an optically transparent material has been described as an example of the vessel, it is possible to employ, as the culturing vessel, a vessel having an arbitrary shape such as a bag-like shape, a spherical shape, or a box-like shape. For example, a disposable bag-like culturing vessel may be employed. It is possible to employ a culturing vessel made of an arbitrary material such as a hard material or a soft material such as vinyl. The culturing vessel 3 need not be entirely transparent, and the culturing vessel 3 may have a transparent portion that allows the illumination light beam to pass therethrough in a portion thereof.

As has been described above, with the above-described individual embodiments, it is possible to measure the state of the culturing liquid W in a non-contact manner without directly inserting a pH sensor into the culturing liquid W, and thus, it is possible to reduce the risk of contaminating the culturing system.

Although the embodiments of the present invention have been described in detail with reference to the drawings, the specific configurations are not limited to these embodiments, and design alterations or the like within a range that does not depart from the scope of the present invention are also encompassed. For example, there is no limitation to the forms in which the present invention is applied to the above-described individual embodiments and modifications, and the present invention may be applied to forms in which these embodiments and modifications are appropriately combined without particular limitation. Even in the case in which the culture-medium-supplying portion 33 and the culture-medium-discharging portion 41 are used in combination with the alert-issuing portion 13 and the culture medium replacement is automatically performed by means of control performed by the control portion 9, a notification may be issued to the user, indicating that the timing for replacing the culture medium has arrived.

On the basis of the fourth embodiment, culture-medium-monitoring apparatuses according to the following Appended Features are derived.

(Appended Feature 1)

A culture-medium-monitoring apparatus including:
  an optical measurement unit that includes
    an illuminating portion that radiates an illumination light beam onto a culture medium in a vessel, and
    a light-detecting portion that is disposed so as to sandwich the vessel between the illuminating portion and the light-detecting portion and that detects an intensity of the illumination light beam that has passed through the culture medium in the vessel;
  a stirrer that stirs the culture medium in the vessel; and
  a control portion that controls the optical measurement unit to repeatedly detect the intensity of the illumination light beam at a prescribed timing, controls the stirrer to stop stirring of the culture medium when detecting the intensity of the illumination light beam, and determines a state of the culture medium on the basis of changes over time in the intensity of the illumination light beam.

(Appended Feature 2)

A culture-medium-monitoring apparatus according to Appended Feature 1, further including:
  a culture-medium-supplying portion that supplies the culture medium to the vessel; and
  a medium-discharging portion that discharges the culture medium from the vessel,
  wherein, in the case in which the control portion determines that the timing at which the culture medium needs to be replaced has arrived on the basis of the changes over time in the intensity of the illumination light beam detected by the light-detecting portion, a portion of the culture medium is discharged from the vessel by means of the culture-medium-discharging portion, and a new culture medium is supplied to the vessel by means of the culture-medium-supplying portion.

Fifth Embodiment

A culture-medium-monitoring apparatus according to a fifth embodiment of the present invention will be described below with reference to the drawings.

Figure 16:
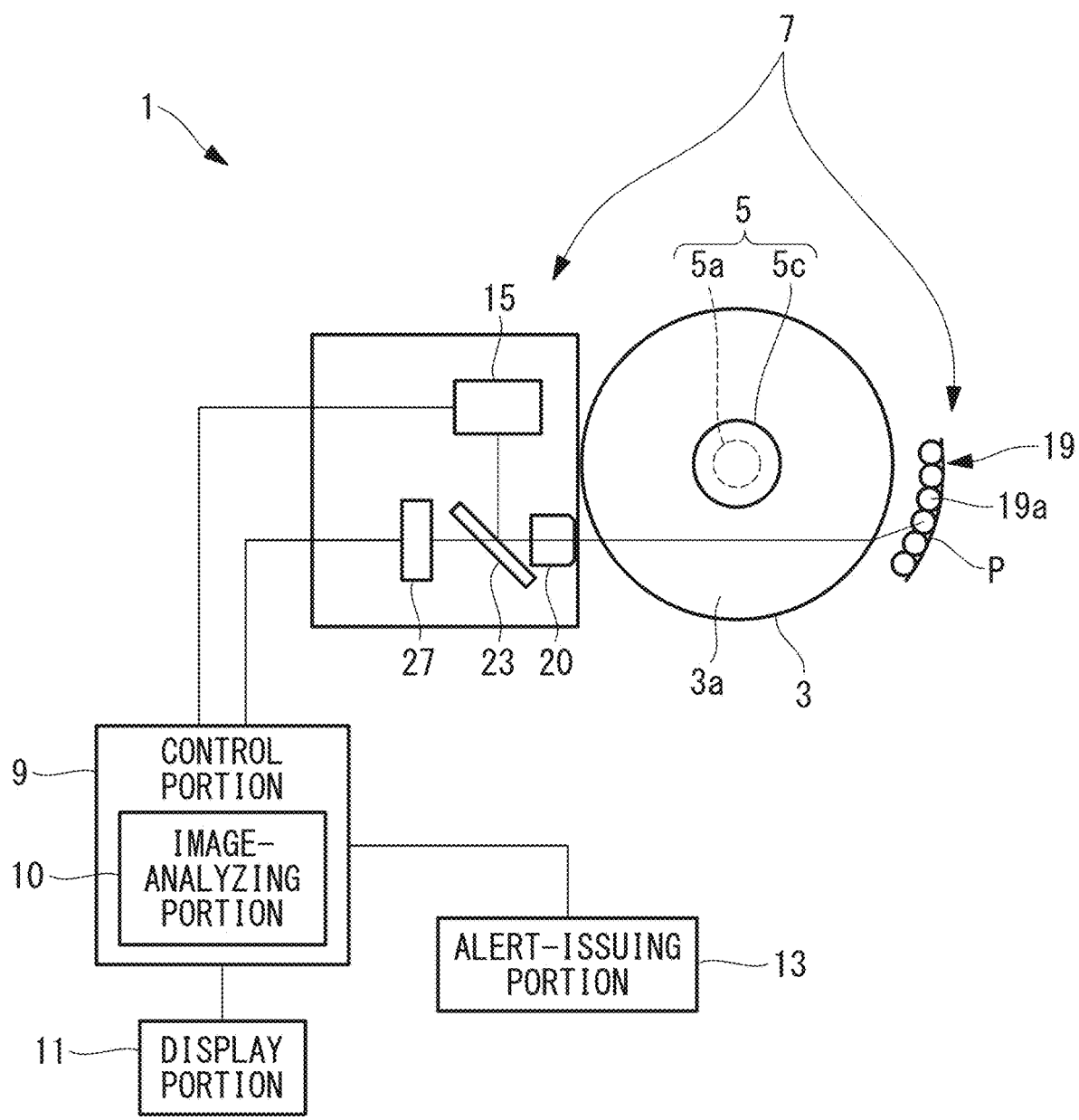
FIG. 16 is a schematic configuration diagram showing, from above, a culture-medium-monitoring apparatus according to a fifth embodiment of the present invention.
Figure 17:
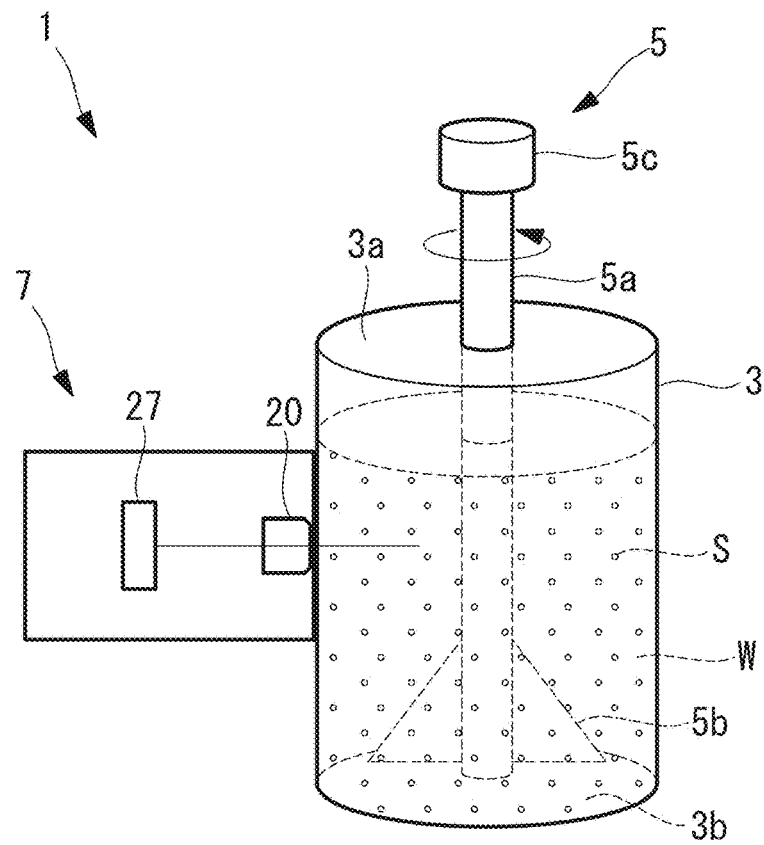
FIG. 17 is a schematic configuration diagram for explaining the configuration of the culture-medium-monitoring apparatus in FIG. 16.
Figure 18:
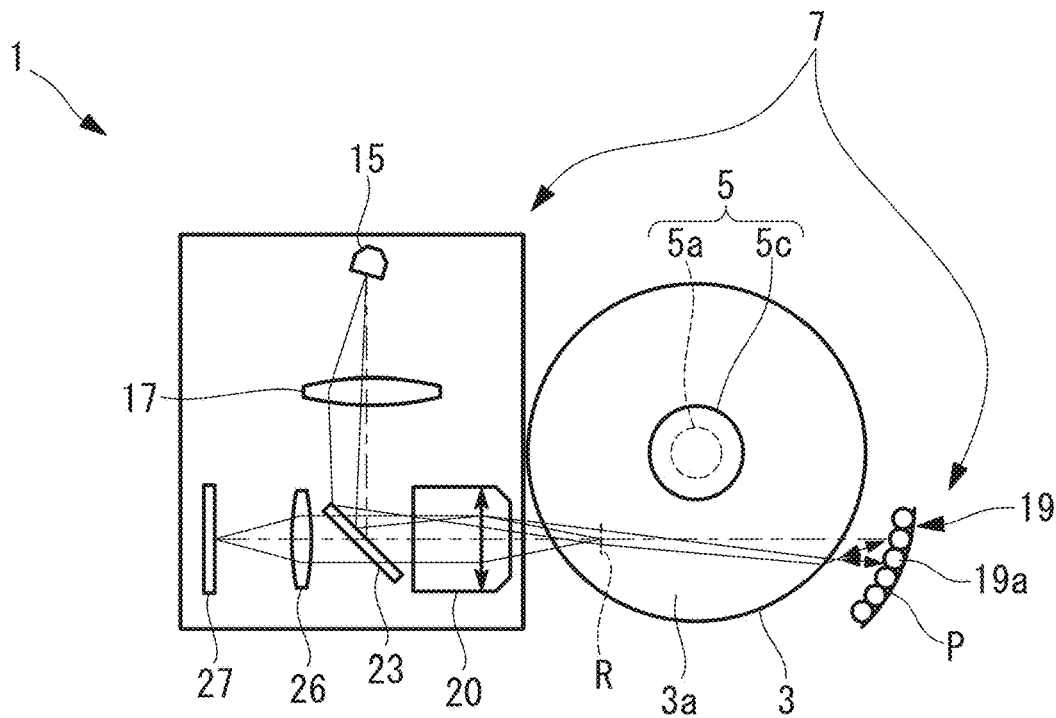
FIG. 18 is a schematic configuration diagram for explaining the configuration of an optical measurement unit in FIG. 16.

As shown in FIGS. 16 to 18, a culture-medium-monitoring apparatus 1 according to this embodiment includes, for example: the stirrer 5 that stirs the culturing liquid (culture medium) W accommodated in the culturing vessel (vessel) 3 together with the cells S; the optical measurement unit 7 that acquires an image of a specific region R (see FIG. 18) in which the culturing liquid W and the cells S are present in the culturing vessel 3; the control portion 9 that controls the stirrer 5 and the optical measurement unit 7 and that determines the state of the culturing liquid W; the display portion 11 that displays various types of information; and the alert-issuing portion (notifying portion) 13, such as a smartphone, that issues a notification about the information to the user.

The culturing vessel 3 is, for example, a vessel for a bioreactor or the like for performing suspension culturing of the cells S. This culturing vessel 3 is a closed-bottom cylindrical vessel in which the top surface 3a is closed. The culturing vessel 3 is formed of an optically transparent material and is capable of allowing the illumination light beam generated by the optical measurement unit 7 to pass therethrough. Phenol red, which is a pH indicator, or the like is added to the culturing liquid W for determining the state of the culturing liquid W.

The stirrer 5 includes: the stirring rod 5a that is inserted into the culturing vessel 3 via the top surface 3a of the culturing vessel 3; the plurality of stirring blades 5b provided on the stirring rod 5a; and the motor 5c that rotates the stirring rod 5a about a longitudinal axis.

As shown in FIG. 18, the optical measurement unit 7 includes: the illumination light source (illuminating portion) 15 that generates the illumination light beam; the collecting lens (illuminating portion) 17 that collects the illumination light beam emitted from the illumination light source 15; an objective lens (illuminating portion) 20 that radiates the illumination light beam collected by the collecting lens 17 onto the specific region R in which the culturing liquid W and the cells S are present in the culturing vessel 3; the retroreflective member 19 that returns, toward the illumination light source 15, the illumination light beam that has passed through the specific region R in the culturing vessel 3; the half mirror 23 that splits the path off of the illumination light beam returned by the retroreflective member 19; an imaging optical system 26 that causes the illumination light beam that has been split off by the half mirror 23 to form an image; and a two-dimensional image-acquisition device (image-acquisition portion) 27 that captures the image formed by the imaging optical system 26. The specific region R corresponds to the focal plane of the objective lens 20, that is, an image-acquisition region.

The illumination light source 15 is an LED (Light Emitting Diode) that generates, for example, a 560-nm monochromatic light beam, as the illumination light beam. The illumination light source 15 radiates the illumination light beam toward the specific region R in the culturing vessel 3 from outside the culturing vessel 3.

The objective lens 20 collects the illumination light beam coming from the illumination light source 15 in the specific region R in the culturing vessel 3, while collecting the illumination light beam that returns by being made to pass through the specific region R in the culturing vessel 3 again by the retroreflective member 19.

The retroreflective member 19 is disposed outside the culturing vessel 3 so as to substantially face the illumination light source 15, the collecting lens 17, and the objective lens 20 in a state in which the culturing vessel 3 is sandwiched between the retroreflective member 19 and the objective lens 20 in the direction intersecting the depth direction. The illumination light source 15, the collecting lens 17, the objective lens 20, and the retroreflective member 19 are disposed at positions at which the illumination light beam traveling inside the culturing vessel 3 does not interfere with the stirring rod 5*a* and the stirring blades 5*b* of the stirrer 5.

As shown in FIGS. 16 and 18, the retroreflective member 19 has, for example, an array in which the numerous micro-reflective elements 19*a* are arrayed along the surface P. The surface P is a surface intersecting the optical axis of the illumination light beam that has passed through the culturing vessel 3. The surface P may be a flat surface or a curved surface. As shown in FIG. 16, the surface P may be, for example, a curved surface that has a constant curvature and that is curved in one direction or a curved surface that is curved in multiple directions.

The reflective elements 19*a* are, for example, prisms or spherical glass beads. The illumination light beam that has entered the reflective elements 19*a* exits from the reflective elements 19*a* as a result of being reflected in the opposite direction from the entry direction. Because the reflective elements 19*a* are minute, there is almost no displacement between the entry path and the exit path of the illumination light beam. Therefore, the illumination light beam reflected by the retroreflective member 19 returns along the same path as the path of the illumination light beam entering the retroreflective member 19. In other words, the illumination light beam travels through the same path in a back-and-forth manner between the interior of the culturing vessel 3 and the retroreflective member 19.

It is possible to arbitrarily set the position and the angle at which the retroreflective member 19 is disposed. The retroreflective member 19 may be attached to, for example, a stand, a wall, or the like (not shown), or the retroreflective member 19 may be attached to a side surface of the culturing vessel 3. The installation position and the installation angle of the retroreflective member 19 may be an arbitrary position, distance, and angle so long as it is possible to receive the illumination light beam that has passed through the culturing vessel 3 from the illumination light source 15.

The half mirror 23 is disposed in an optical path between the objective lens 20 and the two-dimensional image-acquisition device 27. The half mirror 23 reflects the illumination light beam coming from the illumination light source 15, thus making the illumination light beam enter the objective lens 20, while allowing the illumination light beam returning along the optical path from the retroreflective member 19 via the objective lens 20 to pass therethrough toward the two-dimensional image-acquisition device 27.

The two-dimensional image-acquisition device 27 is a CCD image sensor or a CMOS image sensor. The two-dimensional image-acquisition device 27 captures the image formed by the imaging optical system 26, thus acquiring an image of the specific region R in the culturing vessel 3.

The control portion 9 is, for example, a PC (Personal Computer). The control portion 9 includes, for example, an interface circuit, a storage portion such as a hard disk drive, a CPU (Central Processing Unit), and a RAM (Random Access Memory) (none of these components are shown). As shown in FIG. 16, the control portion 9 includes an image-analyzing portion 10 that analyzes the image acquired by the two-dimensional image-acquisition device 27.

The storage portion stores various types of programs that are executed by the CPU.

The CPU loads the various types of programs stored in the storage portion, and executes the following functions. Specifically, the control portion 9 controls the ON/OFF state of the illumination light source 15, driving of the motor 5*c* of the stirrer 5, image analysis by the image-analyzing portion 10, image acquisition by the two-dimensional image-acquisition device 27 and saving of the acquired image, image display by the display portion 11, issuing of a notification to the user by means of the display portion 11 or the alert-issuing portion 13, and so forth.

The image-analyzing portion 10 analyzes the image of the specific region R in the culturing vessel 3 acquired by the two-dimensional image-acquisition device 27, thus classifying each pixel into a region including the cells S or a background region.

For example, the image-analyzing portion 10 extracts outlines of the cells S in which a prominent change in contrast occurs, and classifies the areas inside the extracted outlines as the cells S, while classifying areas outside the extracted outlines as the background. Because a background pixel has a low frequency, the image-analyzing portion 10 may use frequency diffraction in combination with the above image analysis to classify the pixels.

The image-analyzing portion 10 calculates a representative pixel value that represents the pixels classified as the background regions. For example, the image-analyzing portion 10 determines an average lightness or a median lightness of the pixels classified as the background as the representative pixel value of the pixels of the background. In the following, the pixels classified as the background regions will also be referred to as the background pixels.

As a result of causing the illumination light beam to be radiated onto the specific region R in the culturing vessel 3 from the illumination light source 15 at the prescribed time intervals and causing the two-dimensional image-acquisition device 27 to capture images of the illumination light beam that has passed through the specific region R, the control portion 9 causes the images of the specific region R to be repeatedly acquired at the prescribed timing. Then, the control portion 9 calculates, for the individual acquired images of the specific region R, the representative pixel values of the background pixels by means of the image-analyzing portion 10, and determines the state of the culturing liquid W in the culturing vessel 3 on the basis of the changes over time in the calculated representative pixel values.

The control portion 9 stores an initial representative pixel value of the background pixels of an image of the illumination light beam that has been made to pass through the specific region R before starting to culture the cells S. The control portion 9 compares the representative pixel values of the background pixels of the images of the specific region R acquired while culturing the cells S with the initial representative pixel value. Then, in the case in which the representative pixel values of the background pixels have fallen below the initial representative pixel value by a prescribed amount or more, the control portion 9 issues a notification to the user by means of the display portion 11 or the alert-issuing portion 13, indicating that the timing for replacing the culture medium has arrived.

Next, the operation of the culture-medium-monitoring apparatus 1 according to this embodiment will be described.

In the case in which the state of the culturing liquid W is monitored by means of the culture-medium-monitoring apparatus 1 having the above-described configuration while culturing the cells S, first, the culturing liquid W in the culturing vessel 3 is stirred as a result of the control portion 9 causing the stirrer 5 to be driven. By doing so, the cells S are cultured while being suspended in the culturing liquid W.

Next, as a result of the control portion 9 causing the illumination light source 15 to be turned on at the prescribed time intervals, the 560-nm illumination light beam emitted from the illumination light source 15 is radiated onto the specific region R in the culturing vessel 3 via the collecting lens 17, the half mirror 23, and the objective lens 20. The illumination light beam that has passed through the specific region R is reflected by the retroreflective member 19, and returns toward the culturing vessel 3 by passing along the same path as the entry path to the retroreflective member 19.

Then, after passing through the specific region R in the culturing vessel 3 again, the images of the illumination light beam are captured by the two-dimensional image-acquisition device 27 via the objective lens 20, the half mirror 23, and the imaging optical system 26. By doing so, time-lapse images of the specific region R are repeatedly acquired by the two-dimensional image-acquisition device 27. The time-lapse images of the specific region acquired by the two-dimensional image-acquisition device 27 are saved by the control portion 9.

Next, as a result of the control portion 9 controlling the image-analyzing portion 10, the background pixels are individually extracted from the individual images of the specific region R in the culturing vessel 3 acquired at the prescribed time intervals, and the representative pixel values (lightnesses) of the extracted background pixels are calculated. Then, the control portion 9 monitors the changes over time in the representative pixel values of the background pixels of the respective images calculated by the image-analyzing portion 10.

When the representative pixel values of the background pixels have fallen below the initial representative pixel value by the prescribed amount or more, the control portion 9 controls the display portion 11 or the alert-issuing portion 13 and the display portion 11 or the alert-issuing portion 13 issues a notification to the user, indicating that the timing for replacing the culture medium has arrived.

In this case, although the region in which the cells S are present in the culturing liquid W changes every moment, as a result of monitoring only the changes over time in the background pixels, which do not include the pixels containing the cells S, extracted from the images of the specific region R in the culturing vessel 3, it is possible to determine the state of the culturing liquid W without the influence of scattering of the illumination light beam by the cells S.

As a result of monitoring the state of the culturing liquid W by using the optical system for acquiring the images of the cells S, in other words, the objective lens 20, the imaging optical system 26, and the two-dimensional image-acquisition device 27, it is not necessary to separately provide an optical system for measuring the changes over time in the background pixels, and it is possible to simplify the apparatus. Therefore, it is possible to accurately monitor the state of the culturing liquid W without making the apparatus complex, and on the basis of the images of the specific region R in the culturing vessel 3.

As a result of the illumination light beam that has passed through the specific region R in the culturing vessel 3 being radiated onto the specific region R in the culturing vessel 3 again by being made to pass along the same optical path as the entry optical path by the retroreflective member 19, regardless of the material, the shape, the size, and so forth of the culturing vessel 3, it is possible to reliably acquire images of that specific region R by means of the two-dimensional image-acquisition device 27. Therefore, it is possible to stably monitor the culturing liquid W on the basis of the state of the culturing liquid W determined by the control portion 9 even if a wide variety of culturing vessels 3 are employed.

This embodiment can be modified to the following configuration.

Figure 19:
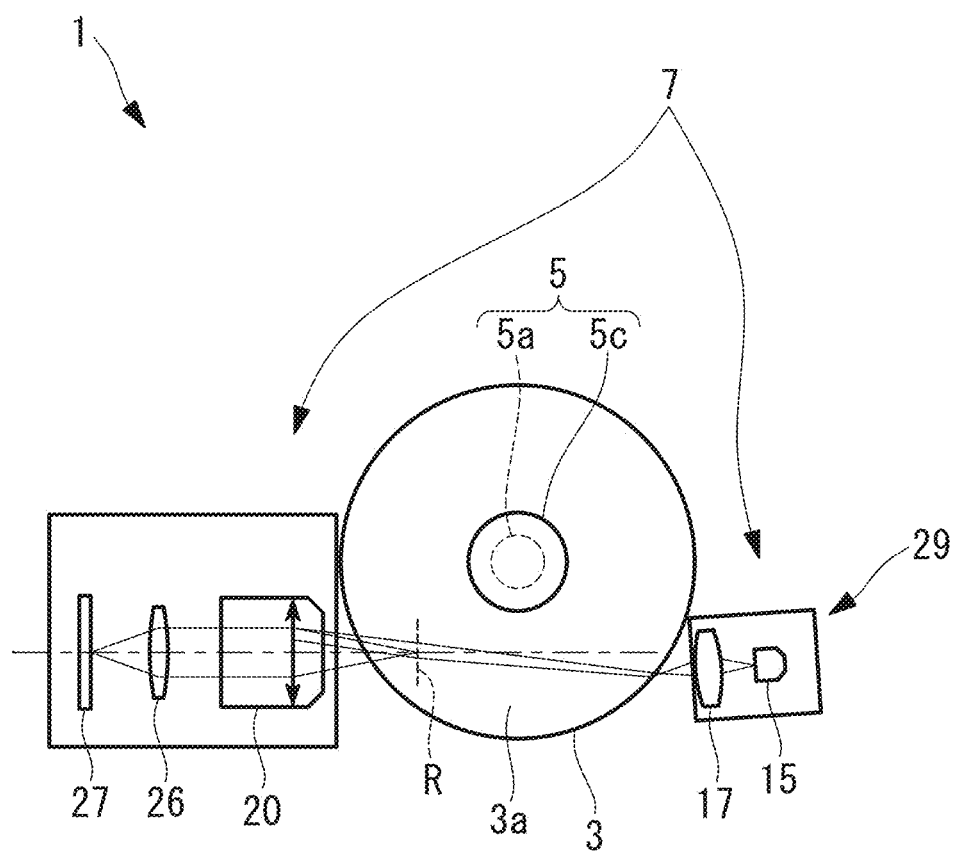
FIG. 19 is a schematic configuration diagram showing, from above, a culture-medium-monitoring apparatus according to a modification of the fifth embodiment of the present invention.

As shown in FIG. 19, for example, an oblique illumination optical system 29 formed from the illumination light source 15 and the collecting lens 17 may be disposed at the position at which the retroreflective member 19 would be disposed.

In this case, the illumination light beam emitted from the illumination light source 15 of the oblique illumination optical system 29 obliquely illuminates the specific region R in the culturing vessel 3 via the collecting lens 17. Then, the illumination light beam that has passed through the specific region R forms an image by means of the imaging optical system 26 after being collected by the objective lens 20, and the image is captured by the two-dimensional image-acquisition device 27.

With this modification, the illumination light beam that has passed through the specific region R in the culturing vessel 3 does not pass through the half mirror 23 and the retroreflective member 19, and this illumination light beam passes through the objective lens 20 once; therefore, it is possible to enhance the utilization efficiency of the illumination light beam.

Sixth Embodiment

Next, a culture-medium-monitoring apparatus according to a sixth embodiment of the present invention will be described.

Figure 20:
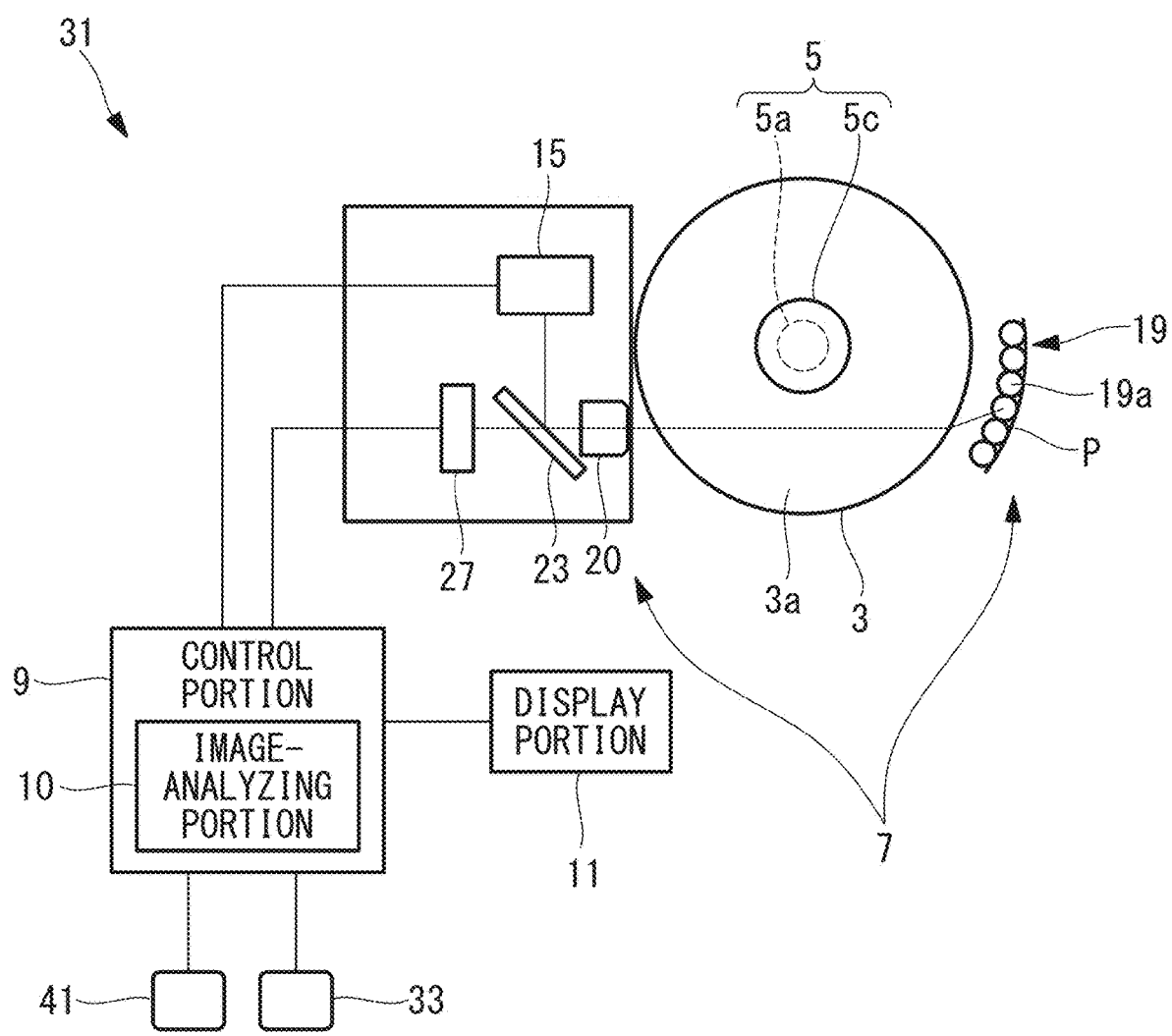
FIG. 20 is a schematic configuration diagram showing, from above, a culture-medium-monitoring apparatus according to a sixth embodiment of the present invention.
Figure 21:
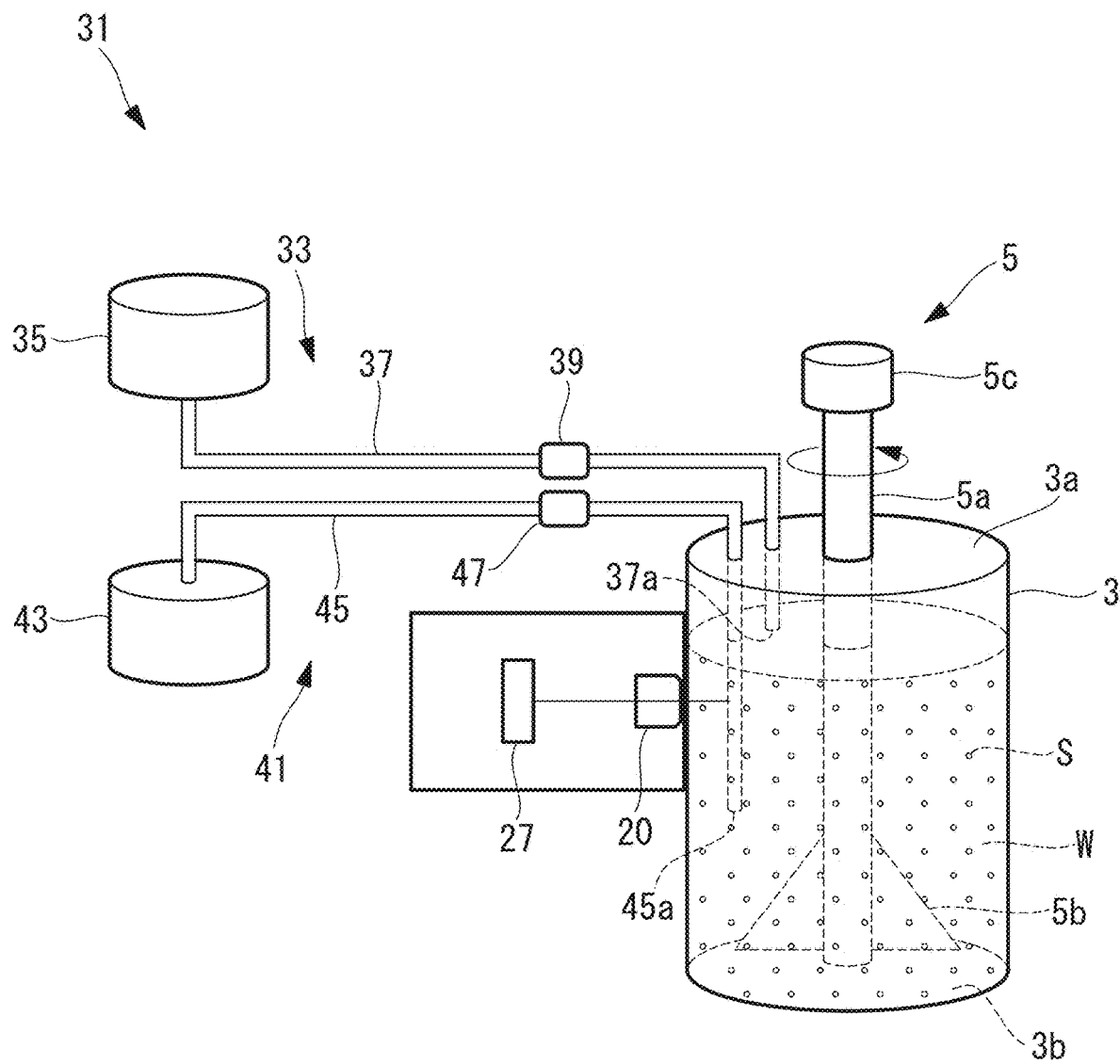
FIG. 21 is a schematic configuration diagram for explaining the configuration of the culture-medium-monitoring apparatus in FIG. 20.

As shown in FIGS. 20 and 21, a culture-medium-monitoring apparatus 31 according to this embodiment differs from the fifth embodiment, for example, in that the culture-medium-supplying portion 33 that supplies the culturing liquid W to the culturing vessel 3 and the culture-medium-discharging portion 41 that discharges the culturing liquid W from the culturing vessel 3 are included, and that the control portion 9 controls the culture-medium-supplying portion 33 and the culture-medium-discharging portion 41.

In the following, portions having the same configurations as those of the culture-medium-monitoring apparatus 1 according to the fifth embodiment will be given the same reference signs, and descriptions thereof will be omitted.

As shown in FIG. 21, the culture-medium-supplying portion 33 includes: the culture-medium-supplying tank 35 that holds the new culturing liquid W; the culture-medium-supplying pipe 37 that forms the flow channel for feeding the culturing liquid W to the culturing vessel 3 from the culture-medium-supplying tank 35; and the culture-medium-supplying pump 39 that feeds the culturing liquid W in the culture-medium-supplying tank 35 to the culturing vessel 3 via the culture-medium-supplying pipe 37.

The culture-medium-supplying pipe 37 is inserted into the culturing vessel 3 at a position at which the culture-medium-supplying pipe 37 does not block the path of the illumination light beam and does not interfere with the stirring blades 5b. It is preferable that, in the culture-medium-supplying pipe 37, the supply port 37a from which the culturing liquid W is supplied be disposed, for example, in the vicinity of a liquid surface of the culturing liquid W accommodated in the culturing vessel 3.

The culture-medium-discharging portion 41 includes: the culture-medium-discharging tank 43 that collects the culturing liquid W discharged from the culturing vessel 3; the culture-medium-discharging pipe 45 that forms the flow channel for feeding the culturing liquid W to the culture-medium-discharging tank 43 from the culturing vessel 3; and the culture-medium-discharging pump 47 that feeds the culturing liquid W in the culturing vessel 3 to the culture-medium-discharging tank 43 via the culture-medium-discharging pipe 45.

The culture-medium-discharging pipe 45 is inserted into the culturing vessel 3 at a position at which the culture-medium-discharging pipe 45 does not block the path of the illumination light beam and does not interfere with the stirring blades 5b. It is preferable that, in the culture-medium-discharging pipe 45, the suction port 45a from which the culturing liquid W is sucked out be disposed, for example, in the vicinity of an intermediate depth in the culturing liquid W accommodated in the culturing vessel 3.

The culture-medium-discharging pump 47 is capable of discharging the culturing liquid W in the culturing vessel 3, for example, at a speed that does not cause the cells S in the culturing liquid W to be sucked out in the state in which the suspended cells S have moved downward in the culturing vessel 3 due to gravity as a result of stopping the stirring of the culturing liquid W or reducing the stirring speed.

The control portion 9 performs ON/OFF switching of the supply of the culturing liquid W to the culturing vessel 3 from the culture- medium-supplying tank 35 by controlling driving of the culture-medium-supplying pump 39. The control portion 9 performs ON/OFF switching of the discharge of the culturing liquid W to the culture-medium-discharging tank 43 from the culturing vessel 3 by controlling driving of the culture-medium-discharging pump 47.

In the case in which the representative pixel value of the background pixels calculated by the image-analyzing portion 10 has fallen below the initial representative pixel value by the prescribed amount or more, the control portion 9, first, causes the driving of the motor 5c of the stirrer 5 to be stopped, thus stopping the stirring of the culturing liquid W. Then, the control portion 9 causes the culture-medium-discharging pump 47 to be driven to discharge a portion of the culturing liquid W to the culture-medium-discharging tank 43 from the culturing vessel 3 via the culture-medium-discharging pipe 45, and causes the culture-medium-supplying pump 39 to be driven to supply the new culturing liquid W to the culturing vessel 3 from the culture-medium-supplying tank 35 via the culture-medium-supplying pipe 37.

Next, the operation of the culture-medium-monitoring apparatus 31 according to this embodiment will be described.

In the case in which the state of the culturing liquid W is monitored by means of the culture-medium-monitoring apparatus 31 having the above-described configuration while culturing the cells S, as with the fifth embodiment, images of the specific region R in the culturing vessel 3 are repeatedly acquired at the prescribed time intervals as a result of the control portion 9 controlling the optical measurement unit 7, and the state of the culturing liquid W is determined on the basis of the changes over time in the representative pixel values of the background pixels of the individual images of the specific region R.

When the representative pixel values of the background pixels of the images of the specific region R in the culturing vessel 3 calculated by the image-analyzing portion 10 have fallen below the initial representative pixel value by the prescribed amount or more, the stirring of the culturing liquid W is stopped as a result of the control portion 9 controlling the motor 5c of the stirrer 5. By doing so, the cells S suspended in the culturing liquid W sink toward the lower portion of the culturing vessel 3.

Next, about half of the culturing liquid W in the culturing vessel 3 is discharged as a result of the control portion 9 causing the culture-medium-discharging pump 47 to be driven, and the discharged culturing liquid W is collected in the culture-medium-discharging tank 43. The suction port 45a of the culture-medium-discharging pipe 45 is disposed in the vicinity of the intermediate depth in the culturing liquid W, and the cells S in the culturing liquid W have sunk to the lower portion of the culturing vessel 3; therefore, it is possible to efficiently collect only the culturing liquid W in the culturing vessel 3.

Next, as a result of the control portion 9 causing the culture-medium-supplying pump 39 to be driven, the new culturing liquid W is replenished in the culturing vessel 3 from the culture-medium-supplying tank 35. By doing so, the culturing liquid W in the culturing vessel 3 is replaced.

After replacing the culturing liquid W, monitoring of the state of the culturing liquid W is continued, on the basis of the changes over time in the representative pixel values of the background pixels of the individual images, as a result of the control portion 9 causing the illumination light beam to be radiated onto the specific region R in the culturing vessel 3 and the images of the specific region R to be acquired at the prescribed time intervals again.

Therefore, with the culture-medium-monitoring apparatus 31 according to this embodiment, whether the culturing liquid W in the culturing vessel 3 has deteriorated, that is, whether the timing for replacing the culture medium has arrived, is ascertained by means of the control portion 9 on the basis of the changes over time in the representative pixel values of the background pixels of the images of the specific region R calculated by the image-analyzing portion 10. Therefore, as a result of the control portion 9 controlling the culture-medium-supplying portion 33 and the culture-medium-discharging portion 41 on the basis of the changes over time in the representative pixel values of the background pixels, it is possible to replace the culture medium at an accurate timing without requiring time and effort on the part of the user.

As a result of stopping the stirring of the culturing liquid W when replacing the culture medium, the cells S in the culturing liquid W move to a lower portion of the culturing vessel 3 due to gravity. As a result of disposing the suction port 45a of the culture-medium-discharging pipe 45 in the vicinity of an intermediate depth in the culturing liquid W in the culturing vessel 3, it is possible to prevent the cells S in the culturing liquid W from being discharged together with the culturing liquid W discharged by means of the culture-medium-discharging portion 41.

This embodiment can be modified to the following configuration.

Figure 22:
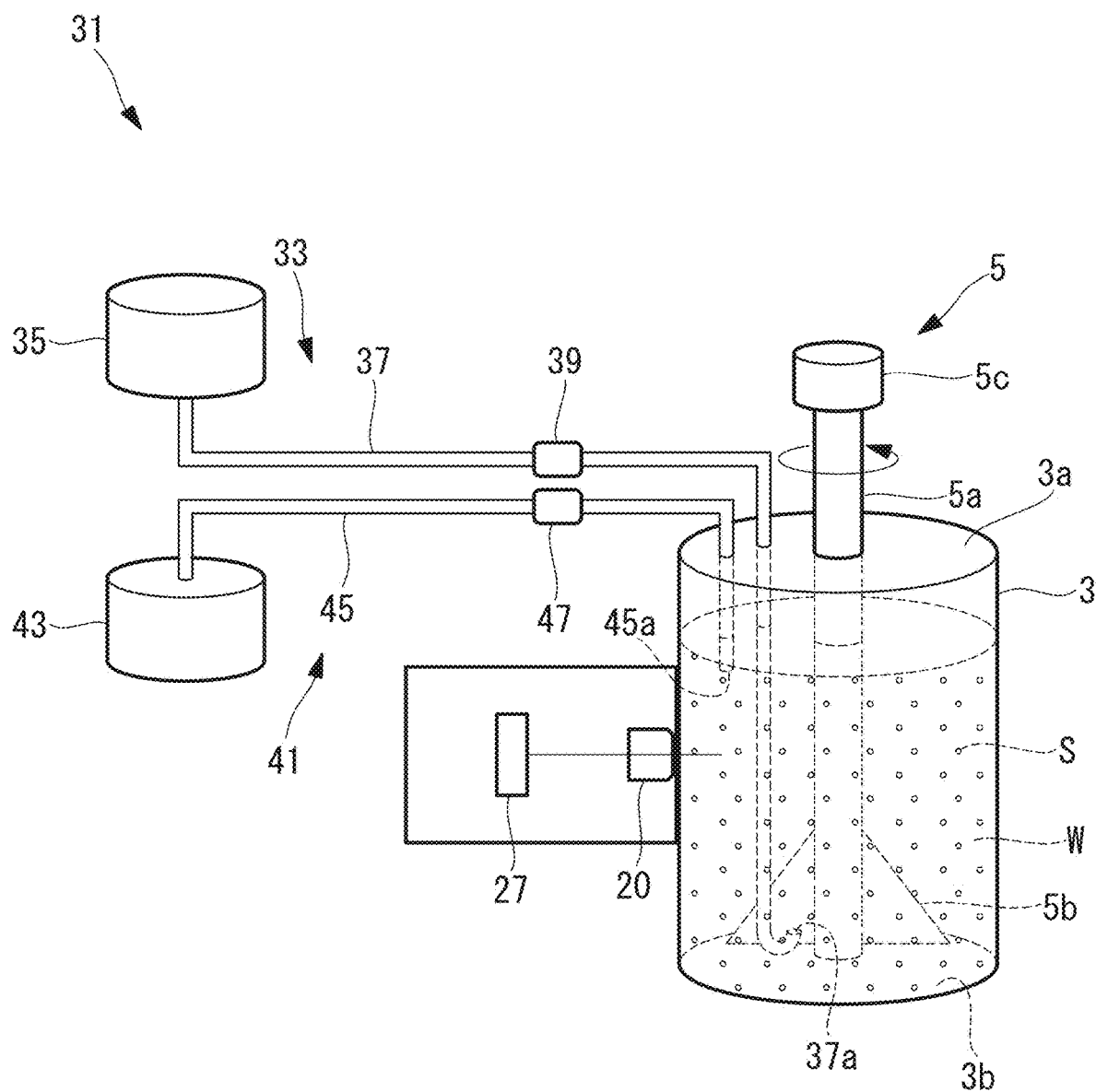
FIG. 22 is a schematic configuration diagram for explaining the configuration of a culture-medium-monitoring apparatus according to a modification of the sixth embodiment of the present invention.

Although the supply port 37a of the culture-medium-supplying pipe 37 is disposed in the vicinity of the liquid surface of the culturing liquid W in the culturing vessel 3 in this embodiment, alternatively, as shown in FIG. 22, for example, the culture-medium-supplying pipe 37 may be extended to a lower portion of the culturing vessel 3, and the supply port 37a may be disposed in the vicinity of a bottom surface 3b of the culturing vessel 3.

In this case, it is desirable that the supply port 37a of the culture-medium-supplying pipe 37 be formed in an upward U-shape that is folded back toward the top surface 3a in the vicinity of the bottom surface 3b of the culturing vessel 3. It is preferable that the suction port 45a of the culture-medium-discharging pipe 45 be disposed at a position that is slightly lower than the liquid surface of the culturing liquid W.

When replacing the culture-medium, the control portion 9 causes the driving of the motor 5c of the stirrer 5 to be stopped, thus stopping the stirring of the culturing liquid W. As a result of controlling the culture-medium-discharging pump 47 of the culture-medium-discharging portion 41 and the culture-medium-supplying pump 39 of the culture-medium-supplying portion 33, the control portion 9 simultaneously performs discharging of the culturing liquid W from the culturing vessel 3 and supplying of the culturing liquid W to the culturing vessel 3.

Because the deteriorated culturing liquid W that needs to be replaced has a lower specific gravity as compared with that of the new culturing liquid W, the deteriorated culturing liquid W is separated into an upper portion of the culturing vessel 3, and the new culturing liquid W is separated into the lower portion of the culturing vessel 3. When replacing the culture medium, as a result of stopping the stirring of the culturing liquid W, the cells S in the culturing liquid W move to the lower portion of the culturing vessel 3 due to gravity.

Therefore, with the culture-medium-monitoring apparatus 31 according to this modification, as a result of disposing the suction port 45a of the culture-medium-discharging pipe 45 near the liquid surface of the culturing liquid W, it is possible to reduce the risk of the cells S being discharged together with the culturing liquid W. The newly supplied new culturing liquid W accumulates in the lower portion of the culturing vessel 3, whereas the deteriorated culturing liquid W that needs to be replaced moves upward in the culturing vessel 3; therefore, it is possible to selectively discharge only the deteriorated culturing liquid W even if the culturing liquid W is simultaneously discharged and supplied. Therefore, as a result of simultaneously discharging and supplying the culturing liquid W, it is possible to reduce the time required to replace the culture medium.

Seventh Embodiment

Next, a culture-medium-monitoring apparatus according to a seventh embodiment of the present invention will be described.

Figure 23:
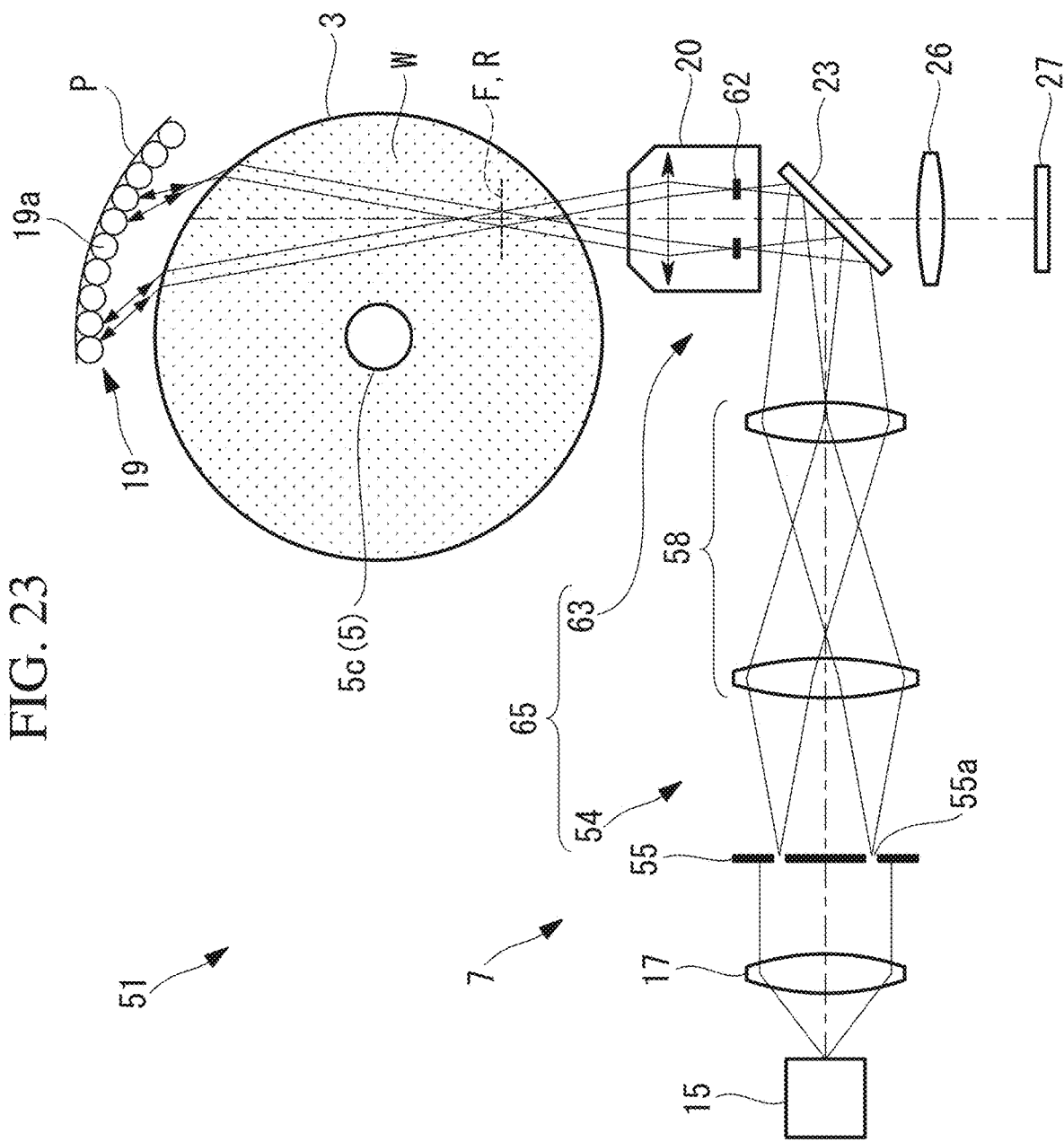
FIG. 23 is a schematic configuration diagram showing, from above, a culture-medium-monitoring apparatus according to a seventh embodiment of the present invention.

As shown in FIG. 23, a culture-medium-monitoring apparatus 51 according to this embodiment differs from the fifth and sixth embodiments, for example, in that the optical measurement unit 7 is provided with the phase contrast optical system 65 that is formed from an illumination optical system (illuminating portion) 54 that illuminates the cells S suspended in the culturing liquid W to generate a phase contrast image of the cells S and the detection optical system 63 that causes the phase contrast image of the cells S, which are suspended in the culturing liquid W and are irradiated with the illumination light beam, to be formed on the light-detecting portion. Although the culture-medium-monitoring apparatus 51 includes the control portion 9, the display portion 11, and the alert-issuing portion 13, in FIG. 23, the control portion 9, the display portion 11, and the alert-issuing portion 13 are not shown.

In the following, portions having the same configurations as those of the culture-medium-monitoring apparatuses 1 and 31 according to the fifth and sixth embodiments will be given the same reference signs, and descriptions thereof will be omitted.

The illumination optical system 54 includes: the illumination light source 15; the collecting lens 17; an aperture 55 having a ring slit 55a which is an annular opening; a relay optical system 58; the half mirror 23; and the objective lens 20.

The ring slit 55a of the aperture 55 is disposed at an optically conjugate position with respect to the pupil position of the objective lens 20. The illumination light beam that has been collected by the collecting lens 17 passes through only the ring slit 55a in the aperture 55. It is possible to adjust the position of the aperture 55 in a direction orthogonal to the optical axis of the illumination light beam entering the aperture 55.

The relay optical system 58 relays the illumination light beam that has passed through the ring slit 55a. The relay optical system 58 is formed from, for example, a pair of convex lenses.

The half mirror 23 reflects a portion of the illumination light beam that has been relayed thereto by the relay optical system 58 from the illumination light source 15, for example, about 50% of the illumination light beam that has been made incident on the half mirror 23, toward the objective lens 20, while allowing a portion of the illumination light beam that has entered from the objective lens 20 side, for example, about 50% of the illumination light beam that has been made incident on the half mirror 23, to pass therethrough.

The objective lens 20 is disposed so that the optical axis thereof is disposed in a substantially horizontal direction, and is disposed so as to face the culturing vessel 3. The focal plane F of the objective lens 20 is disposed inside the culturing vessel 3. The illumination light beam that has been reflected by the half mirror 23 enters the objective lens 20 along the optical axis of the objective lens 20, and is made to exit toward the culturing vessel 3 from the objective lens 20. The illumination light beam that has been made to exit from the objective lens 20 travels across the interior of the culturing vessel 3 in the substantially horizontal direction after passing through the side wall of the culturing vessel 3, and is made to exit to outside the culturing vessel 3 after passing through the side wall of the culturing vessel 3 again. As a result of adjusting the position of the aperture 55, it is possible to change the position of the illumination light beam that enters the culturing vessel 3 from the objective lens 20 in a direction intersecting the optical axis of the illumination light beam.

The retroreflective member 19 is disposed so as to sandwich the culturing vessel 3 between the objective lens 20 and the retroreflective member 19 in the substantially horizontal direction.

The objective lens 20 and the retroreflective member 19 are disposed in a path of the illumination light beam between the objective lens 20 and the retroreflective member 19 at the positions at which the stirring rod 5a and the stirring blades 5b of the stirrer 5 do not interfere with the illumination light beam.

The detection optical system 63 includes: the objective lens 20; a phase film 62 that is disposed at the pupil position of the objective lens 20; the imaging optical system 26; and the two-dimensional image-acquisition device 27. In other words, the objective lens 20 serves as the illumination optical system 54 and the detection optical system 63.

The phase film 62 has a shape that corresponds to the shape of the ring slit 55a of the illumination optical system 54, that is, an annular shape. The phase film 62 shifts the phase of the illumination light beam that passes through the phase film 62 by λ/4. The phase film 62 is disposed at a conjugate position with respect to the ring slit 55a of the illumination optical system 54. The phase film 62 may be disposed at an optically conjugate position with respect to the pupil position of the objective lens 20.

Next, the operation of the culture-medium-monitoring apparatus 51 according to this embodiment will be described.

First, in the case in which the state of the culturing liquid W is monitored by means of the culture-medium-monitoring apparatus 51 having the above-described configuration while performing phase contrast observation of the cells S, the illumination light beam emitted from the illumination light source 15 is radiated onto the specific region R in the culturing vessel 3 via the collecting lens 17, the aperture 55, the relay optical system 58, the half mirror 23, and the objective lens 20 as a result of the control portion 9 turning on the illumination light source 15.

The illumination light beam that has been radiated onto the specific region R is reflected by the retroreflective member 19 after passing through the specific region R. Then, the illumination light beam is collected by the objective lens 20 after passing through the specific region R in the culturing vessel 3 in the opposite direction. Therefore, the cells S suspended in the culturing liquid W in the specific region R in the culturing vessel 3 are illuminated by the two types of illumination methods, namely, epi-illumination by means of the objective lens 20 and transmission illumination by means of the retroreflective member 19.

While passing through the culturing vessel 3 twice, a portion of the illumination light beam (signal light beam) passes through the transparent cells S suspended in the culturing liquid W and is refracted. After passing through the culturing liquid W in the culturing vessel 3 twice, the illumination light beam passes through the objective lens 20 and the half mirror 23, and forms and an image on the two-dimensional image-acquisition device 27 by means of the imaging optical system 26.

Here, the phase film 62 is disposed in the objective lens 20 at the optically conjugate position with respect to the ring slit 55a. The illumination light beam (refracted light beam) that has passed through the cells S in the culturing vessel 3 travels through a position that is different from that of the phase film 62 in the objective lens 20, and is made to exit the objective lens 20. On the other hand, the illumination light beam (straight traveling light beam) that did not pass through the cells S in the culturing vessel 3 is subjected to a phase shift as a result of passing through the phase film 62 in the objective lens 20, and is made to exit the objective lens 20. Therefore, an optical image of the cells S having a contrast due to interference between the refracted light beam and the straight traveling light beam is formed on the two-dimensional image-acquisition device 27. By doing so, a phase contrast image of the cells S is acquired by the two-dimensional image-acquisition device 27.

Next, the images of the specific region R in the culturing vessel 3 are repeatedly acquired at the prescribed time intervals as a result of the control portion 9 controlling the optical measurement unit 7, and the state of the culturing liquid W is determined on the basis of the changes over time in the representative pixel values of the background pixels of the images of the specific region R.

Then, when the representative pixel values of the background pixels have fallen below the initial representative pixel value by the prescribed amount or more, the control portion 9 controls the display portion 11 or the alert-issuing portion 13, and the display portion 11 or the alert-issuing portion 13 issues a notification to the user, indicating that the timing for replacing the culture medium has arrived.

In this case, as described above, the retroreflective member 19 reflects the illumination light beam by means of the numerous micro-reflective elements 19a along the same path as the entry path. Therefore, the illumination light beam that has entered the culturing vessel 3 from the retroreflective member 19 illuminates the specific region R in the culturing vessel 3 from the same direction and at the same angle regardless of the shape of the side wall of the culturing vessel 3 that is present between the retroreflective member 19 and the interior of the culturing vessel 3.

For example, in the case in which the side wall of the culturing vessel 3 has a curvature or unevenness, the side wall of the culturing vessel 3 exhibits a lens effect on the illumination light beam. However, as a result of the illumination light beam traveling through the side wall of the culturing vessel 3 along the same path in a back-and-forth manner, the lens effect is canceled out. In other words, the orientation and angle of the illumination light beam that enters the interior of the culturing vessel 3 from the retroreflective member 19 are not influenced by the side wall between the retroreflective member 19 and the interior of the culturing vessel 3.

Therefore, even if the culturing vessel 3 is made of a flexible material and the side wall of the culturing vessel 3 shows successive deformation, or even if the culturing vessel 3 is replaced with another culturing vessel 3 having a different shape and size, it is possible to stably illuminate the cells S in the culturing vessel 3 by means of the illumination light beam coming from the retroreflective member 19.

In the case in which the side wall of the culturing vessel 3 between the objective lens 20 and the interior of the culturing vessel 3 is flat, the illumination light beam that has entered the interior of the culturing vessel 3 from the objective lens 20 travels ahead along the optical axis of the objective lens 20. In other words, coaxial epi-illumination is realized.

On the other hand, in the case in which the side wall of the culturing vessel 3 between the objective lens 20 and the interior of the culturing vessel 3 has a curvature or unevenness, the optical axis of the illumination light beam that enters the interior of the culturing vessel 3 from the objective lens 20 becomes tilted with respect to the optical axis of the objective lens 20 due to the lens effect of the side wall of the culturing vessel 3. As a result, the position of the illumination light beam (straight traveling light beam) that has returned to the objective lens 20 from the retroreflective member 19 is sometimes displaced in a direction intersecting the optical axis from the position of the phase film 62. In this case, by adjusting the position of the illumination light beam radiated onto the culturing vessel 3 from the illumination optical system 54 by adjusting the position of the aperture 55, the illumination light beam (straight traveling light beam) returning to the objective lens 20 from the retroreflective member 19 passes through the phase film 62.

As has been described above, with the culture-medium-monitoring apparatus 51 according to this embodiment, it is possible to monitor the state of the culturing liquid W by using the high-resolution, high-contrast images of the cells S by means of the phase contrast optical system 65 formed from the illumination optical system 54 and the detection optical system 63.

Eighth Embodiment

Next, a culture-medium-monitoring apparatus according to an eighth embodiment of the present invention will be described.

Figure 24:
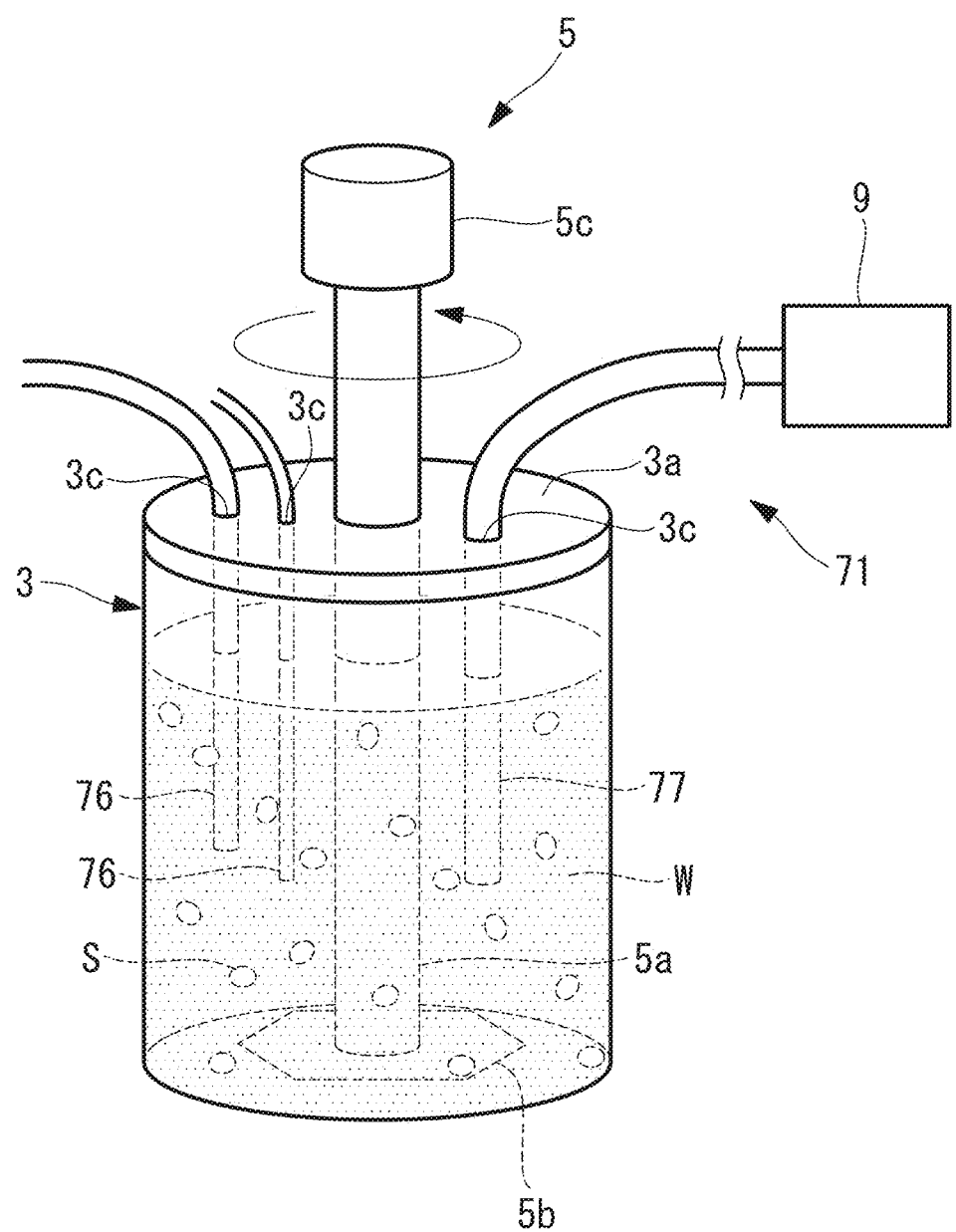
FIG. 24 is a schematic configuration diagram showing a culture-medium-monitoring apparatus and a culturing vessel according to an eighth embodiment of the present invention.
Figure 25:
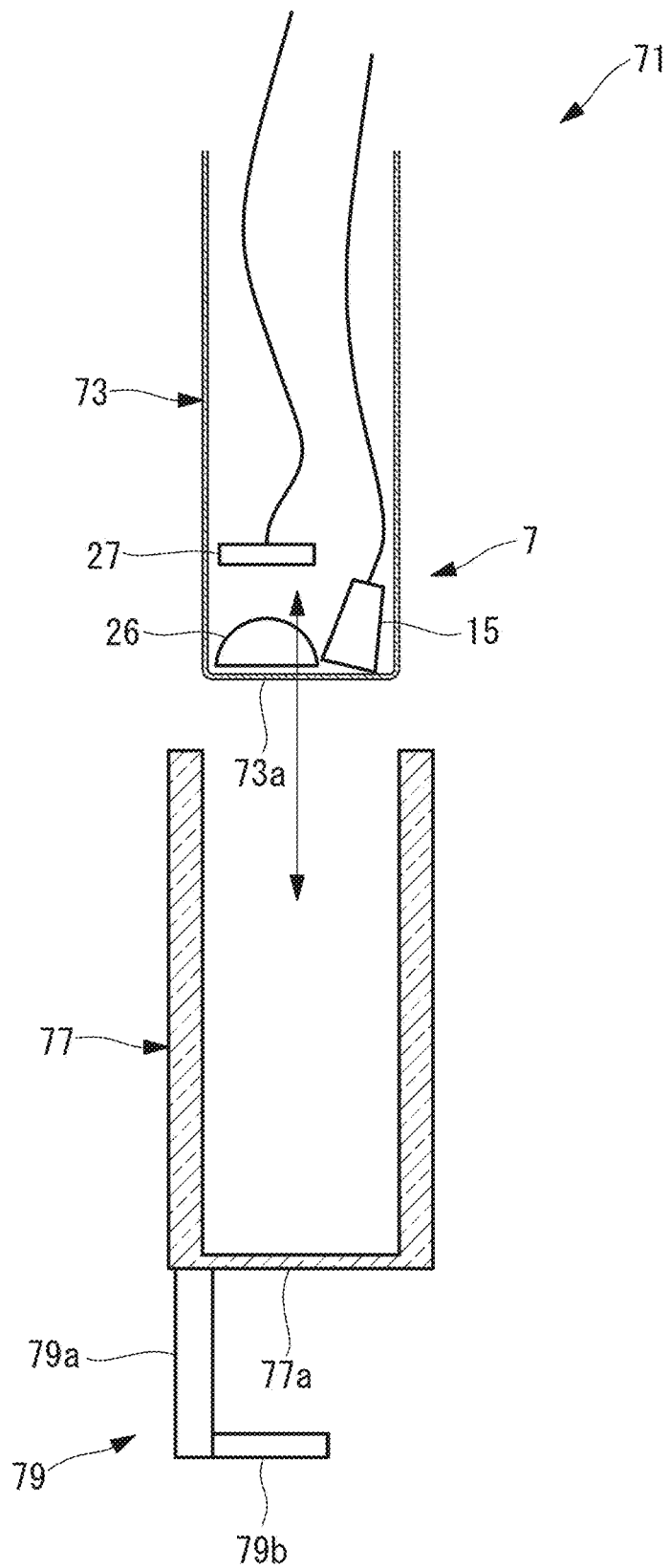
FIG. 25 is a longitudinal sectional view showing a state in which a housing forming the culture-medium-monitoring apparatus in FIG. 24 and a protective tube are separated from each other.
Figure 26:
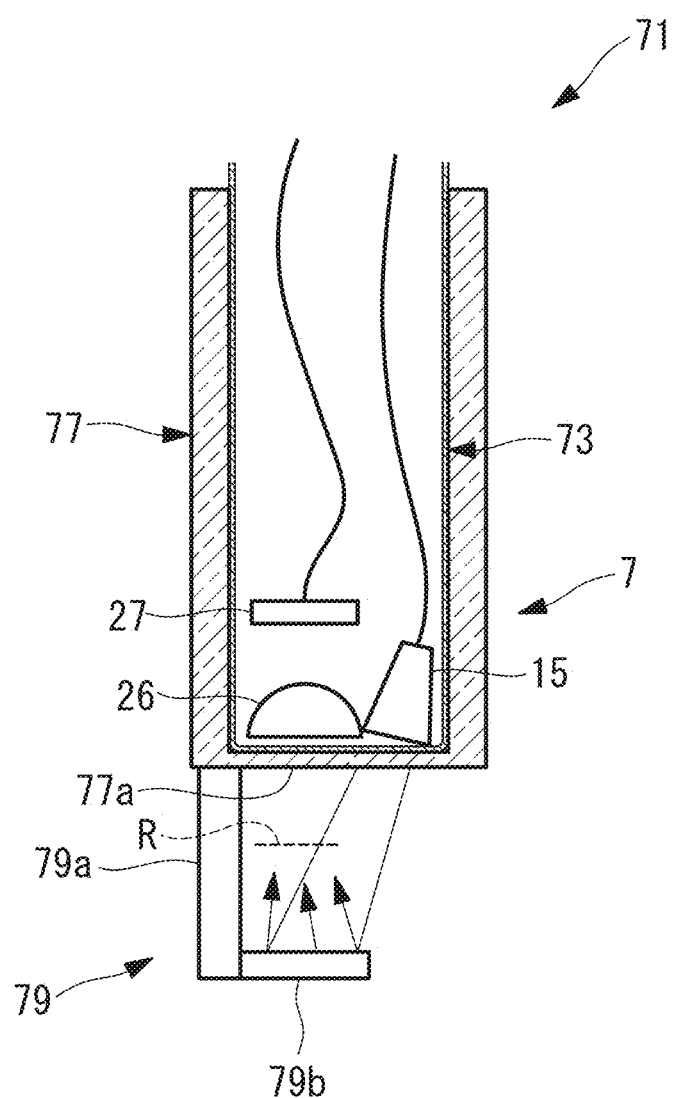
FIG. 26 is a longitudinal sectional view showing a state in which the protective tube is attached to the housing forming the culture-medium-monitoring apparatus in FIG. 24.

As shown in FIGS. 24 to 26, a culture-medium-monitoring apparatus 71 according to this embodiment differs from the fifth embodiment, for example, in that a housing 73 that accommodates the illumination light source 15, the imaging optical system 26, and the two-dimensional image-acquisition device 27 that form the optical measurement unit 7 and a tubular protective tube 77 that covers a periphery of the housing 73 are provided, and that images of the specific region R in the culturing vessel 3 are acquired in the state in which the housing 73, in which the periphery thereof is covered with the protective tube 77, is inserted into the culturing liquid W in the culturing vessel 3. In this embodiment, the image-analyzing portion 10, the display portion 11, and the alert-issuing portion 13 are not shown.

In the following, portions having the same configurations as those of the culture-medium-monitoring apparatuses 1, 31, and 51 according to the fifth to seventh embodiments will be given the same reference signs, and descriptions thereof will be omitted.

In this embodiment, as shown in FIG. 24, the culturing vessel 3 is provided with, in the top surface 3a, a plurality of ports 3c for inserting various types of tubes 76. In the example shown in FIG. 24, three ports 3c are provided in the top surface 3a of the culturing vessel 3, and the tubes 76 through which the cells S in the culturing liquid W are collected and a chemical is administered into the culturing liquid W are inserted into two of the ports 3c. The individual ports 3c are provided with O-rings (not shown) for sealing off gaps between the tubes 76 and the ports 3c. By doing so, the interior of the culturing vessel 3 is maintained in a sealed state.

The housing 73 has a long, thin tubular form capable of being inserted into and removed from the protective tube 77. The housing 73 is formed of, for example, polyvinyl chloride or the like, and possesses flexibility. As shown in FIG. 25, the housing 73 has, at a distal end thereof in the longitudinal direction, a transparent portion 73a through which the illumination light beam and an observation light beam pass.

The protective tube 77 has a long, thin shape that allows the protective tube 77 to be inserted into the culturing liquid W via the port 3c of the culturing vessel 3. The protective tube 77 is formed so as to allow the housing 73 to be accommodated in the interior thereof. When the protective tube 77 is inserted into the port 3c, the O-ring (not shown) seals off the gap between the protective tube 77 and the port 3c. The protective tube 77 is formed of, for example, a transparent resin material such as an acrylic resin (PMMA) or polyvinyl chloride. Therefore, the entire protective tube 77 forms a transparent portion that is optically transparent and that allows the illumination light beam and the observation light beam to pass therethrough. In this embodiment, a distal end of the protective tube 77 in the longitudinal direction serves as a transparent portion 77a.

The protective tube 77 has a protruding portion 79 that protrudes in the longitudinal direction of the protective tube 77 on the outside of the transparent portion 77a. As shown in FIGS. 25 and 26, the protruding portion 79 includes, for example: a columnar portion 79a that extends along the longitudinal direction of the protective tube 77 from the distal end of the protective tube 77; and a bent portion (reflective member) 79b that is disposed at a position at which the bent portion 79b blocks a space in front of the transparent portion 73a as a result of being bent in a direction intersecting the longitudinal direction of the protective tube 77 from the distal end of the columnar portion 79a.

In the state in which the housing 73 is inserted into the protective tube 77, the columnar portion 79a is disposed at a position at which the columnar portion 79a is displaced from the respective optical axes of the illumination light source 15 and the imaging optical system 26.

In the state in which the housing 73 is inserted into the protective tube 77, the bent portion 79b is disposed on the optical axes of the illumination light source 15 and the imaging optical system 26. The bent portion 79b serves as a reflective member that obliquely illuminates the specific region R in the culturing vessel 3 by reflecting, toward the imaging optical system 26, the illumination light beam that has been made to exit to outside the protective tube 77 from the illumination light source 15 via the transparent portion 73a of the housing 73 and the transparent portion 77a of the protective tube 77.

As shown in FIGS. 25 and 26, the illumination light source 15 is disposed at the distal-end portion of the housing 73 in a state in which the illumination light source 15 faces the transparent portion 73a.

The imaging optical system 26 is disposed next to the illumination light source 15 at the distal-end portion of the housing 73 in a state in which the imaging optical system 26 faces the transparent portion 73a. The imaging optical system 26 causes the observation light beam that enters the housing 73 via the transparent portion 73a to form an image on the light beam-receiving surface of the two-dimensional image-acquisition device 27.

The two-dimensional image-acquisition device 27 is disposed farther on a base-end side than the imaging optical system 26 is at the distal-end portion of the housing 73.

Next, the operation of the culture-medium-monitoring apparatus 71 according to this embodiment will be described.

In the case in which the state of the culturing liquid W is monitored by means of the culture-medium-monitoring apparatus 71 having the above-described configuration while observing the cells S, as shown in FIGS. 24 to 26, the housing 73 in which the periphery of the housing 73 is covered with the protective tube 77 is inserted into the culturing liquid W via the port 3c of the culturing vessel 3. The housing 73 is sterilized in advance.

Next, the illumination light beam is made to exit the illumination light source 15 in the housing 73 via the transparent portion 73a of the housing 73 and the transparent portion 77a of the protective tube 77. The illumination light beam that has been made to exit the transparent portion 77a of the protective tube 77 is reflected by the bent portion 79b of the protruding portion 79 in front of the transparent portion 77a toward the transparent portion 77a. By doing so, the illumination light beam is radiated onto the specific region R in the culturing vessel 3 between the transparent portion 77a of the protective tube 77 and the bent portion 79b.

The observation light beam returning from the specific region R as a result of being irradiated with the illumination light beam forms an image by means of the imaging optical system 26 via the transparent portion 77a of the protective tube 77 and the transparent portion 73a of the housing 73, and an optical image of the observation light beam is captured by the two-dimensional image-acquisition device 27.

Next, the images of the specific region R in the culturing vessel 3 are repeatedly acquired at the prescribed time intervals as a result of the control portion 9 controlling the optical measurement unit 7, and the state of the culturing liquid W is determined on the basis of the changes over time in the representative pixel values of the background pixels of the images of the specific region R.

Then, when the representative pixel values of the background pixels have fallen below the initial representative pixel value by the prescribed amount or more, the control portion 9 controls the display portion 11 or the alert-issuing portion 13 and the display portion 11 or the alert-issuing portion 13 issues a notification to the user, indicating that the timing for replacing the culture medium has arrived.

As has been described above, with the culture-medium-monitoring apparatus 71 according to this embodiment, it is possible to insert the housing 73 into the culturing vessel 3 in the state in which the periphery of the housing 73 is covered with the protective tube 77 by utilizing the port 3c for inserting the tube 76 into the culturing vessel 3, and, as a result of radiating the illumination light beam onto the specific region R from the housing 73 inserted into the culturing liquid W and receiving the observation light beam from the specific region R with the housing 73, it is possible to obtain a good observation image of the specific region R without greatly being influenced by limitations on the shape, the size, the material, and so forth of the culturing vessel 3 to be used. Therefore, it is possible to apply the culture-medium-monitoring apparatus 71 to a wide variety of culturing vessels 3, and thus, it is possible to stably monitor the state of the culturing liquid W in various types of culturing vessels 3.

As a result of the protective tube 77 having a shape that allows the protective tube 77 to be inserted into the culturing liquid W via the port 3c of the culturing vessel 3, it is possible to insert the housing 73, the illumination light source 15, the imaging optical system 26, and the two-dimensional image-acquisition device 27 into the culturing vessel 3 and operate these components in the culturing vessel 3 in the state in which the housing 73 as well as the illumination light source 15, the imaging optical system 26, and the two-dimensional image-acquisition device 27 in the housing 73 are safely protected by the protective tube 77. As a result of forming the protective tube 77 with a transparent resin material such as an acrylic resin or polyvinyl chloride, it is possible to use the protective tube 77 in a UV-sterilized state, and it is possible to make only the protective tube 77 disposable and replace the protective tube 77 after use. By doing so, it is possible to avoid contamination of the culturing liquid W as compared with the case in which the repeatedly used housing 73 is directly inserted into the culturing liquid W.

As a result of restricting the specific region R to be irradiated with the illumination light beam in the culturing vessel 3 to the space between the transparent portion 77a of the protective tube 77 and the bent portion 79b of the protruding portion 79, it is possible to capture an image of the cells S that have intruded into the space between the transparent portion 77a of the protective tube 77 and the bent portion 79b of the protruding portion 79.

Ninth Embodiment

Next, a culture-medium-monitoring apparatus according to a ninth embodiment of the present invention will be described.

Figure 27:
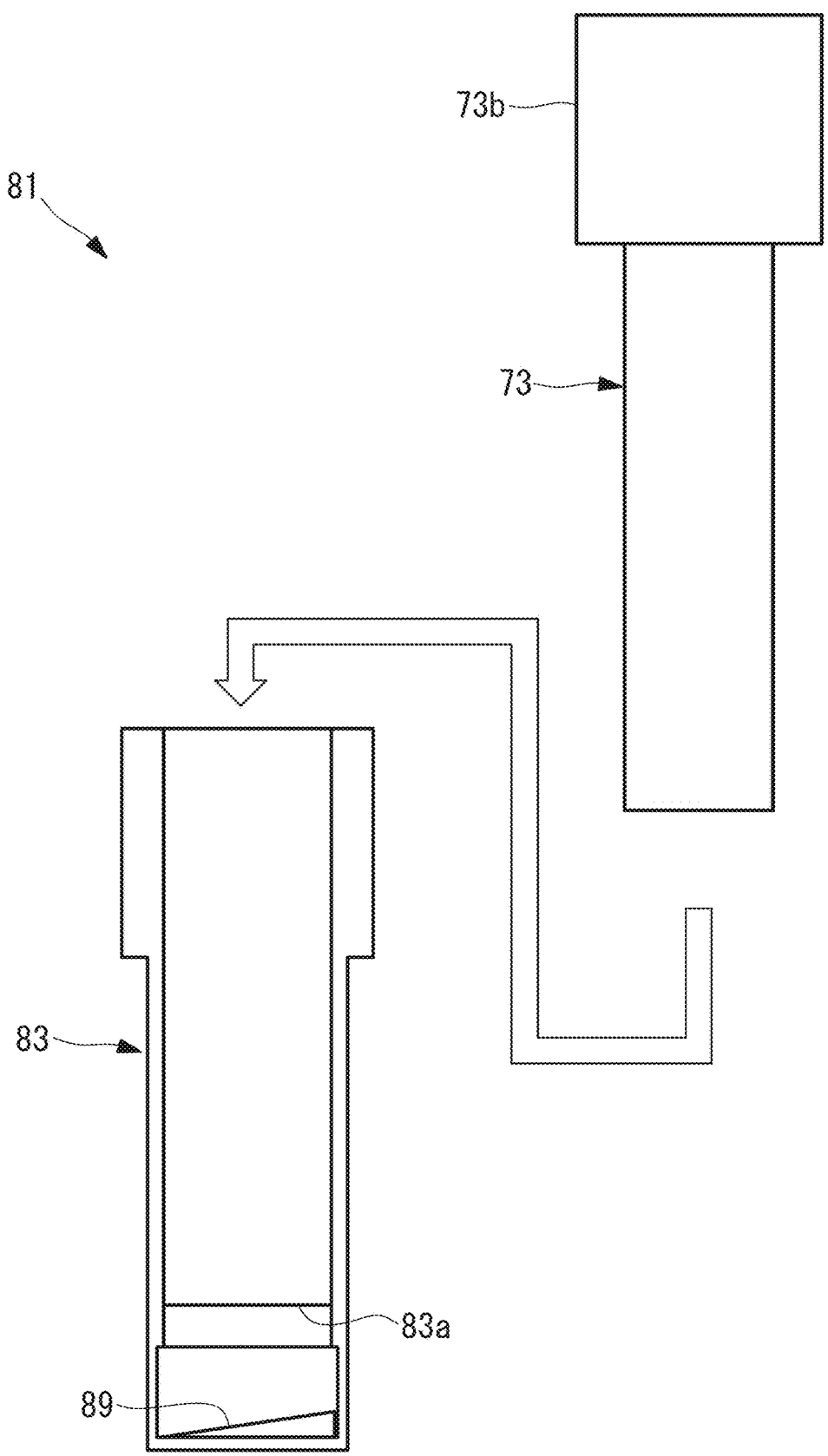
FIG. 27 is a longitudinal sectional view showing the culture-medium-monitoring apparatus according to the eighth embodiment of the present invention.
Figure 28:
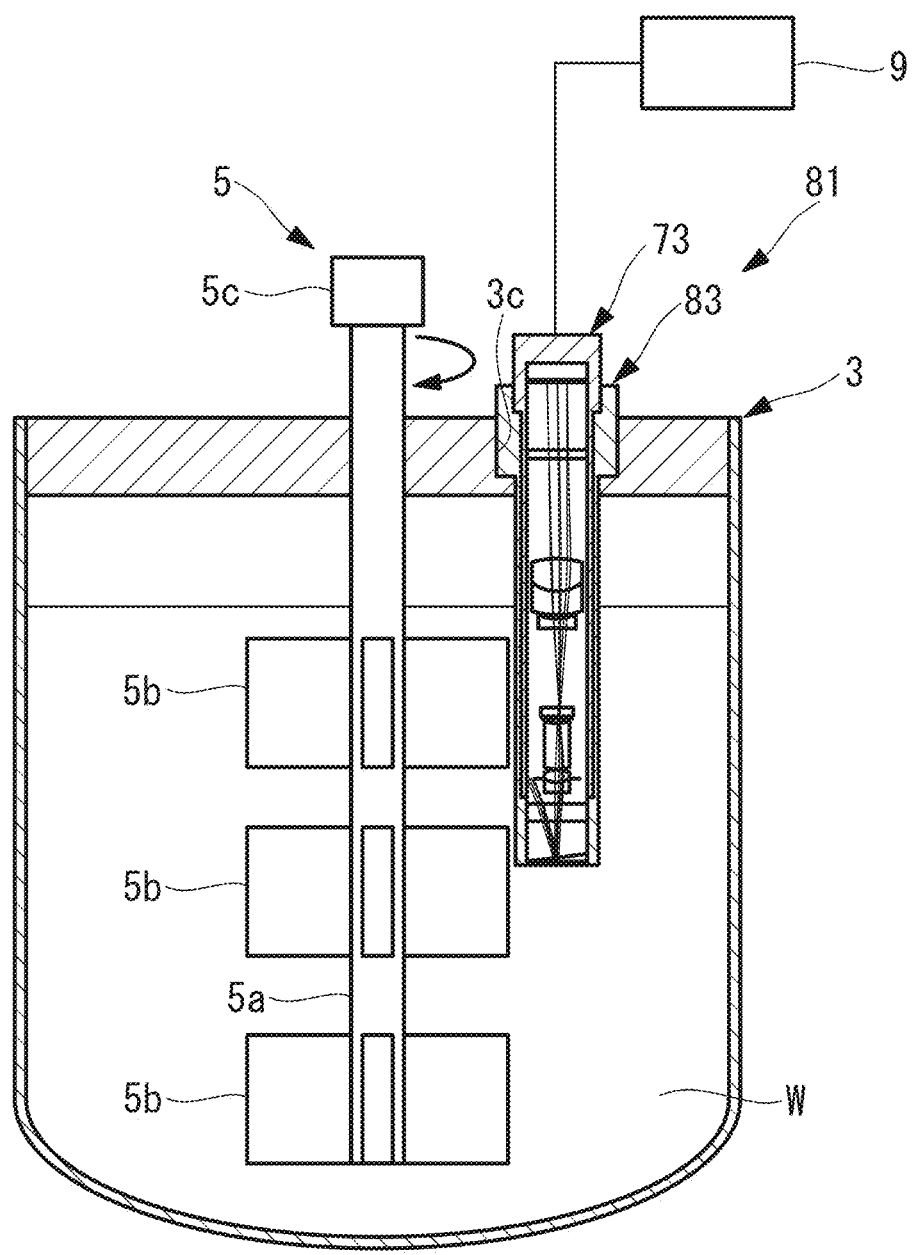
FIG. 28 is a longitudinal sectional view showing the housing and a protective cover forming the culture-medium-monitoring apparatus and the culturing vessel in FIG. 27.

As shown in FIGS. 27 and 28, a culture-medium-monitoring apparatus 81 according to this embodiment differs from the eighth embodiment, for example, in that a protective cover 83 that has an oblique illumination mirror 89 in the interior thereof and that can accommodate the housing 73 therein is included instead of the protective tube 77, and that the optical measurement unit 7 takes a stereo measurement.

In the following, portions having the same configurations as those of the culture-medium-monitoring apparatus 71 according to the eighth embodiment will be given the same reference signs, and descriptions thereof will be omitted.

Figure 29:
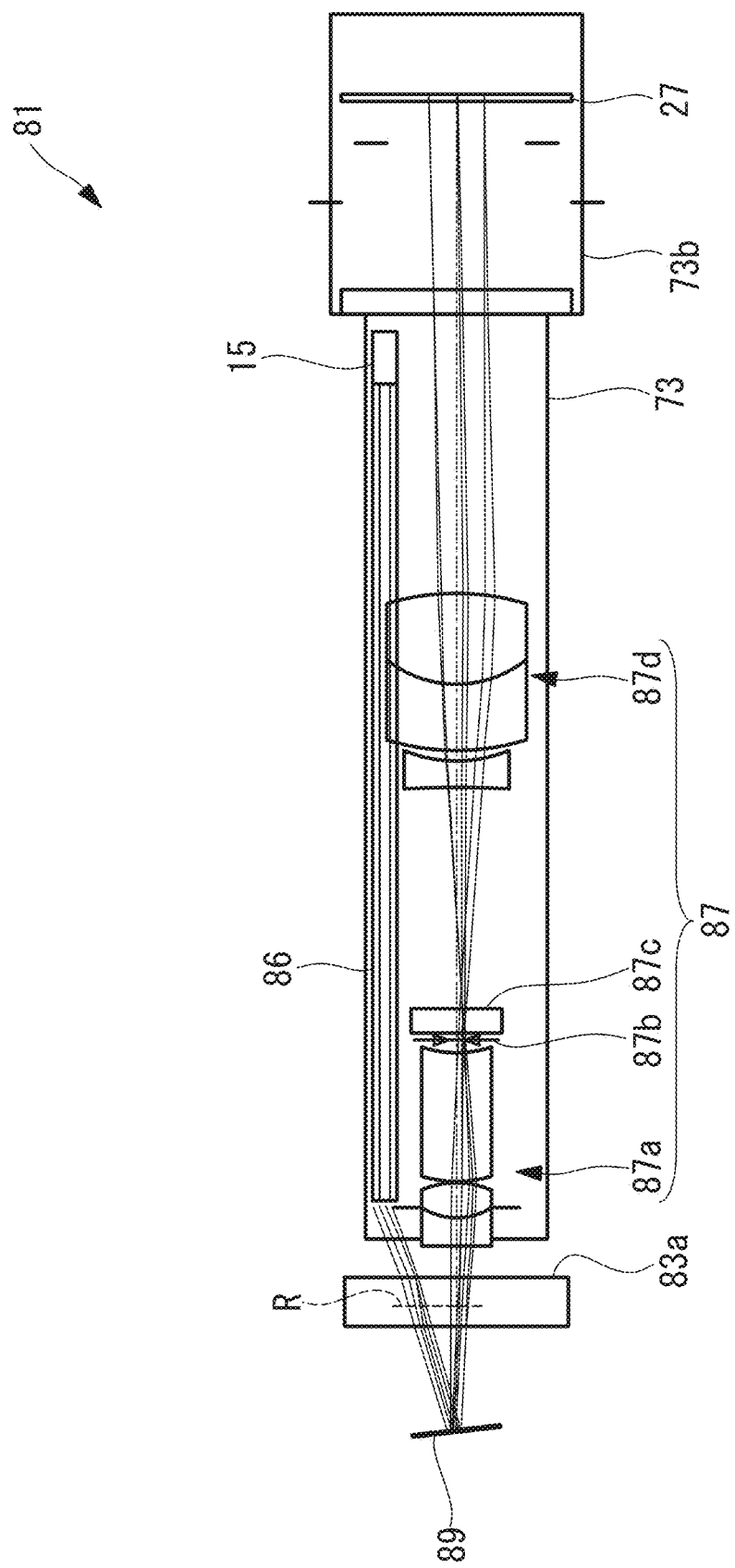
FIG. 29 is a schematic cross-sectional view for explaining the configuration of the culture-medium-monitoring apparatus in FIG. 28.

As shown in FIG. 29, the optical measurement unit 7 according to this embodiment includes: the illumination light source 15; a light guide fiber 86 that guides the illumination light beam emitted from the illumination light source 15; a stereo optical system 87 that forms, for the same cells S, two images that are viewed from different points of view and that have parallax with respect to each other; and the two-dimensional image-acquisition device 27 that individually captures the two images formed by the stereo optical system 87.

The illumination light source 15, the stereo optical system 87, and the two-dimensional image-acquisition device 27 are accommodated in the housing 73. In this embodiment, the housing 73 has, at a base-end portion thereof in the longitudinal direction, a flange portion 73b that expands in a width direction intersecting the longitudinal direction.

The illumination light source 15 is disposed on the base-end side of the housing 73.

The light guide fiber 86 guides the illumination light beam coming from the illumination light source 15 to the distal end of the housing 73.

The stereo optical system 87 includes, sequentially from the distal-end side: an objective optical system 87a that collects the observation light beam coming from the specific region R; an aperture stop portion 87b that divides the observation light beam collected by the objective optical system 87a; a deflection prism 87c that deflects the observation light beams that have been divided by the aperture stop portion 87b; and an imaging optical system 87d that causes the observation light beams that have been deflected by the deflection prism 87c to form separate images.

The stereo optical system 87 has a stereo structure in one of the directions that are orthogonal to the optical axis of the stereo optical system 87 and that are orthogonal to each other. In the following, the arraying direction of the points of view of the stereo optical system 87 will be referred to as the stereo direction.

The aperture stop portion 87b is disposed at the pupil position of the objective optical system 87a. In the aperture stop portion 87b, for example, two holes (not shown) are formed separated from each other in the stereo direction.

The two-dimensional image-acquisition device 27 is disposed on the most base-end side of the housing 73.

The protective cover 83 has a cylindrical shape that can be inserted into the culturing liquid W via the port 3c of the culturing vessel 3 in a state in which the housing 73 is accommodated therein. When the protective cover 83 is inserted into the port 3c, an O-ring (not shown) seals off a gap between the port 3c and the protective cover 83. The protective cover 83 is sterilized, and can be replaced, serving as a disposable component that is disposed each time the protective cover 83 is used. The protective cover 83 has, in the state in which the housing 73 is accommodated therein, an inner diameter at which the flange portion 73b of the housing 73 abuts against an insertion port of the protective cover 83 and a length that allows a space to be formed between a distal end of the protective cover 83 and the distal end of the housing 73.

The protective cover 83 has, at a distal-end portion in the longitudinal direction thereof, openings 83a provided in two side surfaces thereof facing each other in the width direction. The openings 83a are disposed between the distal end of the protective cover 83 and the objective optical system 87a in the state in which the housing 73 is inserted into the protective cover 83. The openings 83a have a size that allow the cells S and the culturing liquid W to pass through the interior of the protective cover 83 in the width direction. The openings 83a may be openings formed, for example, as a result of dividing the protective cover 83 into a distal-end side and a base-end side in the longitudinal direction and joining the distal-end side and the base-end side at two locations in a circumferential direction of the protective cover 83.

At the distal end of the protective cover 83, the oblique illumination mirror 89, which is disposed facing the base-end side of the protective cover 83, is provided.

In the oblique illumination mirror 89, a reflection surface thereof has a slope at a prescribed angle with respect to the longitudinal direction of the protective cover 83. The oblique illumination mirror 89 reflects, in the state in which the housing 73 is accommodated in the protective cover 83, the illumination light beam that is made to exit the light guide fiber 86 toward the stereo optical system 87 at an angle at which the illumination light beam travels in a direction orthogonal to the stereo direction. By doing so, in the culturing vessel 3, it is possible to obliquely illuminate a specific region R in which the cells S are present in the culturing liquid W that has intruded into the openings 83a of the protective cover 83.

Because the interior of the culturing liquid W and the interior of the cells S have different refractive indices from each other, the light beam is bent at the boundary between the culturing liquid W and the cells S. For example, a portion at which the light beam is bent in a direction in which the light beam travels outside the pupil of the objective optical system 87a becomes dark at the image surface, and a portion at which the light beam is bent in a direction in which the light beam travels inside the pupil of the objective optical system 87a becomes bright at the image surface. Therefore, it is possible to acquire an image of the cells S with an enhanced contrast as a result of obliquely illuminating the cells S by means of the oblique illumination mirror 89.

Next, the operation of the culture-medium-monitoring apparatus 81 according to this embodiment will be described.

In the case in which the state of the culturing liquid W is monitored by means of the culture-medium-monitoring apparatus 81 having the above-described configuration while culturing the cells S, first, the housing 73 to which the protective cover 83 is attached is inserted into the culturing liquid W via the port 3c of the culturing vessel 3, and the illumination light beam is generated from the illumination light source 15.

The illumination light beam emitted from the illumination light source 15 is guided by the light guide fiber 86, and is made to exit toward the oblique illumination mirror 89 in the protective cover 83 from the distal end of the light guide fiber 86. By doing so, the illumination light beam reflected by the oblique illumination mirror 89 is radiated onto the specific region R in which the cells S are present in the culturing liquid W that has intruded into the protective cover 83 from the openings 83a.

Then, as a result of the illumination light beam that has passed through the specific region R entering the stereo optical system 87 in the housing 73, the stereo optical system 87 forms two images that are viewed from different points of view with respect to the specific region R and that have parallax with respect to each other. By doing so, the two-dimensional image-acquisition device 27 acquires, with respect to the plurality of cells S, two two-dimensional images that are viewed from the different points of view and that have parallax with respect to each other for each of the individual cells S, for example, a top-side image and a bottom-side image shown in FIG. 30.

Figure 30:
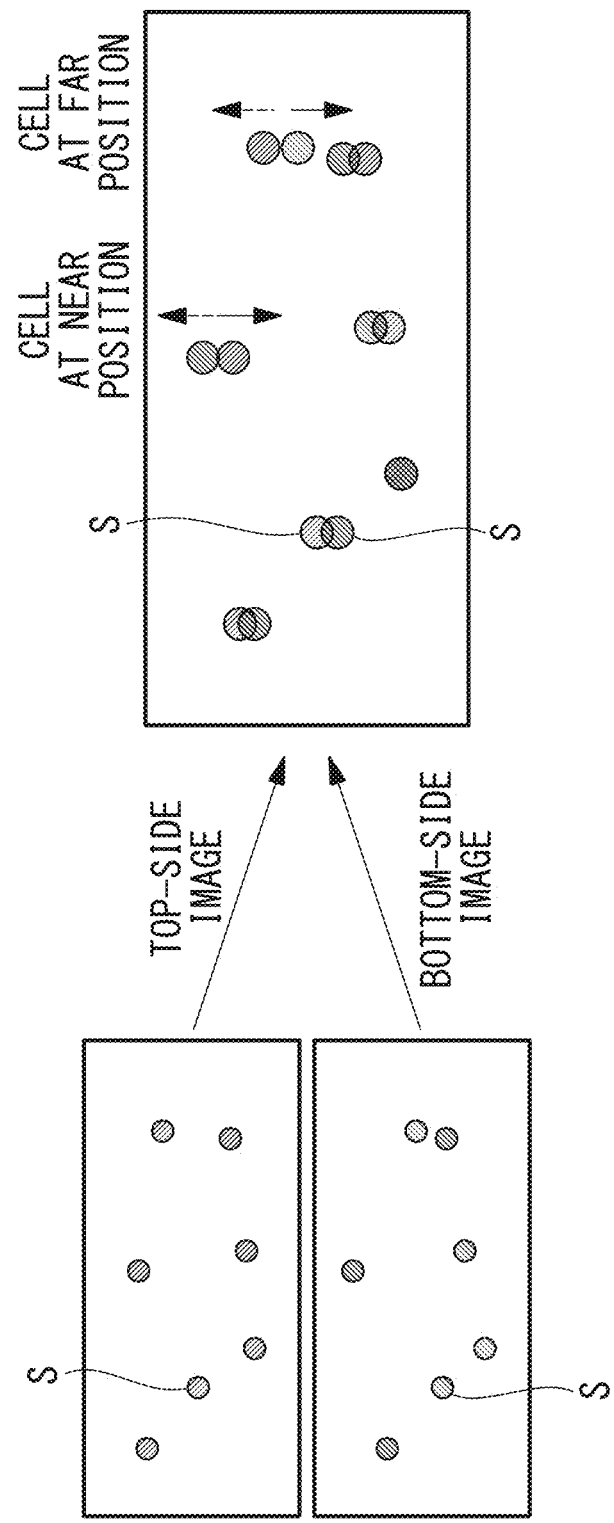
FIG. 30 is a diagram showing examples of a top-side image and a bottom-side image acquired by the monitoring apparatus in FIG. 29, and an example of a state in which the top-side image and the bottom-side image are combined.

Next, as a result of the image-analyzing portion 10 analyzing one of or both of the top-side image and the bottom-side image shown in FIG. 30, the background pixels of these images are extracted, and, subsequently, the representative pixel values of the extracted background pixels are calculated.

In this case, as a result of the stereo optical system 87 causing, with respect to the plurality of cells S in the culturing liquid W, two images that are viewed from different points of view and that have parallax with respect to each other to be formed for each of the individual cells S, the positions of the same cells S in the stereo direction are displaced between these two images acquired by the two-dimensional image-acquisition device 27 in opposite directions in accordance with the distance from the stereo optical system 87.

Therefore, because the three-dimensional positions of the individual cells S are ascertained on the basis of the amounts by which the positions of the individual cells S are displaced, it is possible to accurately distinguish, by means of the image-analyzing portion 10, the cells S that are contained in the specific region R and the cells S that are not contained therein. In other words, it is possible to accurately define the specific region R as a three-dimensional region, and it is possible to accurately measure, for example, the density of cells that are present in a three-dimensional region defined by the specific region R. By doing so, with the culture-medium-monitoring apparatus 81 according to this embodiment, as with the eighth embodiment, it is possible to precisely calculate the representative pixel values of the background pixels of the images of the specific region R in the culturing vessel 3 regardless of the shape, the size, and so forth of the culturing vessel 3 to be used.

The above-described seventh to ninth embodiments can be modified to the following configuration.

For example, the configuration of the sixth embodiment may be applied to each of the seventh to ninth embodiments, specifically, the configuration in which the culture-medium-supplying portion 33 and the culture-medium-discharging portion 41 are provided, and the control portion 9 controls the culture-medium-supplying portion 33 and the culture-medium-discharging portion 41.

For example, the configuration according to the modification of the sixth embodiment may be applied to each of the seventh to ninth embodiments, specifically, the configuration in which the supply port 37a of the culture-medium-supplying pipe 37 is disposed in the vicinity of the bottom surface 3b of the culturing vessel 3, the suction port 45a of the culture-medium-discharging pipe 45 is disposed near the liquid surface of the culturing liquid W, and the control portion 9 simultaneously performs discharging of the culturing liquid W by means of the culture-medium-discharging portion 41 and supplying of the culturing liquid W by means of the culture-medium-supplying portion 33.

The above-described fifth to ninth embodiments can be modified to the following configurations.

As a first modification, in the fifth to ninth embodiments and the modifications thereof, for example, a portion of or the entire control portion 9 may be included in the optical measurement unit 7 without separating the control portion 9 and the optical measurement unit 7. For example, the control portion 9 may be accommodated in a housing that accommodates the illumination light source 15, the two-dimensional image-acquisition device 27, and so forth.

Figure 31:
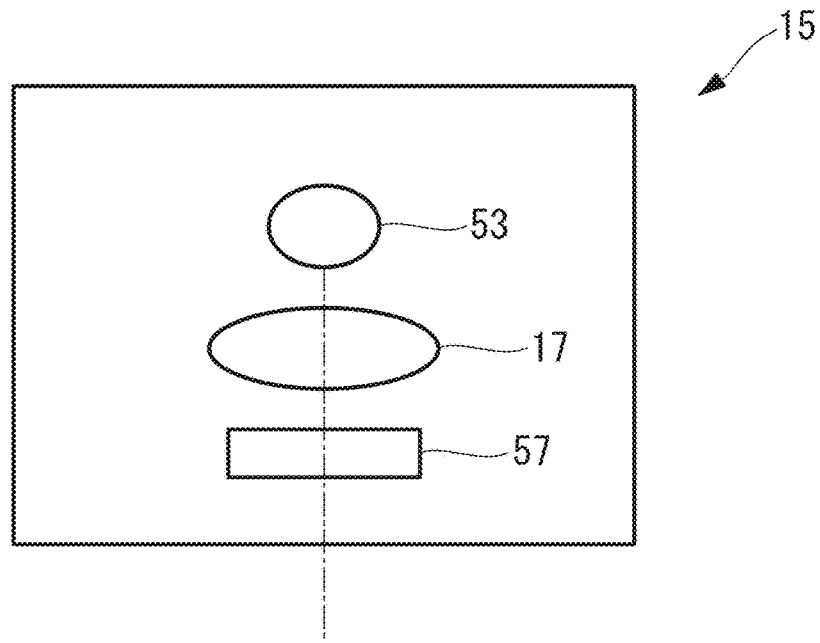
FIG. 31 is a schematic configuration diagram showing an optical measurement unit according to a second modification of the fifth to eighth embodiments.

As a second modification, as shown in FIG. 31, in the fifth to ninth embodiments and the modifications thereof, for example, the white light source 53, such as a halogen light source, may be employed as the illumination light source instead of the illumination light source 15 such as an LED, and the collecting lens 17 that converts the light beam emitted from the white light source 53 to collimated light beam and the bandpass filter 57 that extracts a specific wavelength from the light beam converted to the collimated light beam by the collecting lens 17 may be employed.

In this case, in the case in which the light intensity of the illumination light beam is measured, the illumination light beam emitted from the white light source 53 may be radiated onto the specific region R in the culturing vessel 3 by turning on the white light source 53 or by opening/closing a shutter (not shown).

With this modification, because a halogen light source and a bandpass filter are inexpensive, it is possible to achieve a cost reduction. It is possible to apply the configurations of the white light source 53 and the bandpass filter 57 to various types of culturing liquids W, because the degree of freedom for wavelength selection is high.

Figure 32:
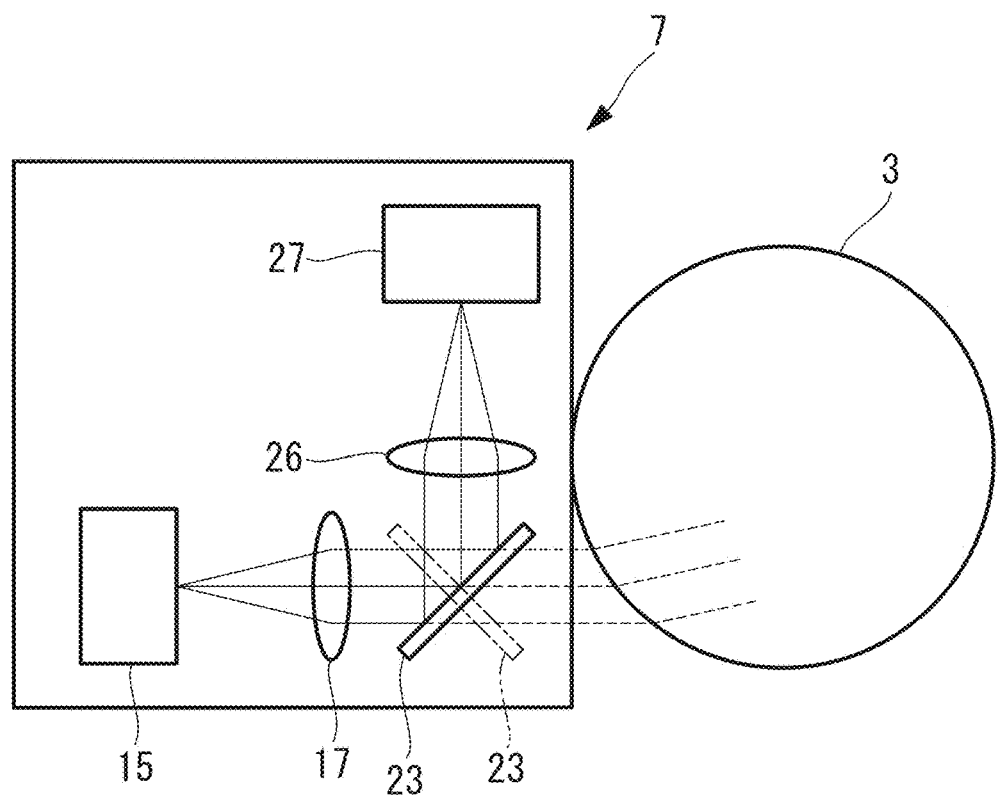
FIG. 32 is a schematic configuration diagram showing an optical measurement unit according to a third modification of the fifth to eighth embodiments.

As a third modification, as shown in FIG. 32, in the fifth to seventh embodiments and the modifications thereof, for example, the orientation of the half mirror 23 may be made rotatable by 90°. Then, by rotating the half mirror 23 by 90°, the paths of the illumination light beam may be switched between the case in which the half mirror 23 allows the illumination light beam coming from the illumination light source 15 to pass therethrough toward the culturing vessel 3 and the case in which the half mirror 23 reflects the illumination light beam coming from the illumination light source 15 toward the two-dimensional image-acquisition device 27.

In this case, first, by disposing the half mirror 23 at the angle indicated by the solid line in FIG. 32, the illumination light beam coming from the illumination light source 15 is made to enter the two-dimensional image-acquisition device 27 by means of the half mirror 23, and the light intensity of the illumination light beam that has not passed through the culturing liquid W is measured by the two-dimensional image-acquisition device 27.

Next, by switching the angle of the half mirror 23 to the angle indicated by the broken line in FIG. 32, the illumination light beam coming from the illumination light source 15 is made to pass therethrough toward the culturing liquid W in the culturing vessel 3. Then, the illumination light beam that returns by passing through the culturing liquid W again after being folded back by the retroreflective member 19 is made to enter the two-dimensional image-acquisition device 27 by means of the half mirror 23, and the image of the observation light beam returning from the specific region R in the culturing vessel 3 is captured by the two-dimensional image-acquisition device 27.

Then, when determining the state of the culturing liquid W on the basis of the changes over time in the representative pixel values of the background pixels of the images of the specific region R, the influence of the fluctuation on the output of the illumination light source 15 may be corrected by using the intensity of the illumination light beam that has not passed through the culturing liquid W. By doing so, even in the case in which the output of the illumination light source 15 fluctuates, it is possible to accurately assess the state of the culturing liquid W.

As a fourth modification, in the fifth to ninth embodiments and the modifications thereof, the deterioration of the culturing liquid W may be measured by means of a color change.

Figure 33:
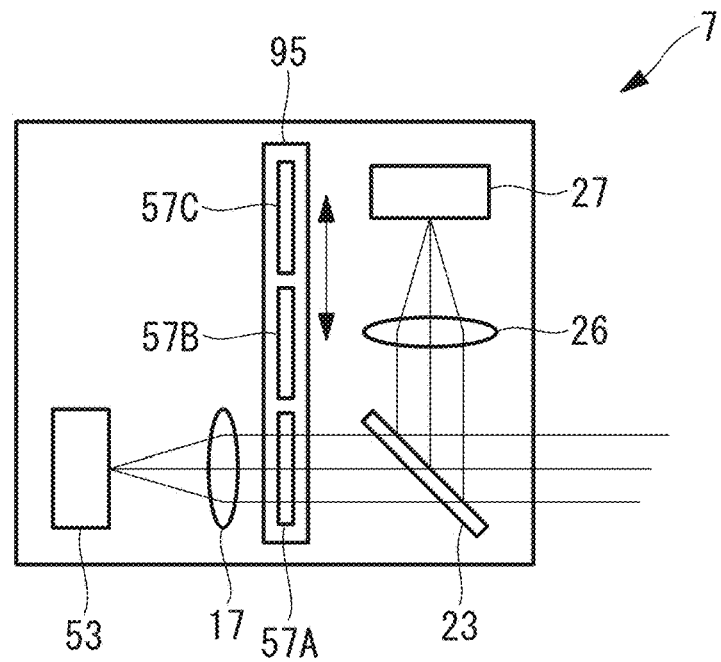
FIG. 33 is a schematic configuration diagram showing an optical measurement unit according to a fourth modification of the fifth to eighth embodiments.

As shown in FIG. 33, in this modification, for example, the white light source 53 such as a halogen light source is employed as the illumination light source. Three bandpass filters 57A, 57B, and 57C having different transmission wavelength and a switching mechanism 95, such as a slider, that selectively disposes one of the three bandpass filters 57A, 57B, and 57C in the path of the illumination light beam, are disposed between the collecting lens 17 and half mirror 23. Dulbecco MEM containing 0.001% phenol red and 10% fetal bovine serum is employed as the culturing liquid W.

The bandpass filter 57A is, for example, a filter (BP441) in which the center wavelength is 441 nm and the band width, that is, the transmission wavelength band, is 10 nm. The bandpass filter 57B is, for example, a filter (BP578) in which the center wavelength is 578 nm and the transmission wavelength band is 10 nm. The bandpass filter 57C is, for example, a filter (BP634) in which the center wavelength is 634 nm and the transmission wavelength band is 10 nm.

First, as preparation, the relationship between the pH and the absorbance of the culturing liquid W is experimentally determined.

First, images of the observation light beam coming from the specific region R in the culturing vessel 3 in which both the cells S and the culturing liquid W are not accommodated are captured by the two-dimensional image-acquisition device 27 by using each of the bandpass filters 57A, 57B, and 57C. In this case, the representative pixel value of the background pixels of an image of the specific region R when the bandpass filter 57A is used is assumed to be $I_{0\_441}$, the representative pixel value of the background pixels of an image of the specific region R when the bandpass filter 57B is used is assumed to be $I_{0\_578}$, and the representative pixel value of the background pixels of an image of the specific region R when the bandpass filter 57C is used is assumed to be $I_{0\_634}$. Here, because images of the specific region R in the culturing vessel 3 in which both the cells S and the culturing liquid W are not accommodated are captured, the pixels containing the cells S are not extracted, and all of the pixels are extracted as the background pixels.

Next, an image of the observation light beam coming from the specific region R in the culturing vessel 3 accommodating the culturing liquid W having a known pH is captured by the two-dimensional image-acquisition device 27 by using each of the bandpass filters 57A, 57B, and 57C. The pH of the culturing liquid W may be measured, for example, by directly inserting a pH sensor (not shown) into the culturing liquid W. In this case, the representative pixel value of the background pixels of an image of the specific region R when the bandpass filter 57A is used is assumed to be 1441, the representative pixel value of the background pixels of an image of the specific region R when the bandpass filter 57B is used is assumed to be $I_{578}$, and the representative pixel value of the background pixels of an image of the specific region R when the bandpass filter 57C is used is assumed to be $I_{634}$. Here, because images of the specific region R in the culturing vessel 3 in which only the culturing liquid W is accommodated are captured, the pixels containing the cells S are not extracted, and all of the pixels are extracted as the background pixels.

In this case, the absorbances ($A_{441}$, $A_{578}$, and $A_{634}$) of the specific region R for the respective wavelengths are expressed by the following expressions:

$$A_{441} = -\log(I_{441}/I_{0\_441});$$

$$A_{578} = -\log(I_{578}/I_{0\_578}); \text{ and}$$

$$A_{634} = -\log(I_{634}/I_{0\_634}).$$

The above-described measurements are taken for the culturing liquid W at multiple pH values, and a relational expression between the absorbance and the pH of the culturing liquid W is determined for each of the wavelengths. For example, the following is obtained:

$$\text{pH} = \log\{(A_{441}-A_{634})/(A_{578}-A_{634})\}*1.19+7.86,$$

where 1.19 is the slope of a straight line obtained when the $\log\{(A_{441}-A_{634})/(A_{578}-A_{634})\}$ is plotted against the pH, and 7.86 is the intercept of the straight line.

Next, as the main measurement, the changes over time in the culturing liquid W are measured.

The images of the specific region R are acquired by switching among the individual bandpass filters 57A, 57B, and 57C, the background pixels are extracted from the acquired images, and the representative pixel values of the background pixels are calculated. Next, the absorbances for the respective wavelengths in the main measurement are determined by using the representative pixel values $I_{0\_441}$, $I_{0\_578}$, and $I_{0\_634}$ of the background pixels for the respective wavelengths in the state in which the cells S and the culturing liquid W are not accommodated in the culturing vessel 3, which are experimentally determined in the preparation. The changes over time in the pH values of the culturing liquid W are determined from the absorbances for the respective wavelengths, which are determined here, and the relational expression between the absorbance and the pH determined in the preparation.

With this modification, because the deterioration of the culturing liquid W is determined by determining the pH values of the culturing liquid W from the changes over time in the representative pixel values of the background pixels of the images of the specific region R at the plurality of wavelengths, it is possible to enhance the measurement precision of the deterioration of the culturing liquid W.

Figure 34:
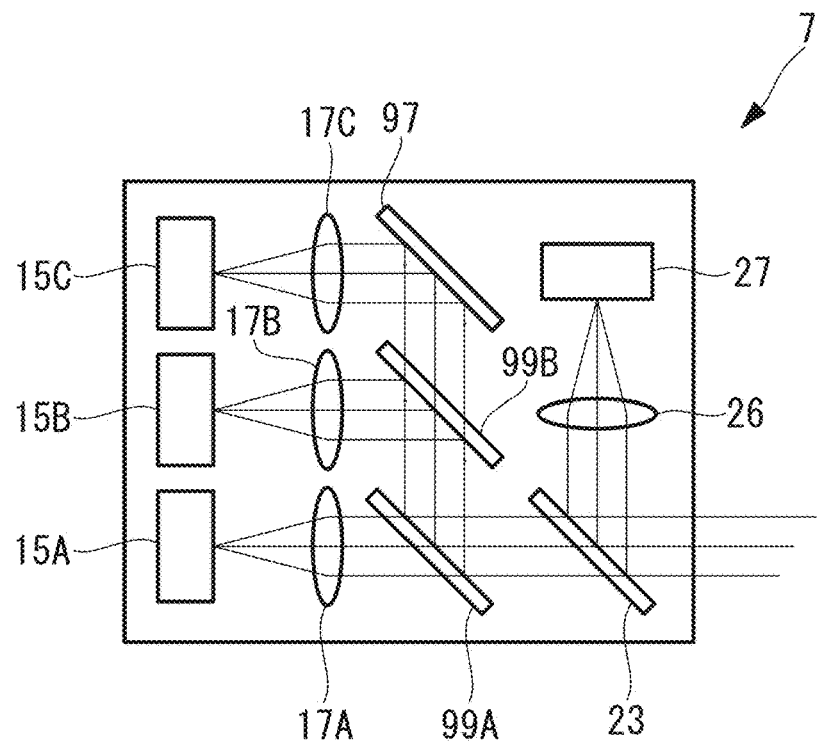
FIG. 34 is a schematic configuration diagram showing an optical measurement unit according to a fifth modification of the fifth to eighth embodiments.

As a fifth modification, as shown in FIG. 34, for example, a plurality of LED light sources (monochromatic light sources) 15A, 15B, and 15C that emit illumination light beams at different wavelengths may be employed as illumination light sources instead of the white light source 53 of the above-described fourth modification. In the example shown in FIG. 34, the LED light source 15A emits a 441-nm monochromatic light beam, the LED light source 15B emits a 578-nm monochromatic light beam, and the LED light source 15C emits a 634-nm monochromatic light beam.

In this case, collecting lenses 17A, 17B, and 17C that collect the illumination light beams coming from the individual LED light sources 15A, 15B, and 15C, and a mirror 97 and dichroic mirrors 99A and 99B that reflect or transmit the illumination light beams collected by the collecting lenses 17A, 17B, and 17C to combine the optical paths of the illumination light beams may be employed instead of the collecting lens 17, the bandpass filters 57A, 57B, and 57C and the switching mechanism 95.

With this modification, instead of switching among the bandpass filters 57A, 57B, and 57C as in the above-described fourth modification, it is possible to change the measurement wavelength by simply switching ON/OFF the individual LED light sources 15A, 15B, and 15C.

Figure 35:
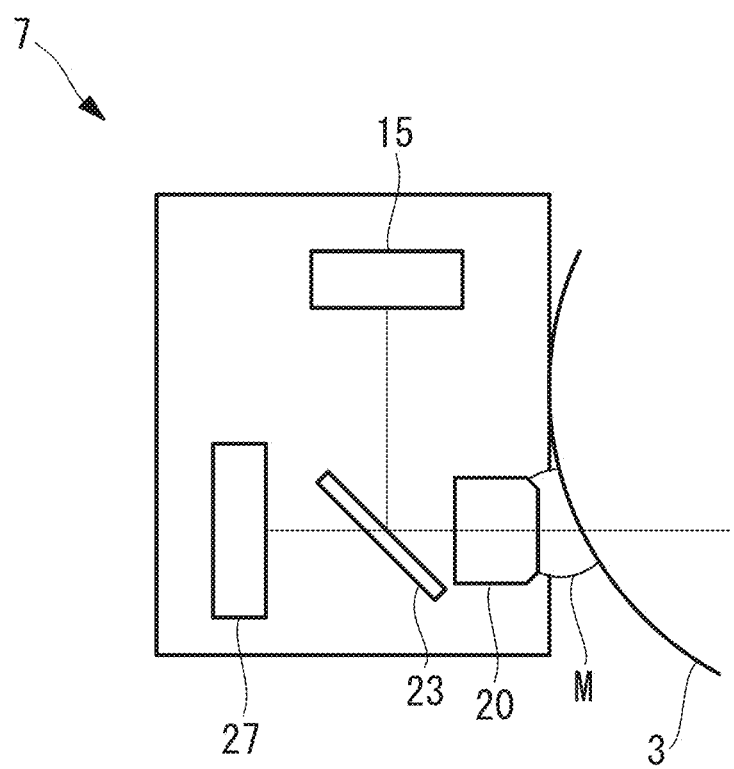
FIG. 35 is a schematic configuration diagram showing an optical measurement unit according to a sixth modification of the fifth to eighth embodiments.

As a sixth modification, as shown in FIG. 35, in the above-described fifth to seventh embodiments and the modifications thereof, for example, a culture medium having a refractive index that is different from that of air, for example, an immersion culture medium M of the objective lens 20, may be filled in a space between the objective lens 20 and the culturing vessel 3. The immersion culture medium M is, for example, water, oil, a gel, or a water absorptive polymer. It is preferable that the refractive index of the immersion culture medium M be the same as or close to the refractive indices of the culturing vessel 3 and the culturing liquid W.

With this modification, with the immersion culture medium M between the objective lens 20 and the culturing vessel 3, it is possible to reduce the influence of the refraction at the boundary between the culturing vessel 3 and the culturing liquid W for the illumination light beam that enters the culturing vessel 3 from the objective lens 20 and the observation light beam that enters the objective lens 20 from the culturing vessel 3. Thus, it is possible to enhance the resolving power by increasing the numerical aperture of the objective lens 20.

As a seventh modification, in the above-described fifth to seventh embodiments and the modifications thereof, a white light source that generates a light beam at wavelengths over the entire visible light range may be employed as the illumination light source, a color CCD (not shown) may be employed as the two-dimensional image-acquisition device 27, and the control portion 9 may determine the state of the culturing liquid W on the basis of the relationship between the hue and the pH of the culturing liquid W determined from the background pixels of an image of the specific region R in the culturing vessel 3 acquired by the color CCD in a single image capturing.

In this case, the image-analyzing portion 10 extracts the background pixels from the color image of the specific region R acquired by the color CCD, and calculates color information of the culturing liquid W, that is, a hue angle of the culturing liquid W, by using the average of the respective RGB intensities in the background pixels or the median thereof as the representative pixel value.

Figure 36:
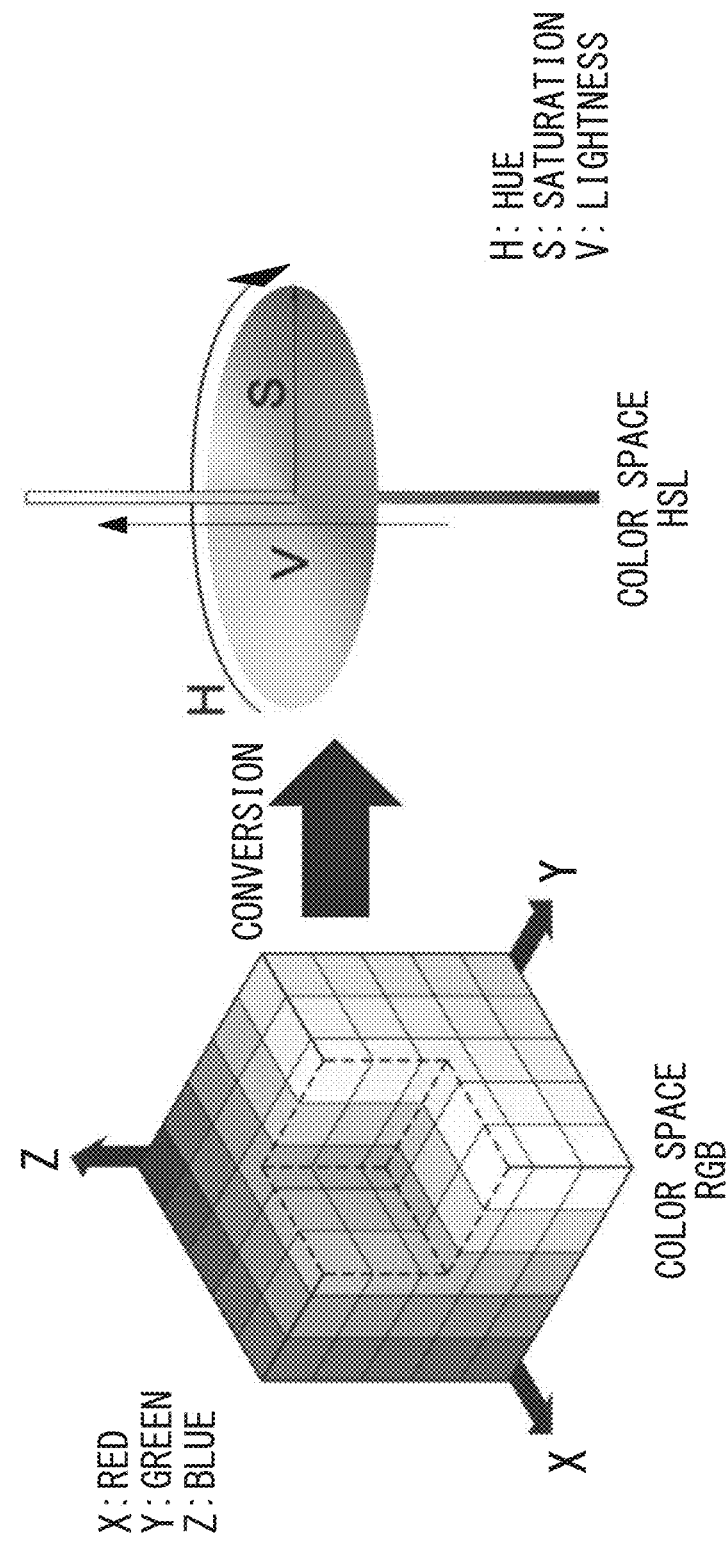
FIG. 36 is a diagram showing examples of a square color space (RGB) and a columnar color space (HSL) according to a seventh modification of the fifth to eighth embodiments.

Specifically, as shown in FIG. 36, for example, the image-analyzing portion 10 converts a square color space (RGB), in which the respective RGB intensities are assigned to three axes, namely, X (red), Y (green), and Z (blue), to a columnar color space (HSL) consisting of three components, namely, hue (H), saturation (S), and lightness (L), thus calculating the hue angle of the culturing liquid W. The hue indicates color information independently of the saturation and the lightness.

Figure 37:
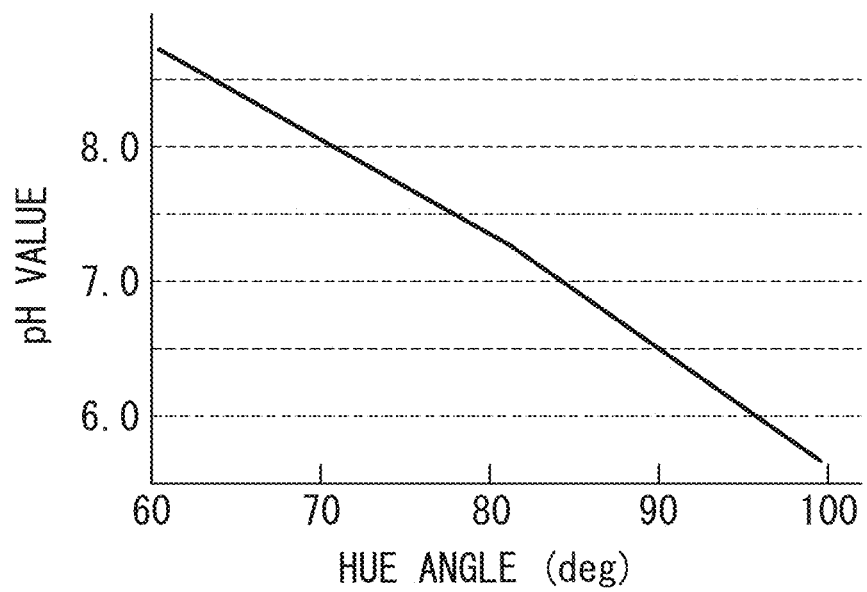
FIG. 37 is a diagram showing an example of a table indicating the relationship between the hue angle and the pH according to the seventh modification of the fifth to eighth embodiments.

The control portion 9 stores, for example, a table shown in FIG. 37 indicating the relationship between the hue angle and the pH values. The control portion 9 determines, on the basis of this table, the pH values of the culturing liquid W from the hue angle calculated by the image-analyzing portion 10, and determines the state of the culturing liquid W from the changes over time in the pH values.

With this modification, it is possible to more accurately determine the state of the culturing liquid W as a result of determining the pH values of the culturing liquid W from the color information of the culturing liquid W.

Figure 38:
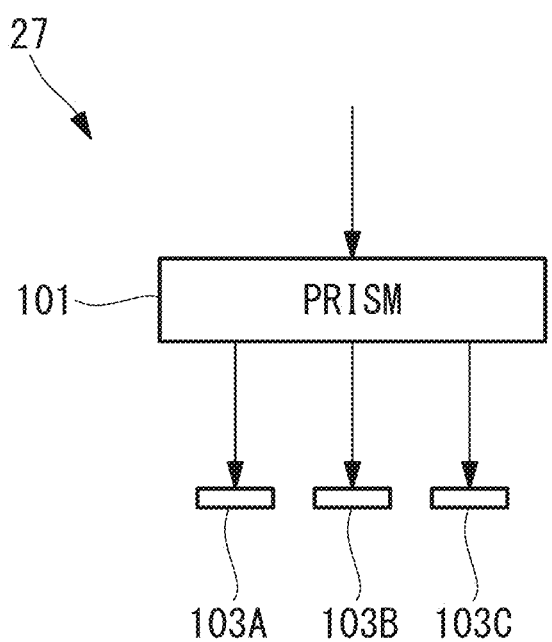
FIG. 38 is a schematic configuration diagram showing an example of a three-chip color CCD according to the seventh modification of the fifth to eighth embodiments.

In this modification, a three-chip color CCD may be employed as the two-dimensional image-acquisition device 27. As shown in FIG. 38, in this case, the three-chip color CCD may be formed, for example, from a dichroic prism 101 that separates the wavelengths of the observation light beam coming from the specific region R into R(red), G(green), B(blue) wavelength ranges, and a red image sensor 103A, a green image sensor 103B, and a blue image sensor 103C that capture images of the light beams in the individual wavelength ranges, which have been subjected to the wavelength separation.

Figure 39:
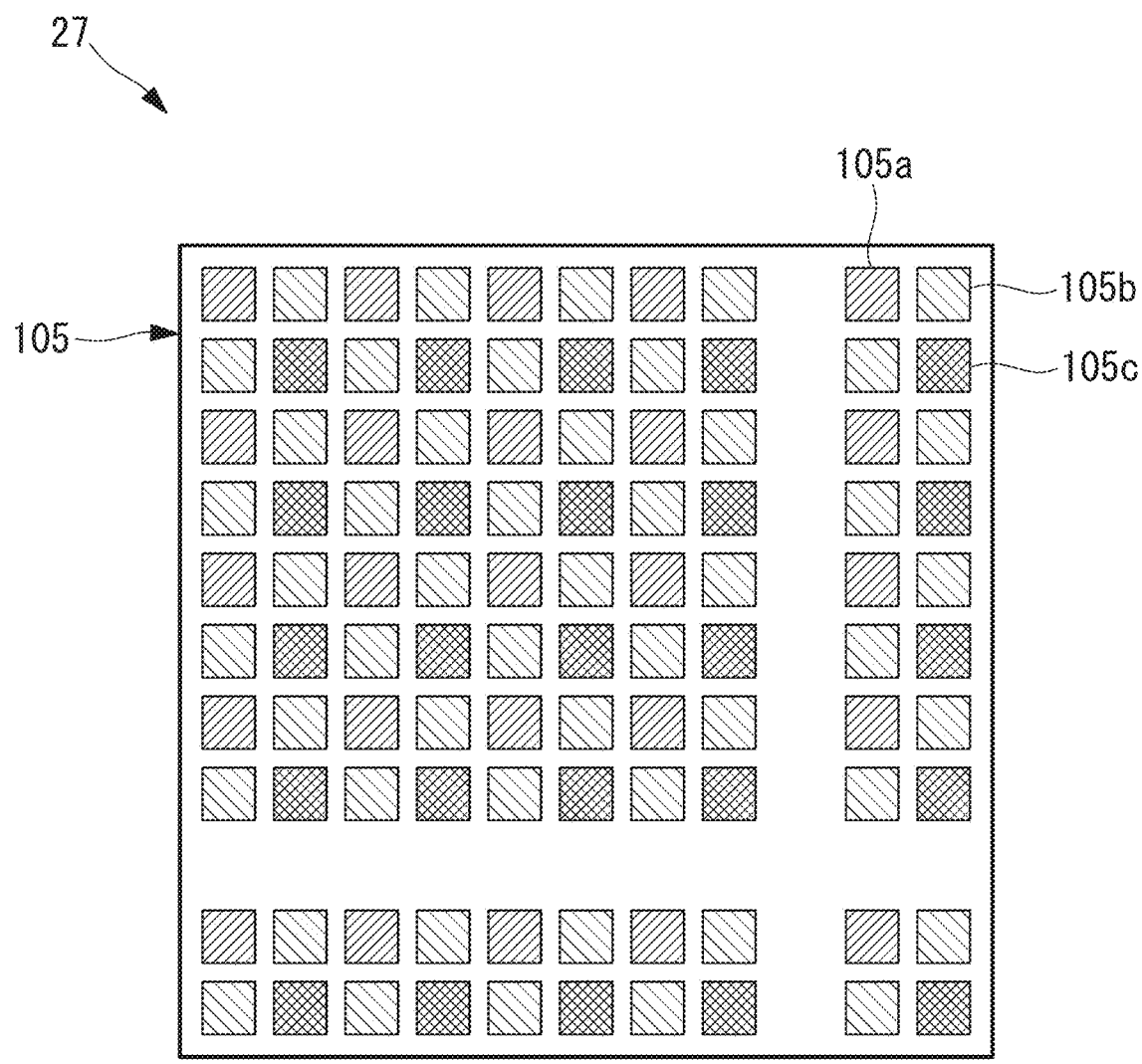
FIG. 39 is a schematic configuration diagram showing an example of a single-chip color CCD according to the seventh modification of the fifth to eighth embodiments.

In this modification, a single-chip color CCD may be employed as the two-dimensional image-acquisition device 27. In this case, for example, as shown in FIG. 39, the single-chip color CCD may be formed from a single image sensor 105 in which a plurality of color filters 105a that allow the light beams at the red wavelength range to pass therethrough, a plurality of color filters 105b that allow the light beams at the green wavelength range to pass therethrough, and a plurality of color filters 105c that allow the light beams at the blue wavelength range to pass therethrough are allocated to a plurality of pixels.

This modification can be modified to the following configuration.

In this modification, the white light source 53 is employed as the illumination light source, and a color CCD is employed as the two-dimensional image-acquisition device 27. Alternatively, a plurality of LED light sources (not shown) that generate light beams at the respective RGB color wavelengths or the white light source 53 and switchable bandpass filters (not shown) that extract the respective RGB wavelengths may be employed as the illumination light source. A monochromatic CCD (not shown) may be employed as the two-dimensional image-acquisition device 27.

In this case, color images of the specific region R may be sequentially acquired by performing, in a synchronized manner, switching of the RGB illumination wavelengths performed by switching the plurality of LED light sources or the plurality of bandpass filters, and image capturing of the observation light beam coming from the specific region R performed by means of the monochromatic CCD.

With this modification, it is possible to enhance the detection sensitivity of the observation light beam as a result of employing a monochromatic CCD as the two-dimensional image-acquisition device.

As an eighth modification, in the fifth to ninth embodiments and the modifications thereof, the state of the culturing liquid W may be monitored, for example, in a state in which the entire culture-medium-monitoring apparatuses 1, 31, 51, 71, and 81, including the optical measurement unit 7 and the culturing vessel 3, are disposed in a dark place.

With this configuration, it is possible to accurately measure the intensity of the illumination light beam that has been made to pass through the culturing liquid W without being influenced by light from illumination equipment, light from a monitor, and external light.

In the above-described fifth to ninth embodiments, although the closed-bottom cylindrical culturing vessel 3 formed of an optically transparent material has been described as an example of the vessel, it is possible to employ, as the culturing vessel, a vessel having an arbitrary shape such as a bag-like shape, a spherical shape, or a box-like shape. For example, a disposable bag-like culturing vessel may be employed. It is possible to employ a culturing vessel made of an arbitrary material such as a hard material or a soft material such as vinyl. The culturing vessel 3 need not be entirely transparent, and the culturing vessel 3 may have a transparent portion that allows the illumination light beam to pass therethrough in a portion thereof.

As has been described above, with the above-described fifth to ninth embodiments, it is possible to measure the state of the culturing liquid W in a non-contact manner without directly inserting a pH sensor into the culturing liquid W, and thus, it is possible to reduce the risk of contaminating the culturing system.

Although the embodiments of the present invention have been described in detail with reference to the drawings, the specific configurations are not limited to these embodiments, and design alterations or the like within a range that does not depart from the scope of the present invention are also encompassed. For example, there is no limitation to the forms in which the present invention is applied to the above-described individual embodiments and modifications, and the present invention may be applied to forms in which these embodiments and modifications are appropriately combined without particular limitation. Even in the case in which the culture-medium-supplying portion 33 and the culture-medium-discharging portion 41 are used in combination with the alert-issuing portion 13 and the culture medium replacement is automatically performed by means of control performed by the control portion 9, a notification may be issued to the user, indicating that the timing for replacing the culture medium has arrived.

The first embodiment can be modified to the following configuration.

Figure 40:
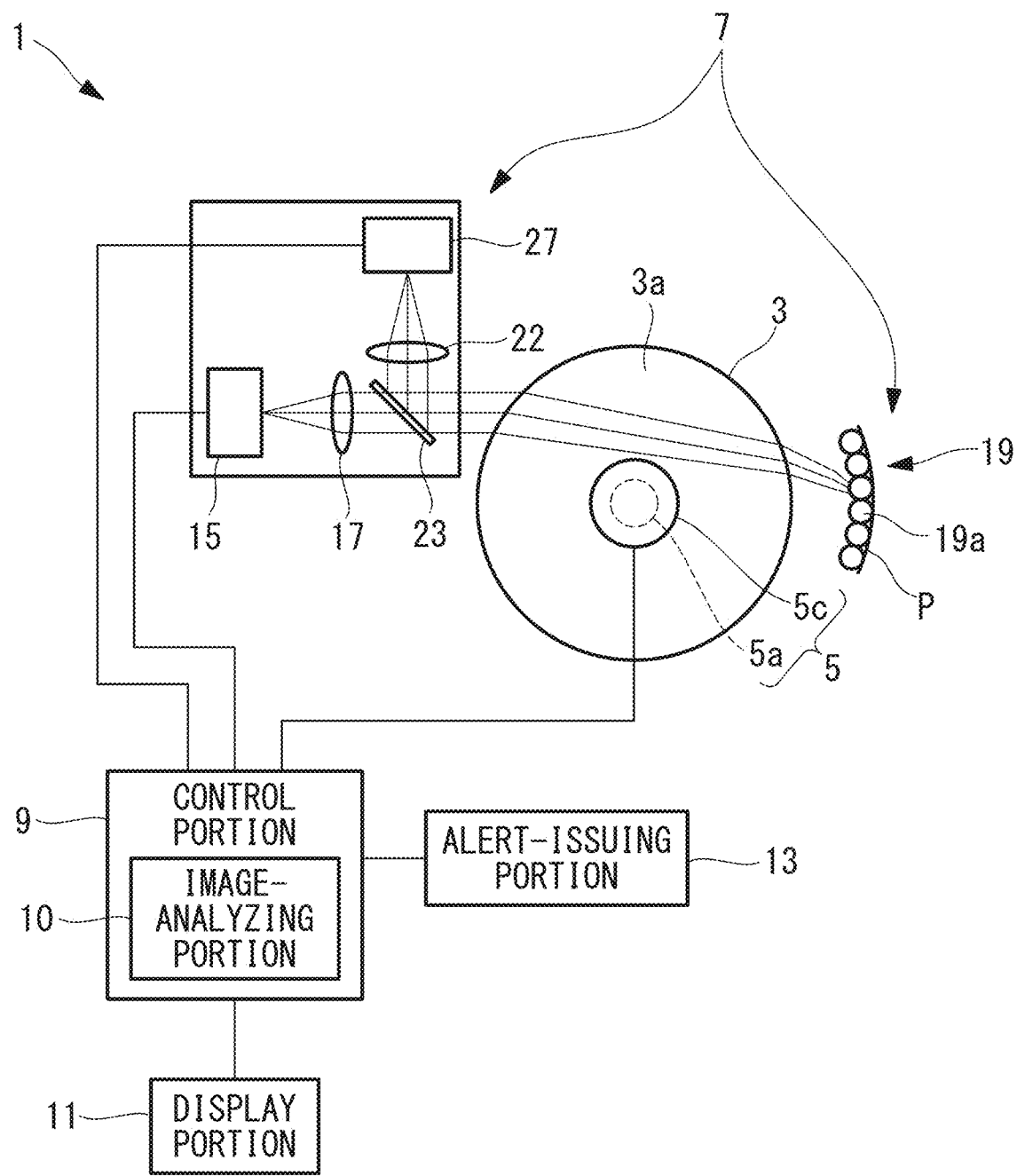
FIG. 40 is a schematic configuration diagram showing a modification of the culture-medium-monitoring apparatus according to the first embodiment of the present invention.

As shown in FIG. 40, for example, the configuration of the first embodiment may be applied to this embodiment, specifically, the two-dimensional image-acquisition device 27 may be provided as the light detector 25, and the images of the specific region R may be acquired by means of the two-dimensional image-acquisition device 27. In addition, the image-analyzing portion 10 may be provided in the control portion 9, the images of the specific region R acquired by the two-dimensional image-acquisition device 27 may be divided into the pixels containing the cells S and the background pixels, and the representative pixel values representing the background pixels may be calculated. Here, the calculated representative pixel values can be treated as the intensities of the illumination light beam in the first embodiment. Then, the control portion 9 determines the state of the culturing liquid W on the basis of the changes over time in the representative pixel values, which are the intensities of the illumination light beam that has passed through the culturing liquid W.

Note that the "two-dimensional image-acquisition device (image-acquisition portion) 27" described in the above-described fifth to ninth embodiments corresponds to the "light detector (light-detecting portion) 25" described in the above-described first to fourth embodiments and the "image-acquisition device 67" described in the third embodiment. The "representative pixel value" described in the above-described fifth to ninth embodiments corresponds to the "intensity of the illumination light beam" detected by the light detector 25 described in the above-described first to fourth embodiments and the image-acquisition device 67 described in the third embodiment.

As a result, the following aspects are read from the above described embodiment of the present invention.

In a bioreactor, vessels to be used are widely variable in terms of the shape, the size, and the material, and there are also disposable vessels made of vinyl or the like. In the case in which the transmittance of a culture medium is measured, an illumination light beam entering the vessel and the illumination light beam exiting the vessel are refracted at surfaces of the vessel; however, unpredictable refraction associated with the shape, the material, and the placement of the vessel occurs, and thus, there are cases in which it is not possible to guide the illumination light beam to the transmittance-measuring detector. In particular, in the case in which the vessel is made of vinyl, the refraction situation of the illumination light beam may greatly change even with a slight change in the surface of the vessel caused by stirring of a culturing liquid or the like. In this case, there is a problem in that it is not possible to determine whether the change in the transmittance is due to a change in a culture medium itself or due to a change in the shape of the surface of the vessel.

An aspect of the present invention has been conceived in light of the above-described circumstances, an object thereof is to provide a culture-medium-monitoring apparatus with which it is possible to stably monitor a culture medium even with a wide variety of culturing vessels, and the present invention provides the following solutions.

An aspect of the present invention is a culture-medium-monitoring apparatus including: an optical measurement unit that includes an illuminating portion that radiates an illumination light beam onto a culture medium in a vessel, a retroreflective member that has an array in which a plurality of micro-reflective elements are arrayed, that is disposed so as to sandwich the vessel between the illuminating portion and the retroreflective member, and that reflects the illumination light beam that has passed through the culture medium in the vessel, and a light-detecting portion that detects an intensity of the illumination light beam that has passed through the culture medium in the vessel after being reflected by the retroreflective member; and a control portion that causes the intensity of the illumination light beam to be repeatedly detected at a prescribed timing by controlling the optical measurement unit, and that determines a state of the culture medium on the basis of a change over time in the intensity of the illumination light beam.

With this aspect, in the optical measurement unit, when the illumination light beam is radiated onto the culture medium in the vessel by means of the illuminating portion, the illumination light beam that has passed through the culture medium is reflected by the retroreflective member, which is disposed on the opposite side of the illuminating portion with the vessel sandwiched between the illuminating portion and the retroreflective member, and the illumination light beam reflected by the retroreflective member is detected by the detection optical system after passing through the culture medium in the vessel again. Then, the control portion determines the state of the culture medium in the vessel on the basis of the change over time in the intensity of the illumination light beam that has passed through the culture medium in the vessel, which is repeatedly detected at the prescribed timing as a result of the control portion controlling the optical measurement unit.

In this case, as a result of being formed from an array in which the plurality of micro-reflective elements are arrayed, the retroreflective member reflects the illumination light beam that has entered the retroreflective member in completely the same direction as the entry direction. In other words, it is possible to return the illumination light beam that has passed through the culture medium in the vessel by means of the retroreflective member in the opposite direction through the same optical path as the entry optical path regardless of the material, the shape, the size, and so forth of the vessel. By doing so, it is possible to reliably detect the intensity of the illumination light beam that has passed through the culture medium in the vessel by means of the light-detecting portion. Therefore, it is possible to stably monitor the culture medium on the basis of the state of the culture medium determined by the control portion even with a wide variety of culturing vessels.

The culture-medium-monitoring apparatus according to the above-described aspect may include a notifying portion that issues a notification about information to a user, wherein the control portion may issue, by means of the notifying portion, a notification about a timing for replacing the culture medium to the user.

Because the state of the culture medium is accurately determined by the control portion regardless of the material, the shape, the size, and so forth of the vessel, it is possible to prompt a user to replace the culture medium at an appropriate timing by means of the control portion via the notifying portion.

The culture-medium-monitoring apparatus according to the above-described aspect may include: a culture-medium-supplying portion that supplies the culture-medium to the vessel; and a culture-medium-discharging portion that discharges the culture medium from the vessel, wherein, in the case in which the control portion determines that the timing for replacing the culture medium has arrived on the basis of the change over time in the intensity of the illumination light beam detected by the light-detecting portion, the control portion may cause the culture-medium-discharging portion to discharge a portion of the culture medium from the vessel, and the control portion may cause the culture-medium-supplying portion to supply a new culture medium to the vessel.

It is possible to replace the culture medium in the vessel as a result of discharging a portion of the culture medium in the vessel by means of the culture-medium-discharging portion, while supplying the new culture medium to the vessel by means of the culture-medium-supplying portion. Whether the culture medium in the vessel has deteriorated, that is, whether the timing for replacing the culture medium has arrived, is ascertained by means of the control portion on the basis of the change over time in the intensity of the illumination light beam detected by the light-detecting portion. Therefore, as a result of the control portion controlling the culture-medium-supplying portion and the culture-medium-discharging portion on the basis of the change over time in the intensity of the illumination light beam, it is possible to replace the culture medium at an accurate timing without requiring time and effort on the part of the user.

The culture-medium-monitoring apparatus according to the above-described aspect may include an stirrer that stirs the culture-medium in the vessel, wherein the control portion may cause a speed at which the culture medium is stirred by the stirrer to be reduced when detecting the intensity of the illumination light beam by means of the light-detecting portion.

The cells accommodated in the vessel together with the culture medium are suspended in the culture medium when the culture medium is stirred by the stirrer, and move downward in the culture medium due to gravity when the speed at which the culture medium is stirred by the stirrer is reduced. As a result of the control portion reducing the speed at which the culture medium is stirred by the stirrer when detecting the intensity of the illumination light beam by means of the light-detecting portion, it is possible to reduce the number of suspended cells present in the path of the illumination light beam generated by the optical measurement unit, and thus, it is possible to suppress influences of scattering of the illumination light beam caused by the suspended cells. Therefore, it is possible to more accurately measure the transmittance of the culture medium.

In the culture-medium-monitoring apparatus according to the above-described aspect, the optical measurement unit may include a detection optical system that causes an image of cells suspended in the culture medium irradiated with the illumination light beam to be formed on the light-detecting portion.

With this configuration, it is possible to observe the cells suspended in the culture medium on the basis of the image formed in the light-detecting portion by the detection optical system.

In the culture-medium-monitoring apparatus according to the above-described aspect, the optical measurement unit the optical measurement unit may include a phase contrast optical system that generates a phase contrast image of the cells.

With this configuration, it is possible to acquire a high-resolution, high-contrast image of the cells in the culture medium by means of the phase contrast optical system.

The culture-medium-monitoring apparatus according to the above-described aspect may include an stirrer that stirs the culture medium in the vessel, wherein the control portion may repeatedly perform detection of the intensity of the illumination light beam and acquisition of the image of the cells by means of the light-detecting portion, may cause the speed at which the culture medium is stirred by the stirrer to be reduced when detecting the intensity of the illumination light beam, and may cause the culture medium to be stirred without reducing the speed at which the culture medium is stirred by the stirrer when acquiring the image of the cells.

With this configuration, when detecting the intensity of the illumination light beam by means of the light-detecting portion, the number of the suspended cells that are present in the path of the illumination light beam generated by the optical measurement unit is reduced as a result of reducing the speed at which the culture medium is stirred by the stirrer, and thus, influences of scattering of the illumination light beam caused by the suspended cells are suppressed. By doing so, it is possible to enhance the measurement precision of the transmittance of the culture medium. On the other hand, when acquiring the image of the cells in the culture medium by means of the light-detecting portion, the cells are suspended in the culture medium by stirring the culture medium by the stirrer, and thus, it is possible to acquire an image of the cells in the suspended state.

In the culture-medium-monitoring apparatus according to the above-described aspect, the illuminating portion may include a monochromatic light source that emits the illumination light beam at a single wavelength.

In the culture-medium-monitoring apparatus according to the above-described aspect, the monochromatic light source may include a white light source and a bandpass filter that extracts only the single wavelength from the light beam emitted from the white light source.

In the culture-medium-monitoring apparatus according to the above-described aspect, the monochromatic light source may be an LED light source.

In the culture-medium-monitoring apparatus according to the above-described aspect, the illuminating portion may include a light source that emits, as the illumination light beam, a plurality of monochromatic light beams at different wavelengths, wherein the control portion may determine the state of the culture medium on the basis of changes over time in intensities of the light beams at the respective wavelengths that have passed through the culture medium and that are detected by the light-detecting portion.

With this configuration, it is possible to enhance the precision of determining the state of the culture medium on the basis of the changes over time in the intensities of light beams at the plurality of wavelengths that pass through the culture medium as a result of employing the light beams at the plurality of wavelengths.

In the culture-medium-monitoring apparatus according to the above-described aspect, the light source may include: a white light source; and a plurality of bandpass filters that are provided so that said bandpass filters can be inserted into and retracted from a path of a light beam emitted from the white light source, and that extract, from the light beam coming from the white light source, only single wavelengths that differ from each other.

With this configuration, it is possible to radiate a light beam at a desired wavelength simply by replacing the bandpass filters, and thus, it is possible to enhance the versatility of the apparatus and the operability by the operator.

In the culture-medium-monitoring apparatus according to the above-described aspect, the light source may include a plurality of LED light sources at different wavelengths.

This configuration requires a simple operation of simply switching the LED to be turned on, and it is possible to eliminate the time and effort for switching the bandpass filter to be disposed in the path of the illumination light beam or the like.

Applying the absorbance measuring system described in Patent Literature 2 to the bioreactor described in Patent Literature 1 requires both of the optical system that acquires an image of the cells in the culture medium and the optical system that measures changes in the transmittance of the culture medium to be incorporated into the apparatus as separate components, and thus, there is a problem in that the apparatus becomes complex.

Although it is conceivable to substitute the optical system that measures the transmittance of the culture medium with the optical system that acquires the image of the cells, if the cells are present in a region in which the image is acquired, that is, the image-acquisition region in the culture medium, scattering and absorption of the illumination light beam caused by the cells exert significant influences. Because the cells are randomly suspended in the culture medium as a result of stirring the culture medium, it is difficult to identify a region in which the cells are not present in the culture medium. It is not possible to distinguish whether the change in the lightness of the acquired images is due to deterioration of the culture medium or scattering of the illumination light beam caused by the cells, and thus, there is a problem in that it is not possible to accurately monitor the state of the culture medium.

Another aspect of the present invention has been conceived in light of the above-described circumstances, and an object thereof is to provide a culture-medium-monitoring apparatus with which it is possible to accurately monitor the state of a culture medium without increasing the complexity of the apparatus, and the present invention provides the following solutions.

Another aspect of the present invention is a culture-medium-monitoring apparatus including: an illuminating portion that radiates an illumination light beam onto a specific region in which cells and a culture medium are present in a vessel; an image-acquisition portion that acquires an image of the specific region by capturing an image of an observation light beam coming from the specific region irradiated with the illumination light beam; an image-analyzing portion that divides the image of the specific region acquired by the image-acquisition portion into pixels containing the cells and background pixels, and that calculates a representative pixel value that represents the background pixels; and a control portion that repeatedly acquires images of the specific region at a prescribed timing by means of the image-acquisition portion, that calculates the representative pixel values of the individual acquired images of the specific region by means of the image-analyzing portion, and that determines the state of the culture medium on the basis of changes over time in the calculated representative pixel values.

With this aspect, when the illumination light beam is radiated onto the specific region in which the culture medium and the cells are present in the vessel by means of the illuminating portion, the images of the specific region in the vessel are acquired by the image-acquisition portion on the basis of the observation light beam coming from that specific region, and the representative pixel values of the background pixels, which do not contain the pixels containing the cells, are calculated from the acquired images of the specific region by the image-analyzing portion. Then, the control portion determines the state of the culture medium in the vessel on the basis of the changes over time in the representative pixel values of the background pixels individually calculated by the image-analyzing portion from the respective images of the specific region in the vessel, which are repeatedly acquired at the prescribed timing by the image-acquisition portion.

In this case, although the region in which the cells are present in the culture medium changes over time, as a result of monitoring the changes over time only in the background pixels that are extracted from the images of the specific region in the vessel and that do not contain the pixels containing the cells, it is possible to determine the state of the culture medium without being influenced by scattering of the illumination light beam caused by the cells. As a result of monitoring the state of the culture medium by using the image-acquisition portion with which the cells are observed, it is not necessary to separately provide an optical system for monitoring the state of the culture medium, and thus, it is possible to simplify the apparatus. Therefore, it is possible to accurately monitor the state of the culture medium on the basis of the images of the specific region in the vessel without increasing the complexity of the apparatus.

The culture-medium-monitoring apparatus according to the above-described aspect may include a retroreflective member that has an array in which a plurality of micro-reflective elements are arrayed, that is disposed so as to sandwich the vessel between the illuminating portion and the retroreflective member, and that reflects the illumination light beam that has passed through the specific region in the vessel, wherein the image-acquisition portion may acquire an image of the specific region irradiated again with the illumination light beam that has been reflected by the retroreflective member.

As a result of being formed from an array in which the plurality of micro-reflective elements are arrayed, the retroreflective member reflects the illumination light beam that has entered the retroreflective member in completely the same direction as the entry direction. In other words, it is possible to radiate the illumination light beam that has passed through the specific region in the vessel onto the specific region in the vessel again by passing through the same optical path as the entry optical path as a result of being reflected by the retroreflective member and thus it is possible to reliably acquire an image of that specific region by means of the image-acquisition portion, regardless of the material, the shape, the size, and so forth of the vessel. Therefore, it is possible to stably monitor the culture medium on the basis of the state of the culture medium determined by the control portion even with a wide variety of culturing vessels.

In the culture-medium-monitoring apparatus according to the above-described aspect, the illuminating portion may include an oblique illumination optical system that obliquely illuminates the specific region from a direction that is inclined with respect to an optical axis of the image-acquisition portion.

It is possible to monitor the state of the culture medium by using an image having the sense of three-dimensionality with respect to the colorless, transparent cells by means of the oblique illumination optical system.

In the culture-medium-monitoring apparatus according to the above-described aspect, the illuminating portion and the image-acquisition portion may form a phase contrast optical system that generates a phase contrast image of the specific region.

It is possible to monitor the state of the culture medium by using a high-resolution, high-contrast image of the cells in the culture medium by means of the phase contrast optical system.

The culture-medium-monitoring apparatus according to the above-described aspect may include a housing that has a transparent portion that allows a light beam to pass therethrough, and that accommodates the illuminating portion and the image-acquisition portion, wherein, in a state in which the housing is inserted into the culture medium in the vessel, the illumination light beam may be radiated onto the specific region by means of the illuminating portion via the transparent portion, and an image of the specific region may be acquired by means of the image-acquisition portion through the transparent portion.

With this configuration, because the image of the specific region is acquired in the state in which the housing is inserted into the culture medium in the vessel, it is possible to avoid greatly being influenced by limitations on the shape, the size, the material, and so forth of the vessel to be used. Therefore, it is possible to cope with a wide variety of vessels.

The culture-medium-monitoring apparatus according to the above-described aspect may include a reflective member that obliquely illuminate the specific region by reflecting, toward the image-acquisition portion, the illumination light beam that has been made to exit to outside the housing from the illuminating portion via the transparent portion.

With this configuration, the area irradiated with the illumination light beam in the vessel is restricted to the space between the transparent portion of the housing and the reflective member, and thus, it is possible to capture images of the cells that have intruded into the space between the transparent portion of the housing and the reflective member.

The culture-medium-monitoring apparatus according to the above-described aspect may include a tubular protective tube that covers a periphery of the housing, wherein the reflective member may be provided at a distal end of the protective tube.

It is possible to operate the housing, the illuminating portion, and the image-acquisition portion in the vessel in the state in which the housing and the illuminating portion and the image-acquisition portion in the housing are safely protected by the protective tube.

The culture-medium-monitoring apparatus according to the above-described aspect may include a notifying portion that issues a notification about information to the user, wherein the control portion issues, by means of the notifying portion, a notification about a timing for replacing the culture medium to the user.

Because the state of the culture medium is accurately determined by the control portion regardless of the material, the shape, the size, and so forth of the vessel, it is possible to prompt the user to replace the culture medium at an appropriate timing by means of the control portion via the notifying portion.

The culture-medium-monitoring apparatus according to the above-described aspect may include a culture-medium-supplying portion that supplies the culture-medium to the vessel; and a culture-medium-discharging portion that discharges the culture-medium from the vessel, wherein, in the case in which the control portion determines that the timing for replacing the culture medium has arrived, the control portion may cause the culture-medium-discharging portion to discharge a portion of the culture medium, and the control portion may cause the culture-medium-supplying portion to supply the new culture medium to the vessel.

It is possible to replace the culture medium in the vessel as a result of discharging a portion of the culture medium in the vessel by means of the culture-medium-discharging portion, while supplying the new culture medium to the vessel by means of the culture-medium-supplying portion. Whether the culture medium in the vessel has deteriorated, that is, whether the timing for replacing the culture medium has arrived, is ascertained by means of the control portion on the basis of the changes over time in the representative pixel values of the background pixels calculated by the image-analyzing portion. Therefore, as a result of the control portion controlling the culture-medium-supplying portion and the culture-medium-discharging portion on the basis of the changes over time in the representative pixel values of the background pixels, it is possible to replace the culture medium at an accurate timing without requiring time and effort on the part of the user.

In the culture-medium-monitoring apparatus according to the above-described aspect, the illuminating portion may include a monochromatic light source that emits the illumination light beam at a single wavelength.

In this case, the monochromatic light source may include a white light source and a bandpass filter that extracts only the single wavelength from the light beam emitted from the white light source, and the monochromatic light source may be an LED light source.

In the culture-medium-monitoring apparatus according to the above-described aspect, the illuminating portion may include a light source that emits, as the illumination light beam, a plurality of monochromatic light beams at different wavelengths, wherein the control portion may determine the state of the culture medium on the basis of changes over time in the representative pixel values of the background pixels of the individual images of the specific region acquired by the image-acquisition portion for the respective wavelengths of the monochromatic light beams radiated onto the specific region.

With this configuration, it is possible to enhance the determination precision of the state of the culture medium on the basis of the changes over time in the representative pixel values of the background pixels of the individual images of the specific region obtained for the respective wavelengths of the monochromatic light beams.

In the culture-medium-monitoring apparatus according to the above-described aspect, the light source may include: a white light source; and a plurality of bandpass filters that are provided so that said bandpass filters can be inserted into and retracted from a path of the light beam emitted from the white light source, and that extract, from a light beam coming from the white light source, only single wavelengths that differ from each other.

With this configuration, it is possible to radiate the light beam at a desired wavelength onto the specific region simply by replacing the bandpass filters, and thus, it is possible to enhance the versatility of the apparatus and the operability for the operator.

In the culture-medium-monitoring apparatus according to the above-described aspect, the light source may include a plurality of LED light sources at different wavelengths.

This configuration requires a simple operation of simply switching the LED to be turned on, and it is possible to eliminate the time and effort for switching the bandpass filter to be disposed in the path of the illumination light beam or the like.

In the culture-medium-monitoring apparatus according to the above-described aspect, the illuminating portion may include a white light source, the image-acquisition portion may include a color CCD, and the control portion may determine the state of the culture medium on the basis of the relationship between hue and pH of the culture medium determined from the background pixels of an image of the specific region acquired by the color CCD.

With this configuration, it is possible to more accurately determine the state of the culture medium by determining the pH of the culture medium from the color information of the culture medium.

REFERENCE SIGNS LIST 1, 31, 51, 71, 81 culture-medium-monitoring apparatus
5 stirrer
7 optical measurement unit
9 control portion
10 image-analyzing portion
13 alert-issuing portion (notifying portion)
15 illumination light source (illuminating portion, monochromatic light source)
15A, 15B, 15C LED light source (monochromatic light source)
17 collecting lens (illuminating portion)
19 retroreflective member
20 objective lens (illuminating portion)
25 light detector (light-detecting portion)
27 two-dimensional image-acquisition device (image-acquisition portion)
29 oblique illumination optical system
33 culture-medium-supplying portion
41 culture-medium-discharging portion
53 white light source
54 illumination optical system (illuminating portion)
57, 57A, 57B, 57C bandpass filter
61 illumination optical system
63 detection optical system
65 phase contrast optical system
67 image-acquisition device (light-detecting portion)
73 housing
77 protective tube
79b bent portion (reflective member)
S cell
W culturing liquid (culture medium)

The invention claimed is:
1. A culture-medium-monitoring apparatus comprising:
an optical measurement unit that includes:

an illuminating portion that is configured to radiate an illumination light beam onto a culture medium in a closed-bottom cylindrical vessel as a bioreactor;

a stirrer disposed in the vessel and configured to rotate around a center axis of the vessel to stir the culture medium in the vessel;

a retroreflective member that has an array in which a plurality of micro-reflective elements are arrayed, that is disposed so as to sandwich the vessel between the illuminating portion and the retroreflective member, and that is configured to reflect the illumination light beam that has passed through the culture medium in the vessel; and a light-detecting portion that is configured to detect an intensity of the illumination light beam that has passed through the culture medium in the vessel after being reflected by the retroreflective member; and a control portion that is configured to cause the intensity of the illumination light beam to be repeatedly detected at a prescribed timing by controlling the optical measurement unit, and to determine a state of the culture medium based on a change over time in the intensity of the illumination light beam, wherein:

the illuminating portion is configured to enter the illumination light beam into the vessel along a direction intersecting a height direction of the vessel, and the illumination portion, the retroreflective member, and the stirrer are disposed at positions at which the illumination light beam traveling inside the vessel does not interfere with the stirrer.

2. The culture-medium-monitoring apparatus according to claim 1, further comprising:

a notifying portion that is configured to issue a notification about information to a user, wherein the control portion issues, via the notifying portion, a notification about a timing for replacing the culture medium to the user.

3. The culture-medium-monitoring apparatus according to claim 1, further comprising:

a culture-medium-supplying portion that is configured to supply the culture medium to the vessel; and a culture-medium-discharging portion that is configured to discharge the culture medium from the vessel, wherein, in a case in which the control portion determines that the timing for replacing the culture medium has arrived based on the change over time in the intensity of the illumination light beam detected by the light-detecting portion, the control portion causes the culture-medium-discharging portion to discharge a portion of the culture medium from the vessel, and causes the culture-medium-supplying portion to supply a new culture medium to the vessel.

4. The culture-medium-monitoring apparatus according to claim 1, wherein the control portion causes a speed at which the culture medium is stirred by the stirrer to be reduced to move suspended cells in the culture medium below an optical path of the optical measurement unit by means of gravity when detecting the intensity of the illumination light beam by means of the light-detecting portion.

5. The culture-medium-monitoring apparatus according to claim 1, wherein the optical measurement unit comprises a detection optical system that is configured to cause an image of cells suspended in the culture medium irradiated with the illumination light beam to be formed on the light-detecting portion.

6. The culture-medium-monitoring apparatus according to claim 5, wherein the optical measurement unit comprises a phase contrast optical system that is configured to generate a phase contrast image of the cells.

7. The culture-medium-monitoring apparatus according to claim 5, wherein the control portion repeatedly performs detection of the intensity of the illumination light beam and acquisition of the image of the cells by means of the light-detecting portion, causes the speed at which the culture medium is stirred by the stirrer to be reduced to move suspended cells in the culture medium below an optical path of the optical measurement unit by means of gravity when detecting the intensity of the illumination light beam, and causes the culture medium to be stirred without reducing the speed at which the culture medium is stirred by the stirrer to make the cells suspended in the culture medium when acquiring the image of the cells.

8. The culture-medium-monitoring apparatus according to claim 1, wherein the illuminating portion comprises a monochromatic light source that is configured to emit the illumination light beam at a single wavelength.

9. The culture-medium-monitoring apparatus according to claim 1, wherein the illuminating portion comprises a light source that is configured to emit, as the illumination light beam, a plurality of monochromatic light beams at different wavelengths, and wherein the control portion determines the state of the culture medium based on changes over time in intensities of the light beams at the respective wavelengths that have passed through the culture medium and that are detected by the light-detecting portion.

10. The culture-medium-monitoring apparatus according to claim 1, wherein:

the illuminating portion radiates the illumination light beam onto a specific region in which the cells and the culture medium are present in the vessel, the light-detecting portion includes an image-acquisition portion that is configured to acquire an image of the specific region by capturing an image of a light beam, which is the illumination light beam that has been reflected by the retroreflective member and that has passed through the specific region in the vessel, the control portion includes an image-analyzing portion that is configured to divide the image of the specific region acquired by the image-acquisition portion into pixels containing the cells and background pixels, and to calculate a representative pixel value that represents the background pixels, and the representative pixel value calculated by the image-analyzing portion corresponds to the intensity of the illumination light beam.

11. The culture-medium-monitoring apparatus according to claim 1, wherein the stirrer comprises a stirring rod and a plurality of stirring blades provided on the stirring rod, and the stirrer stirs the culture medium by rotating the stirring rod.

* * * * *